(12) United States Patent
Hagadorn et al.

(10) Patent No.: US 8,394,902 B2
(45) Date of Patent: *Mar. 12, 2013

(54) PYRIDYLDIAMIDO TRANSITION METAL COMPLEXES, PRODUCTION AND USE THEREOF

(75) Inventors: John R. Hagadorn, Houston, TX (US); Renuka N. Ganesh, Houston, TX (US); Dmitry V. Uborsky, Moscow (RU); Ilya S. Borisov, Moscow (RU); Ivan V. Pruss, Moscow (RU); Alexander Z. Voskoboynikov, Moscow (RU)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/071,738

(22) Filed: Mar. 25, 2011

(65) Prior Publication Data

US 2012/0071616 A1    Mar. 22, 2012

Related U.S. Application Data

(63) Continuation-in-part of application No. 12/180,132, filed on Jul. 25, 2008, now Pat. No. 7,973,116.

(51) Int. Cl.
*C08F 4/16* (2006.01)
*C07F 17/00* (2006.01)

(52) U.S. Cl. ........ 526/172; 502/155; 502/167; 502/117; 502/104

(58) Field of Classification Search ............. 526/172; 502/104, 117, 155, 167
See application file for complete search history.

(56) References Cited

U.S. PATENT DOCUMENTS

| | | | |
|---|---|---|---|
| 5,318,935 | A | 6/1994 | Canich et al. |
| 6,103,657 | A | 8/2000 | Murray |
| 6,521,793 | B1 | 2/2003 | Guram et al. |
| 6,610,805 | B1 | 8/2003 | Guram et al. |
| 6,683,141 | B1 | 1/2004 | Gibson et al. |
| 6,750,345 | B2 | 6/2004 | Goh et al. |
| 6,900,321 | B2 | 5/2005 | Boussie et al. |
| 7,018,949 | B2 | 3/2006 | Boussie et al. |
| 7,041,765 | B2 | 5/2006 | Tau et al. |
| 7,045,583 | B2 | 5/2006 | Kuchta et al. |
| 7,102,006 | B2 | 9/2006 | Vogel et al. |
| 7,164,020 | B2 | 1/2007 | Vogel |
| 7,425,661 | B2 | 9/2008 | McConville et al. |
| 2002/0156279 | A1 | 10/2002 | Boussie et al. |
| 2004/0220050 | A1* | 11/2004 | Frazier et al. ............. 502/150 |
| 2006/0135722 | A1 | 6/2006 | Boussie et al. |
| 2007/0191607 | A1 | 8/2007 | Solan et al. |
| 2010/0022726 | A1 | 1/2010 | Hagadorn et al. |

FOREIGN PATENT DOCUMENTS

| | | |
|---|---|---|
| JP | 2001-048925 | 2/2001 |
| WO | WO 2005/095469 | 10/2005 |
| WO | WO 2007/067965 | 6/2007 |

OTHER PUBLICATIONS

Froese et al., Mechanism of Activation of a Hafnium Pyridyl-Amide Olefin Polymerization Catalyst: Ligand Modification by Monomer, J. Am. Chem. Soc., 2007, vol. 129, No. 25, pp. 7831-7840.
Guérin et al., Synthesis, Structure, and Reactivity of Zirconium Alkyl Complexes Bearing Ancillary Pyridine Diamide Ligands, Organometallics, 1998, vol. 17, No. 23, pp. 5172-5177.

* cited by examiner

*Primary Examiner* — Robert D. Harlan
(74) *Attorney, Agent, or Firm* — Catherine L. Bell

(57) ABSTRACT

Pyridyldiamido transition metal complexes are disclosed for use in alkene polymerization.

26 Claims, 31 Drawing Sheets

PYRIDYLDIAMIDO TRANSITION METAL COMPLEXES, PRODUCTION AND USE THEREOF

US PRIORITY CLAIM

This application is a continuation-in part of U.S. Ser. No. 12/180,132, filed Jul. 25, 2008 now U.S. Pat. No. 7,973,116, published as US 2010/0022726 on Jan. 28, 2010).

FIELD OF INVENTION

The invention relates to pyridyldiamido transition metal complexes and intermediates and processes for use in making such pyridyldiamido complexes. The transition metal complexes may be used as catalysts for alkene polymerization processes.

BACKGROUND OF INVENTION

Pyridyl amines have been used to prepare Group 4 complexes which are useful transition metal components for use in the polymerization of alkenes, see for example US 2002/0142912; U.S. Pat. No. 6,900,321; and U.S. Pat. No. 6,103,657, where the ligands have been used in complexes in which the ligands are coordinated in a bidentate fashion to the transition metal atom.

WO 2005/095469 shows catalyst compounds that use tridentate ligands through two nitrogen atoms (one amido and one pyridyl) and one oxygen atom.

US 2004/0220050A1 and WO 2007/067965 disclose complexes in which the ligand is coordinated in a tridentate fashion through two nitrogen (one amido and one pyridyl) and one carbon (aryl anion) donors.

A key step in the activation of these complexes is the insertion of an alkene into the metal-aryl bond of the catalyst precursor (Froese, R. D. J. et al., J. Am. Chem. Soc. 2007, 129, pp. 7831-7840) to form an active catalyst that has both five-membered and a seven-membered chelate rings.

WO 2010/037059 discloses pyridine containing amines for use in pharmaceutical applications.

There still is need for adding synthetic routes to widen the range of catalysts complexes that may be prepared and broaden their performance in alkene polymerization. The performance may be varied in respect of the amount of polymer produced per amount of catalyst (generally referred to as the "activity") under the prevailing polymerization conditions; the molecular weight and molecular weight distribution achieved at a given temperature; and the placement of higher alpha-olefins in terms of the degree of stereoregular placement.

SUMMARY OF INVENTION

This invention relates to novel transition metal complexes having tridentate NNN ligands. The ligand may be derived from a neutral ligand precursor or be created in situ in a complex, as will be described. This invention also relates to a pyridyldiamido transition metal complex having the general formula (I), (II), or (III):

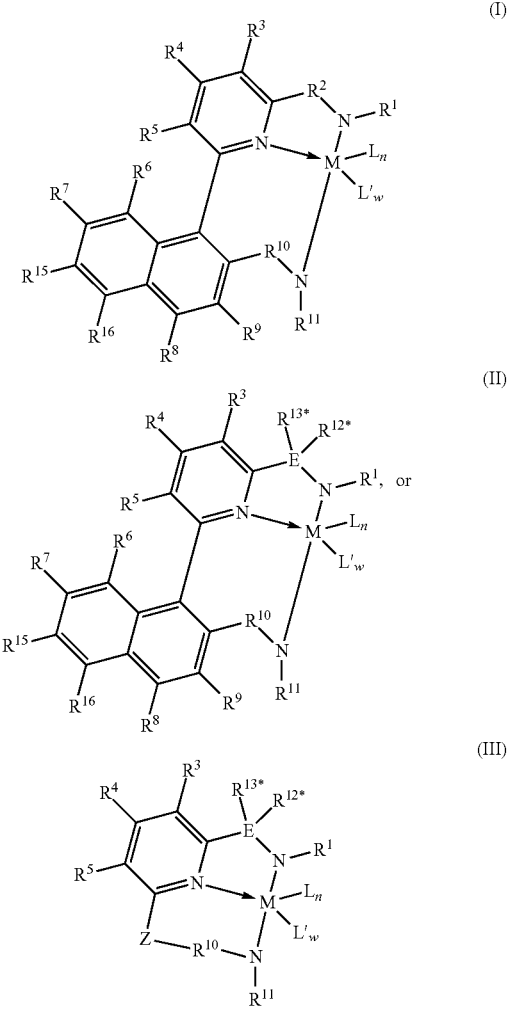

wherein:

M is a Group 3, 4, 5, 6, 7, 8, 9, 10, 11, or 12 metal;

$R^1$ and $R^{11}$ are independently selected from the group consisting of hydrocarbyls (such as alkyls, aryls), substituted hydrocarbyls (such as heteroaryls), and silyl groups;

$R^2$ and $R^{10}$ are each, independently, $-E^*(R^{12})(R^{13})-$;

E and E* are independently, carbon, silicon, or germanium;

each $R^{12}$, $R^{13}$, $R^{12*}$, and $R^{13*}$ is independently selected from the group consisting of hydrogen, hydrocarbyls (e.g., alkyl and aryl), substituted hydrocarbyls (e.g., heteroaryl), alkoxy, silyl, amino, aryloxy, halogen, and phosphino, $R^{12}$ and $R^{13}$ and/or $R^{12*}$ and $R^{13*}$ may be joined to form a saturated, substituted or unsubstituted hydrocarbyl ring, where the ring has 4, 5, 6, or 7 ring carbon atoms and where substitutions on the ring can join to form additional rings, or $R^{12}$ and $R^{13}$ and/or $R^{12*}$ and $R^{13*}$ may be joined to form a saturated heterocyclic ring, or a saturated substituted heterocyclic ring where substitutions on the ring can join to form additional rings, provided that at least one of $R^{12*}$ and $R^{13*}$ is a $C_1$ to $C_{100}$ substituted or unsubstituted hydrocarbyl group;

$R^3$, $R^4$, and $R^5$ are independently selected from the group consisting of hydrogen, hydrocarbyls (e.g., alkyls and aryls), substituted hydrocarbyls (e.g., heteroaryl), alkoxy, aryloxy, halogen, amino, and silyl, and wherein adjacent R groups ($R^3$ & $R^4$ and/or $R^4$ & $R^5$) may be joined to form a substituted or unsubstituted hydrocarbyl or heterocyclic ring, where the ring has 5, 6, 7, or 8 ring atoms and where substitutions on the ring can join to form additional rings;

$R^6$, $R^7$, $R^8$, $R^9$, $R^{15}$, and $R^{16}$ are independently selected from the group consisting of hydrogen, hydrocarbyls, substituted hydrocarbyls, alkoxy, halogen, amino, and silyl, and wherein adjacent R groups ($R^6$ & $R^7$, and/or $R^7$ & $R^{15}$, and/or $R^{16}$ & $R^{15}$, and/or $R^8$ & $R^9$) may be joined to form a saturated, substituted or unsubstituted hydrocarbyl or heterocyclic ring, where the ring has 5, 6, 7, or 8 ring carbon atoms and where substitutions on the ring can join to form additional rings;

L is an anionic leaving group, where the L groups may be the same or different and any two L groups may be linked to form a dianionic leaving group;

n is 0, 1, 2, 3, or 4;

L' is neutral Lewis base;

w is 0, 1, 2, 3, or 4;

Z is $-(R^{14*})_p Q\text{-}J(R^{15*})_q-$;

Q is C, O, N, or Si;

J is C or Si;

$R^{14*}$ and $R^{15*}$ are independently selected from the group consisting of hydrogen, hydrocarbyls, and substituted hydrocarbyls, (preferably hydrogen and alkyls), and wherein adjacent $R^{14}$ and $R^{15}$ groups may be joined to form an aromatic or saturated, substituted or unsubstituted hydrocarbyl ring, where the ring has 5, 6, 7, or 8 ring carbon atoms and where substitutions on the ring can join to form additional rings;

p is 1 or 2; and q is 1 or 2.

This invention further relates to process to make the above complex, process to make intermediates for the above complex and methods to polymerize olefins using the above complex.

BRIEF DESCRIPTION OF THE DRAWINGS

FIG. 8—500 MHz $^1$H NMR spectrum of complex A dissolved in $CD_2Cl_2$.

FIG. 9—500 MHz $^1$H NMR spectrum of complex B dissolved in $CD_2Cl_2$.

FIG. 10—500 MHz $^1$H NMR spectrum of complex C dissolved in $CD_2Cl_2$.

FIG. 11—500 MHz $^1$H NMR spectrum of complex D dissolved in $C_6D_6$.

FIG. 12—500 MHz $^1$H NMR spectrum of complex E dissolved in $CD_2Cl_2$.

FIG. 13—500 MHz $^1$H NMR spectrum of complex F dissolved in $CD_2Cl_2$.

FIG. 14—500 MHz $^1$H NMR spectrum of complex G dissolved in $CD_2Cl_2$.

FIG. 15—500 MHz $^1$H NMR spectrum of complex H dissolved in $C_6D_6$.

FIG. 16—400 MHz $^1$H NMR spectrum of complex I dissolved in $CD_2Cl_2$.

FIG. 17—500 MHz $^1$H NMR spectrum of complex J dissolved in $CD_2Cl_2$.

FIG. 18—400 MHz $^1$H NMR spectrum of complex K dissolved in $C_6D_6$.

FIG. 19—400 MHz $^1$H NMR spectrum of complex L dissolved in $C_6D_6$.

FIG. 20—500 MHz $^1$H NMR spectrum of complex M dissolved in $CD_2Cl_2$.

FIG. 21—500 MHz $^1$H NMR spectrum of complex N dissolved in $CD_2Cl_2$.

FIG. 22—400 MHz $^1$H NMR spectrum of complex O dissolved in $C_6D_6$.

FIG. 23—400 MHz $^1$H NMR spectrum of complex P dissolved in $C_6D_6$.

FIG. 24—500 MHz $^1$H NMR spectra of complex D-Me dissolved in $D_8$-toluene at 353 (top), 303, 293, 273, 251 K (bottom).

FIG. 25—500 MHz $^1$H NMR spectra of complex H-Me dissolved in $D_8$-toluene at 373 (top), 343, 310 K (bottom).

FIG. 26—500 MHz $^1$H NMR spectrum of complex Q dissolved in $CD_2Cl_2$.

FIG. 27—500 MHz $^1$H NMR spectrum of complex R dissolved in $CD_2Cl_2$.

FIG. 28—500 MHz $^1$H NMR spectrum of complex S dissolved in $CD_2Cl_2$.

FIG. 29—500 MHz $^1$H NMR spectrum of complex T dissolved in $CD_2Cl_2$.

DETAILED DESCRIPTION

Figure 1:
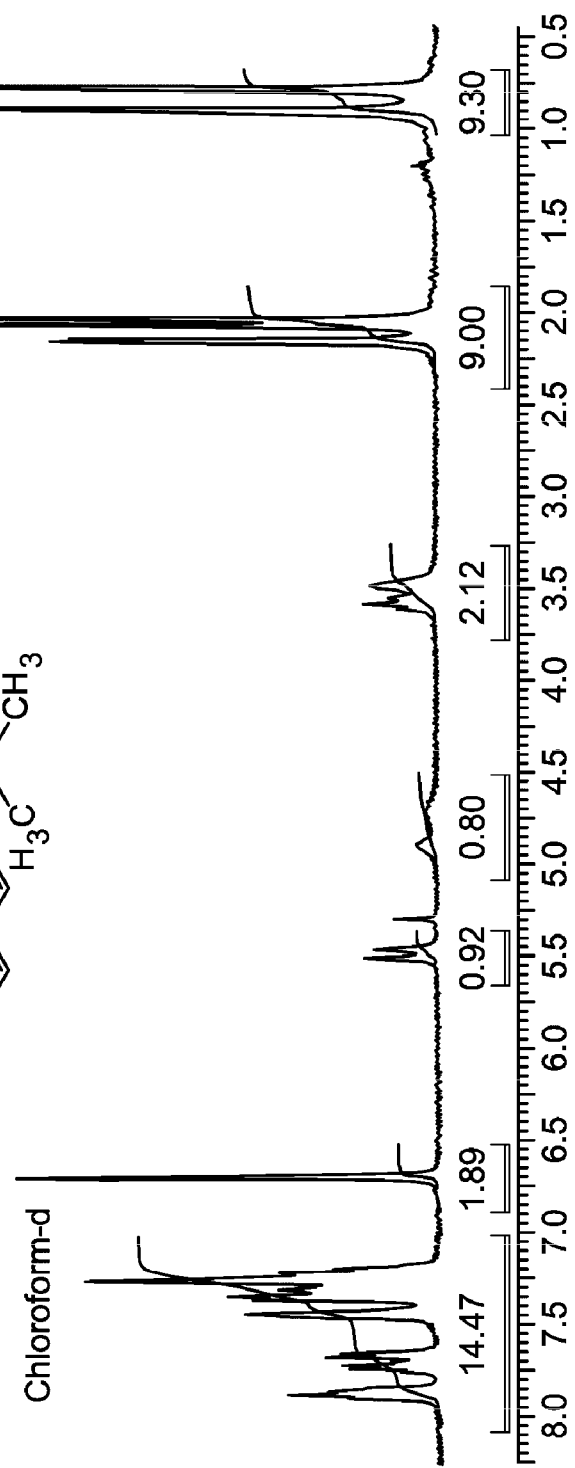
FIG. 1—$^1$H NMR spectrum of ligand 7l dissolved in $CDCl_3$.

The specification describes transition metal complexes. The term complex is used to describe molecules in which an ancillary ligand is coordinated to a central transition metal atom. The ligand is bulky and stably bonded to the transition metal so as to maintain its influence during use of the catalyst, such as polymerization. The ligand may be coordinated to the transition metal by covalent bond and/or electron donation coordination or intermediate bonds. The transition metal complexes are generally subjected to activation to perform their polymerization or oligomerization function using an activator which is believed to create a cation as a result of the removal of an anionic group, often referred to as a leaving group, from the transition metal.

As used herein, the numbering scheme for the Periodic Table groups is the new notation as set out in Chemical and Engineering News, 63(5), 27 (1985).

The following abbreviations are used through this specification: Me is methyl, Ph is phenyl, Et is ethyl, Pr is propyl, iPr is isopropyl, n-Pr is normal propyl, Bu is butyl, iBu is isobutyl, tBu is tertiary butyl, p-tBu is para-tertiary butyl, nBu is normal butyl, TMS is trimethylsilyl, TIBAL is triisobutylaluminum, TNOAL is triisobutyl n-octylaluminum, MAO is methylalumoxane, pMe is para-methyl, Ar* is 2,6-diisopropylaryl, Ph is phenyl, Bn is benzyl (i.e., CH$_2$Ph), THF (also referred to as thf) is tetrahydrofuran, RT is room temperature, tol is toluene, EtOAc is ethyl acetate, and Cy is cyclohexyl.

The term "substituted" means that a hydrogen has been replaced with a heteroatom or a hydrocarbyl group. For example, methyl-cyclopentadiene is substituted with a methyl group. The terms "hydrocarbyl radical," "hydrocarbyl" and "hydrocarbyl group" are used interchangeably throughout this document. Likewise the terms "group", "radical", and "substituent" are also used interchangeably in this document. For purposes of this disclosure, "hydrocarbyl radical" is defined to be $C_1$-$C_{100}$ radicals, that may be linear, branched, or cyclic, and when cyclic, aromatic or non-aromatic.

Substituted hydrocarbyl radicals are radicals in which at least one hydrogen atom of the hydrocarbyl radical has been substituted with at least one functional group such as NR*$_2$, OR*, SeR*, TeR*, PR*$_2$, AsR*$_2$, SbR*$_2$, SR*, BR*$_2$, SiR*$_3$, GeR*$_3$, SnR*$_3$, PbR*$_3$, and the like, or where at least one heteroatom has been inserted within a hydrocarbyl ring.

The term "catalyst system" is defined to mean a complex/activator pair. When "catalyst system" is used to describe such a pair before activation, it means the unactivated catalyst complex (precatalyst) together with an activator and, optionally, a co-activator. When it is used to describe such a pair after activation, it means the activated complex and the activator or other charge-balancing moiety. The transition metal compound may be neutral as in a precatalyst, or a charged species with a counter ion as in an activated catalyst system.

Complex, as used herein, is also often referred to as catalyst precursor, precatalyst, catalyst, catalyst compound, transition metal compound, or transition metal complex. These words are used interchangeably. Activator and cocatalyst are also used interchangeably.

A scavenger is a compound that is typically added to facilitate polymerization by scavenging impurities. Some scavengers may also act as activators and may be referred to as co-activators. A co-activator, that is not a scavenger, may also be used in conjunction with an activator in order to form an active catalyst. In some embodiments a co-activator can be pre-mixed with the transition metal compound to form an alkylated transition metal compound.

Noncoordinating anion (NCA) is defined to mean an anion either that does not coordinate to the catalyst metal cation or that does coordinate to the metal cation, but only weakly. The term NCA is also defined to include multicomponent NCA-containing activators, such as N,N-dimethylanilinium tetrakis(pentafluorophenyl)borate, that contain an acidic cationic group and the non-coordinating anion. The term NCA is also defined to include neutral Lewis acids, such as tris(pentafluorophenyl)boron, that can react with a catalyst to form an activated species by abstraction of an anionic group. An NCA coordinates weakly enough that a neutral Lewis base, such as an olefinically or acetylenically unsaturated monomer can displace it from the catalyst center.

Any metal or metalloid that can form a compatible, weakly coordinating complex may be used or contained in the non-coordinating anion. Suitable metals include, but are not limited to, aluminum, gold, and platinum. Suitable metalloids include, but are not limited to, boron, aluminum, phosphorus, and silicon. A stoichiometric activator can be either neutral or ionic. The terms ionic activator, and stoichiometric ionic activator can be used interchangeably. Likewise, the terms neutral stoichiometric activator, and Lewis acid activator can be used interchangeably. The term non-coordinating anion includes neutral stoichiometric activators, ionic stoichiometric activators, ionic activators, and Lewis acid activators.

When a polymer or oligomer is referred to as comprising an olefin, the olefin present in the polymer or oligomer is the polymerized or oligomerized form of the olefin. An oligomer is defined to be compositions having 2-50 monomer units. A polymer is defined to be compositions having 51 or more monomer units.

A higher α-olefin is defined to be an α-olefin having 4 or more carbon atoms.

Unless otherwise noted, all molecular weights units (e.g., Mw, Mn, Mz) are g/mol.

Unless otherwise noted all melting points ($T_m$) are DSC second melt.

A "ring carbon atom" is a carbon atom that is part of a cyclic ring structure. By this definition, a benzyl group has six ring carbon atoms and para-methylstyrene also has six ring carbon atoms.

The term "aryl" or "aryl group" means a six carbon aromatic ring and the substituted variants thereof, including but not limited to, phenyl, 2-methyl-phenyl, xylyl, 4-bromo-xylyl. Likewise heteroaryl means an aryl group where a ring carbon atom (or two or thee ring carbon atoms) has been replaced with a heteroatom, preferably N, O, or S.

The term "ring atom" means an atom that is part of a cyclic ring structure. By this definition, a benzyl group has six ring atoms and tetrahydrofuran has 5 ring atoms.

A heterocyclic ring is a ring having a heteroatom in the ring structure as opposed to a heteroatom substituted ring where a hydrogen on a ring atom is replaced with a heteroatom. For example, tetrahydrofuran is a heterocyclic ring and 4-N,N-dimethylamino-phenyl is a heteroatom substituted ring.

As used herein, the term "aromatic" also refers to pseudoaromatic heterocycles which are heterocyclic substituents that have similar properties and structures (nearly planar) to aromatic heterocyclic ligands, but are not by definition aromatic; likewise the term aromatic also refers to substituted aromatics.

The term "continuous" means a system that operates without interruption or cessation. For example a continuous process to produce a polymer would be one where the reactants are continually introduced into one or more reactors and polymer product is continually withdrawn.

A solution polymerization means a polymerization process in which the polymer is dissolved in a liquid polymerization medium, such as an inert solvent or monomer(s) or their blends. A solution polymerization is typically homogeneous. A homogeneous polymerization is one where the polymer product is dissolved in the polymerization medium. Such systems are preferably not turbid as described in J. Vladimir Oliveira, C. Dariva and J. C. Pinto, Ind. Eng, Chem. Res. 29, 2000, 4627.

A bulk polymerization means a polymerization process in which the monomers and/or comonomers being polymerized are used as a solvent or diluent using little or no inert solvent as a solvent or diluent. A small faction of inert solvent might be used as a carrier for catalyst and scavenger. A bulk polymerization system contains less than 25 wt % of inert solvent or diluent, preferably less than 10 wt %, preferably less than 1 wt %, preferably 0 wt %.

In a first aspect of the invention, there is provided a pyridyldiamido transition metal complex (optionally, for use in alkene polymerization) having the general formula: (I), (II), or (III):

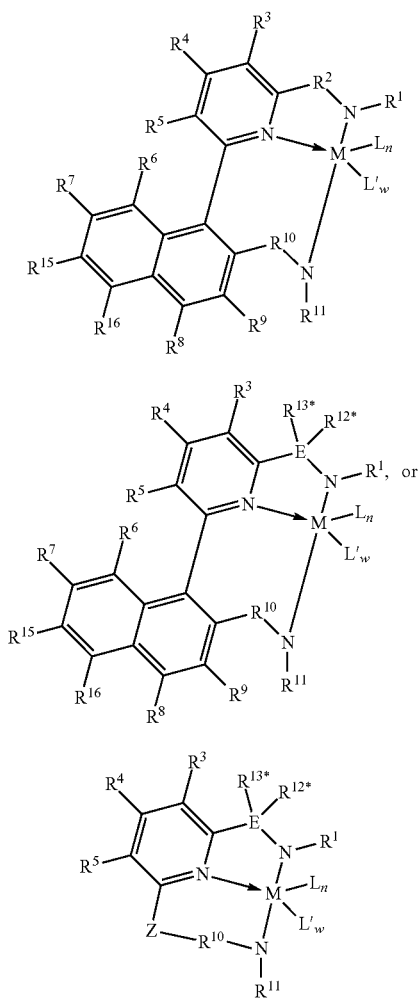

wherein:

M is a Group 3, 4, 5, 6, 7, 8, 9, 10, 11, or 12 metal (preferably a Group 4 metal, preferably Ti, Zr or Hf);

$R^1$ and $R^{11}$ are independently selected from the group consisting of hydrocarbyls, substituted hydrocarbyls, and silyl groups (preferably alkyl, aryl, heteroaryl, and silyl groups);

$R^2$ and $R^{10}$ are each, independently, $-E^*(R^{12})(R^{13})-$ (preferably RIO is $CH_2$, preferably $R^{12}$, and $R^{13}$ are the same);

E and E* are, independently, carbon, silicon, or germanium (preferably carbon or silicon, preferably carbon);

each $R^{12}$, $R^{13}$, $R^{12*}$, and $R^{13*}$ is independently selected from the group consisting of hydrogen, hydrocarbyl, and substituted hydrocarbyl, alkoxy, silyl, amino, aryloxy, halogen, and phosphino (preferably hydrogen, alkyl, aryl, alkoxy, silyl, amino, aryloxy, heteroaryl, halogen, and phosphino), $R^{12}$ and $R^{13}$ and/or $R^{12*}$ and $R^{13*}$ may be joined to form a saturated, substituted or unsubstituted hydrocarbyl ring, where the ring has 4, 5, 6, or 7 ring carbon atoms and where substitutions on the ring can join to form additional rings, or $R^{12}$ and $R^{13}$ and/or $R^{12*}$ and $R^{13*}$ may be joined to form a saturated heterocyclic ring, or a saturated substituted heterocyclic ring where substitutions on the ring can join to form additional rings, provided that at least one of $R^{12*}$ and $R^{13*}$ is a $C_1$ to $C_{100}$ (preferably $C_6$ to Co, preferably $C_7$ to $C_{30}$, preferably $C_8$ to $C_{20}$) substituted or unsubstituted hydrocarbyl group (preferably aryl, phenyl, substituted phenyl, alkyl or aryl substituted phenyl, $C_2$ to $C_{30}$ alkyl or aryl substituted phenyl, 2-substituted phenyl, 2-isopropylphenyl, 2,4,6-trimethylphenyl, and the like);

$R^3$, $R^4$, and $R^5$ are independently selected from the group consisting of hydrogen, hydrocarbyls, substituted hydrocarbyls, alkoxy, aryloxy, halogen, amino, and silyl, (preferably hydrogen, alkyl, alkoxy, aryloxy, halogen, amino, silyl, and aryl), and wherein adjacent R groups ($R^3$ & $R^4$ and/or $R^4$ & $R^5$) may be joined to form a substituted or unsubstituted hydrocarbyl or heterocyclic ring, where the ring has 5, 6, 7, or 8 ring atoms and where substitutions on the ring can join to form additional rings;

$R^6$, $R^7$, $R^8$, $R^9$, $R^{15}$, and $R^{16}$ are independently selected from the group consisting of hydrogen, hydrocarbyls, substituted hydrocarbyls, alkoxy, halogen, amino, and silyl, and the pairs of positions, and wherein adjacent R groups ($R^6$ & $R^7$, and/or $R^7$ & $R^{15}$, and/or $R^{16}$ & $R^{15}$, and/or $R^8$ & $R^9$) may be joined to form a saturated, substituted or unsubstituted hydrocarbyl or heterocyclic ring, where the ring has 5, 6, 7, or 8 ring carbon atoms and where substitutions on the ring can join to form additional rings;

L is an anionic leaving group, where the L groups may be the same or different and any two L groups may be linked to form a dianionic leaving group;

n is 0, 1, 2, 3, or 4;

L' is neutral Lewis base;

w is 0, 1, 2; 3, or 4;

Z is $-(R^{14*})_p Q\text{-}J(R^{15*})_q-$ where Q or J is bonded to $R^{10}$;

J is C or Si, preferably C;

Q is C, O, N, or Si, preferably C (preferably both J and Q are C);

$R^{14*}$ and $R^{15*}$ are independently selected from the group consisting of hydrogen, hydrocarbyls, and substituted hydrocarbyls, (preferably hydrogen and alkyls), and wherein adjacent $R^{14*}$ and $R^{15*}$ groups may be joined to form an aromatic or saturated, substituted or unsubstituted hydrocarbyl ring, where the ring has 5, 6, 7, or 8 ring carbon atoms and where substitutions on the ring can join to form additional rings;

p is 1 or 2; and q is 1 or 2.

Preferably the R groups above and other R groups mentioned hereafter, contain up to 30 carbon atoms, preferably no more than 30 carbon atoms, especially from 2 to 20 carbon atoms.

Preferably M is Ti, Zr, or Hf and/or E and/or E* is carbon, with Zr or Hf based complexes being especially preferred.

In a preferred embodiment, $R_1$ and $R_{11}$ may be independently selected from phenyl groups that are variously substituted with between zero to five substituents that include F, Cl, Br, I, $CF_3$, $NO_2$, alkoxy, dialkylamino, aryl, and alkyl groups with between one to ten carbons.

In a preferred embodiment, each L may be independently selected from halide, alkyl, aryl, alkoxy, amido, hydrido, phenoxy, hydroxy, silyl, allyl, alkenyl, triflate, alkylsulfonate, arylsulfonate, and alkynyl. The selection of the leaving groups depends on the synthesis route adopted for arriving at the complex and may be changed by additional reactions to suit the later activation method in polymerization. For example, alkyl is preferred when using non-coordinating anions such as N,N-dimethylanilinium tetrakis(pentafluorophenyl)-borate or tris(pentafluorophenyl)borane. In another embodiment, two L groups may be linked to form a dianionic leaving group, for example, oxalate.

In another embodiment, each L' is independently selected from the group consisting of ethers, thio-ethers, amines, nitriles, imines, pyridines, and phosphines, preferably ethers.

In any embodiment described herein, M is preferably a Group 4 metal, preferably Zr or Hf.

In any embodiment described herein, E and or E* is preferably carbon.

In any embodiment described herein, one of $R^{12*}$ and $R^{13*}$ is preferably hydrogen. In any embodiment described herein, $R^{12*}$ and $R^{13*}$ are not benzyl.

In any embodiment described herein, $R^{10}$ is $CH_2$. In any embodiment described herein, preferably $R^{12}$ and $R^{13}$ are the same.

In any embodiment described herein, $R^2$ and $R^{10}$ are each, independently, represented by the formula:

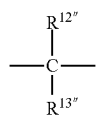

In any embodiment described herein, $R^{12''}$ is hydrogen, alkyl, aryl, or halogen; and $R^{13''}$ is hydrogen, alkyl, aryl, or halogen, preferably $R^{12''}$ and $R^{13''}$ are the same.

Preferably, in any embodiment described herein, $R^{12*}$ and $R^{13*}$ are the same.

In any embodiment described herein, $R^6$, $R^7$, $R^8$, $R^9$, $R^{15}$, and $R^{16}$ may be, independently, selected from the group consisting of hydrogen, hydrocarbyls, substituted hydrocarbyls, alkoxy, halogen, amino, and silyl.

In any embodiment described herein, $R^1$, $R^3$, $R^4$, $R^5$, and $R^{11}$ may each contain no more than 30 carbon atoms, preferably $R^1$, $R^3$, $R^4$, $R^5$, $R^6$, $R^7$, $R^8$, $R^9$, and $R^{15}$ each contain no more than 30 carbon atoms.

In any embodiment described herein, E is carbon and $R^1$ and $R^{11}$ are independently selected from phenyl groups that are substituted with 0, 1, 2, 3, 4, or 5 substituents selected from the group consisting of F, Cl, Br, I, $CF_3$, $NO_2$, alkoxy, dialkylamino, hydrocarbyl, and substituted hydrocarbyls groups with from one to ten carbons.

In a preferred embodiment, the pyridyldiamido transition metal complex is represented by the Formula (III) above and at least one of $R^{12*}$ and $R^{13*}$ is a group containing from 1 to 100 (preferably 6 to 40, preferably 7 to 30) carbons.

In a preferred embodiment, the pyridyldiamido transition metal complex is represented by the Formula (III) above, $R^{12}$ is H, $R^{13}$ is a group containing between 1 to 100 (preferably 6 to 40, preferably 7 to 30) carbons, M is a Group 4 metal, preferably Zr or Hf, E is carbon, $R^{12''}$ and $R^{13''}$ are the same, preferably $R^{10}$ is $CH_2$.

In a preferred embodiment, the pyridyldiamido transition metal complex is represented by the Formula (I) above, and M is a Group 4 metal preferably Zr or Hf, preferably Hf.

In a preferred embodiment, the pyridyldiamido transition metal complex is represented by the Formula (II) above, and M is a Group 4 metal preferably Zr or Hf, preferably Hf.

In a preferred embodiment, the pyridyldiamido transition metal complex is represented by the Formula (II) above, and $R^{10}$ is $CH_2$.

In a preferred embodiment, the pyridyldiamido transition metal complex is represented by the Formula (II) above, $R^{12*}$ is H, $R^{13*}$ is a group containing between 1 to 100 (preferably 6 to 40, preferably 7 to 30) carbons, M is a Group 4 metal (preferably Zr or Hf, preferably Hf), E is carbon and $R^{10}$ is $CH_2$.

In a preferred embodiment, the pyridyldiamido transition metal complex is represented by the Formula (I) and both $R^{12}$ and $R^{13}$ in $R^2$ are a $C_1$ to $C_{100}$ alkyl group (preferably a $C_6$ to $C_o$ alkyl group, preferably $C_7$ to $C_{30}$ alkyl group, alternately a $C_1$ to $C_{12}$ alkyl group, alternately a $C_1$ to $C_6$ alkyl group, alternately methyl, ethyl, propyl, butyl, pentyl hexyl, octyl, nonyl, decyl, or an isomer thereof).

In another preferred embodiment, the pyridyldiamido transition metal complex is represented by the Formula (I) and at least one of $R^{10}$ and $R^2$ is $CH_2$ and in the other at least one of $R^{12}$ and $R^{13}$ is a $C_1$ to $C_{100}$ alkyl group, preferably both are the same or different $C_1$ to $C_{100}$ alkyl group (preferably a $C_6$ to $C_{40}$ alkyl group, preferably $C_7$ to $C_{30}$ alkyl group, alternately a $C_1$ to $C_{12}$ alkyl group, alternately a $C_1$ to $C_6$ alkyl group, alternately methyl, ethyl, propyl, butyl, pentyl hexyl, octyl, nonyl, decyl, or an isomer thereof).

In another preferred embodiment, the pyridyldiamido transition metal complex is represented by the Formula (II) or (III) and $R^{10}$ is $CH_2$ and at least one of $R^{12*}$ and $R^{13*}$ is a $C_1$ to $C_{100}$ alkyl group, preferably both are the same or different $C_1$ to $C_{100}$ alkyl group (preferably a $C_6$ to $C_{40}$ alkyl group, preferably $C_7$ to $C_{30}$ alkyl group, alternately a $C_1$ to $C_{12}$ alkyl group, alternately a $C_1$ to $C_6$ alkyl group, alternately methyl, ethyl, propyl, butyl, pentyl hexyl, octyl, nonyl, decyl, or an isomer thereof).

In another preferred embodiment, the pyridyldiamido transition metal complex is represented by the Formula (II) or (III) and $R^{12*}$ and $R^{13*}$ are hydrogen, E is C, and E* is C or Si and at least one of $R^{12}$ and $R^{13}$ is a $C_1$ to $C_{100}$ alkyl group, preferably both $R^{12}$ and $R^{13}$ are a same or different $C_1$ to $C_{100}$ alkyl group (preferably a $C_6$ to $C_o$ alkyl group, preferably $C_7$ to $C_{30}$ alkyl group, alternately a $C_1$ to $C_{12}$ alkyl group, alternately a $C_1$ to $C_6$ alkyl group, alternately methyl, ethyl, propyl, butyl, pentyl hexyl, octyl, nonyl, decyl, or an isomer thereof).

In a preferred embodiment of formula (I), at least one of $R^2$ and $R^{10}$ is $CH_2$ and the other is substituted.

Additional preferred embodiments include the following structures:

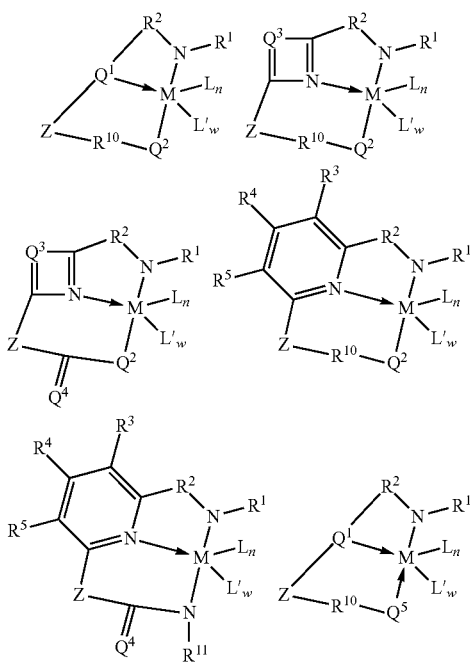

-continued

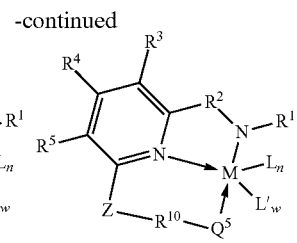

M is a Group 3, 4, 5, 6, 7, 8, 9, 10, 11, or 12 metal, preferably a Group 4 metal, preferably Hf or Zr;

Z is —$(R^{14*})_p QJ(R^{15*})_q$— and either Q or J is bonded to $R^{10}$;

J is C or Si, preferably C;

where Q is C, O, N, or Si, preferably C (preferably both J and Q are C);

$R^{14*}$ and $R^{15*}$ are independently selected from the group consisting of hydrogen, hydrocarbyls (preferably alkyls), and substituted hydrocarbyls, and wherein adjacent $R^{14*}$ and $R^{15*}$ groups may be joined to form an aromatic or saturated, substituted or unsubstituted hydrocarbyl ring, where the ring has 5, 6, 7, or 8 ring carbon atoms and where substitutions on the ring can join to form additional rings ($R^{14*}$ and $R^{15*}$ may, independently, be any preferred embodiment described above for $R^{14}$ in Formula (I) (II) or (III) above);

p is 1 or 2;

q is 1 or 2;

$R^1$, $R^{11}$, $R^{17}$, $R^{18}$, $R^{19}$, and $R^{20}$ are independently selected from the group consisting of hydrocarbyls (such as alkyls, aryls), substituted hydrocarbyls (such as heteroaryls), and silyl groups ($R^1$, $R^{11}$, $R^{17}$, $R^{18}$, $R^{19}$, and $R^{20}$ may, independently, be any preferred embodiment described above for $R^1$ in Formula (I), (II), or (III) above);

$R^2$ and $R^{10}$ are each, independently, -$E(R^{12})(R^{13})$—;

E is carbon, silicon, or germanium (preferably carbon), and each $R^{12}$ and $R^{13}$ being independently selected from the group consisting of hydrogen, hydrocarbyls (e.g., alkyl and aryl), substituted hydrocarbyls (e.g., heteroaryl), alkoxy, silyl, amino, aryloxy, halogen, and phosphino, $R^{12}$ and $R^{13}$ may be joined to form a saturated, substituted or unsubstituted hydrocarbyl ring, where the ring has 4, 5, 6, or 7 ring carbon atoms and where substitutions on the ring can join to form additional rings, or $R^{12}$ and $R^{13}$ may be joined to form a saturated heterocyclic ring, or a saturated substituted heterocyclic ring where substitutions on the ring can join to form additional rings ($R^{12}$ and $R^{13}$ may, independently, be any preferred embodiment described above for $R^{12}$ in Formula (I), (II), or (III) above);

$R^3$, $R^4$, and $R^5$ are independently selected from the group consisting of hydrogen, hydrocarbyls (e.g., alkyls and aryls), substituted hydrocarbyls (e.g., heteroaryl), alkoxy, aryloxy, halogen, amino, and silyl, and wherein adjacent R groups ($R^3$ & $R^4$ and for $R^4$ & $R^5$) may be joined to form a substituted or unsubstituted hydrocarbyl or heterocyclic ring, where the ring has 5, 6, 7, or 8 ring atoms and where substitutions on the ring can join to form additional rings ($R^3$, $R^4$, and $R^5$ may, independently, be any preferred embodiment described above for $R^3$ in Formula (I), (II), or (III) above);

L is an anionic leaving group, where the L groups may be the same or different and any two L groups may be linked to form a dianionic leaving group (L may, independently, be any preferred embodiment described above for L in Formula (I), (II), or (III) above);

n is 0, 1, 2, 3, or 4;

L' is neutral Lewis base (L' may, independently, be any preferred embodiment described above for L' in Formula (I), (II), or (III) above);

w is 0, 1, 2, 3, or 4;

$Q^1$ is a group that links $R^2$ and Z by a three atom bridge with one of the three atoms being a group 15 or 16 element that preferably forms a dative bond to M;

$Q^2$ is a group that forms an anionic bond with M, including but not limited to a group 16 element or $NR^{17}$ or $PR^{17}$;

$Q^3$ is -(TT)- or -(TTT)- (where each T is carbon or a heteroatom, preferably C, O, S, or N, and said carbon or heteroatom may be substituted or unsubstituted) that together with the "—C—N═C—" fragment, forms a 5- or 6-membered cyclic group or a polycyclic group including the 5 or 6 membered cyclic group;

$Q^4$ is a Group 16 element, $NR^{18}$, or $PR^{18}$; and $Q^5$ is a group that forms a dative bond with M, including but not limited to $OR^{19}$, $N(R^{19})(R^{20})$, or $N(R^{19})(R^{20})$.

In another aspect of the invention, there are provided various processes for synthesizing the complexes described herein.

The pyridyl diamine ligands described herein are generally prepared in multiple steps. One step involves the preparation of an amine-containing "linker" group where the linker is typically a boronic acid ester of an aryl methyl amine or substituted amine. This amine-containing linker may be prepared from an aryl-methyl boronic ester in two steps, the first of which involves the conversion of the methyl group to a halo-methyl group by free radical halogenation in unreactive solvents (e.g., $CCl_4$, benzene). The second step then involves reaction of this halo-methyl group containing species with an amine or protected amine or deprotonated protected amine to yield an amine-containing linker. This amine-containing linker is then coupled with a suitable pyridine containing species, such as 6-bromo-2-pyridinecarboxaldehyde. This coupling step typically uses a metal catalyst (e.g., $Pd(PPh_3)_4$) in less than 5 mol % loading. Following this coupling step, the new derivative, which can be described as amine-linker-pyridine-aldehyde, is then reacted with a second amine to produce the imine derivative amine-linker-pyridine-imine in a condensation reaction. This can then be reduced to the pyridyl diamine ligand by reaction with a suitable aryl anion, alkyl anion, or hydride source. This reaction is generally performed in etherial solvents at temperatures between –100° C. and 50° C. when aryllithium or alkyllithium reagents are employed. This reaction is generally performed in methanol at reflux when sodium cyanoborohydride is employed.

The preparation of pyridyl diamide metal complexes from pyridyl diamines may be accomplished using typical protonolysis and methylation reactions. In the protonolysis reaction the pyridyl diamine is reacted with a suitable metal reactant to produce a pyridyldiamide metal complex. A suitable metal reactant will feature a basic leaving group that will accept a proton from the pyridiyl diamine and then generally depart and be removed from the product. Suitable metal reactants include, but are not limited to, $HfBn_4$ ($Bn=CH_2Ph$), $ZrBn_4$, $TiBn_4$, $ZrBn_2Cl_2(OEt_2)$, $HfBn_2Cl_2(OEt_2)_2$, $Zr(NMe_2)_2Cl_2$(dimethoxyethane), $Hf(NMe_2)_2Cl_2$ (dimethoxyethane), $Hf(NMe_2)_4$, and $Hf(NEt_2)_4$. Pyridyldiamide metal complexes that contain metal-chloride groups, such as the PDA dichloride complex in Scheme 1 below, can be alkylated by reaction with an appropriate organometallic reagent. Suitable reagents include organolithium and organomagnesium, and Grignard reagents. The alkylations are generally performed in etherial or hydrocarbon solvents or solvent mixtures at temperatures typically ranging from –100° C. to 50° C.

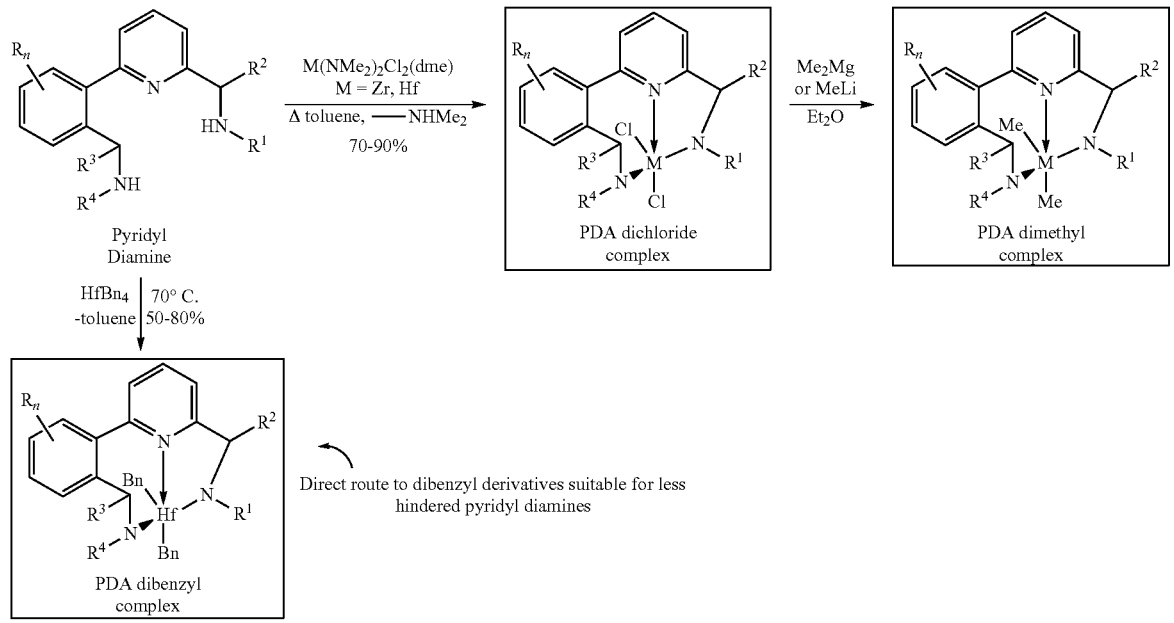

Scheme 1 where in Scheme 1, R, $R^1$, $R^2$, $R^3$, $R^4$ are independently selected from the group consisting of H, hydrocarbyls (such as alkyls, aryls), substituted hydrocarbyls (such as heteroaryls), and silyl groups, and $R_n$ indicates hydrogen, hydrocarbyls, or substituted hydrocarbyls, which may be joined to form polycyclic aromatic ring and n is 1, 2, 3, or 4.

Another route to pyridyl diamide and other complexes of interest as catalysts involves the insertion of an unsaturated molecule into a covalent metal-carbon bond where the covalently bonded group is part of a multidentate ligand structure, such as that described by Boussie et al. in U.S. Pat. No. 6,750,345. The unsaturated molecule will generally have a carbon-X double or triple bond where X is a group 14 or group 15 or group 16 element. Examples of unsaturated molecules include alkenes, alkynes, imines, nitriles, ketones, aldehydes, amides, formamides, carbon dioxide, isocyanates, thioisocyanates, and carbodiimides. Examples showing the insertion reactions involving benzophenone and N,N-dimethylformamide are below.

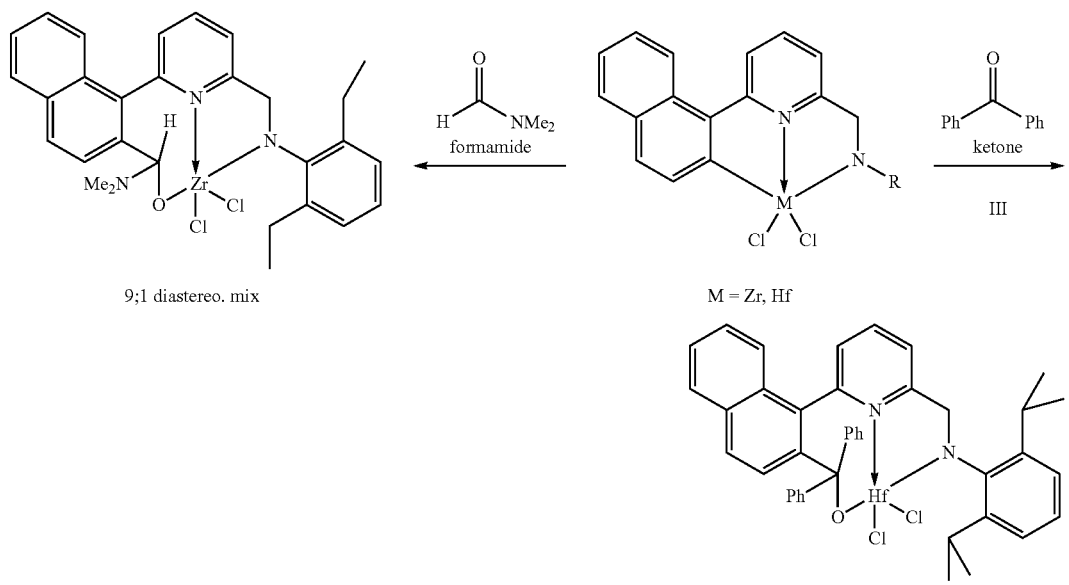

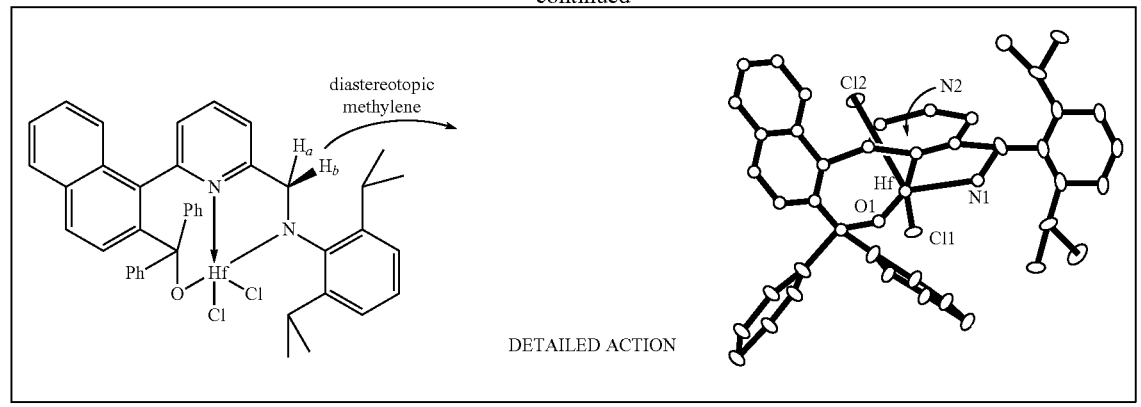

Figure 24:
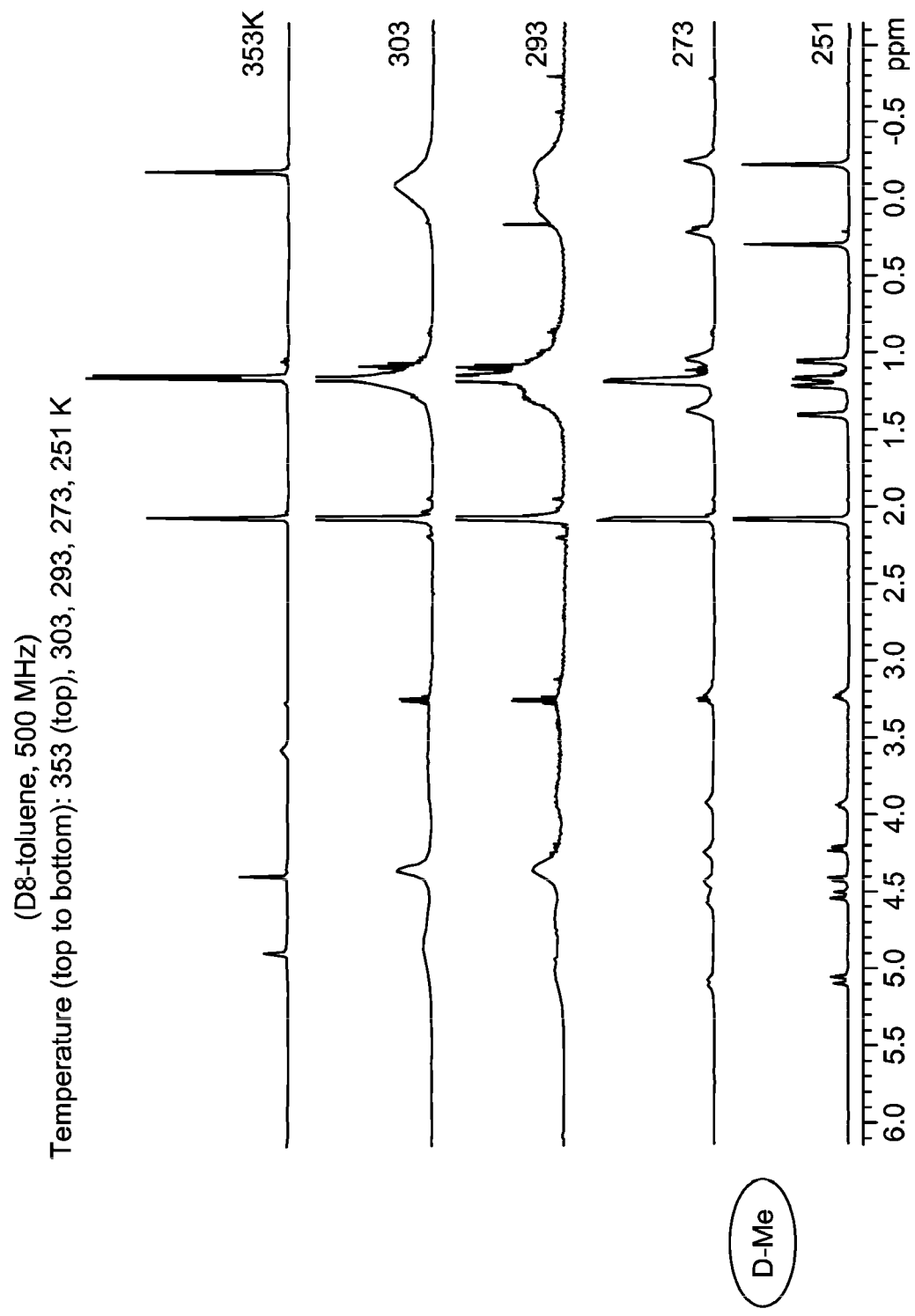
Figure 25:
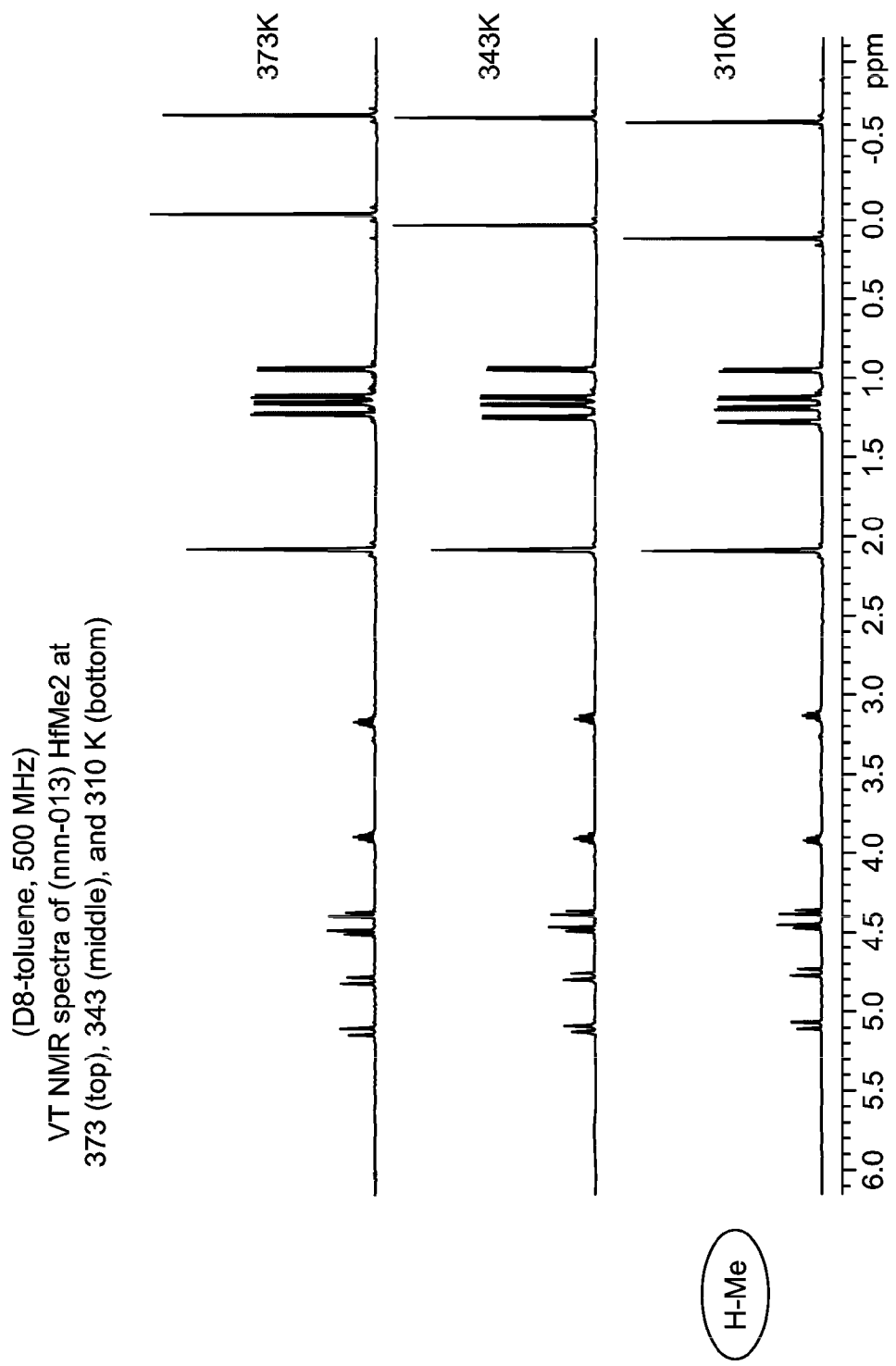
Figure 26:
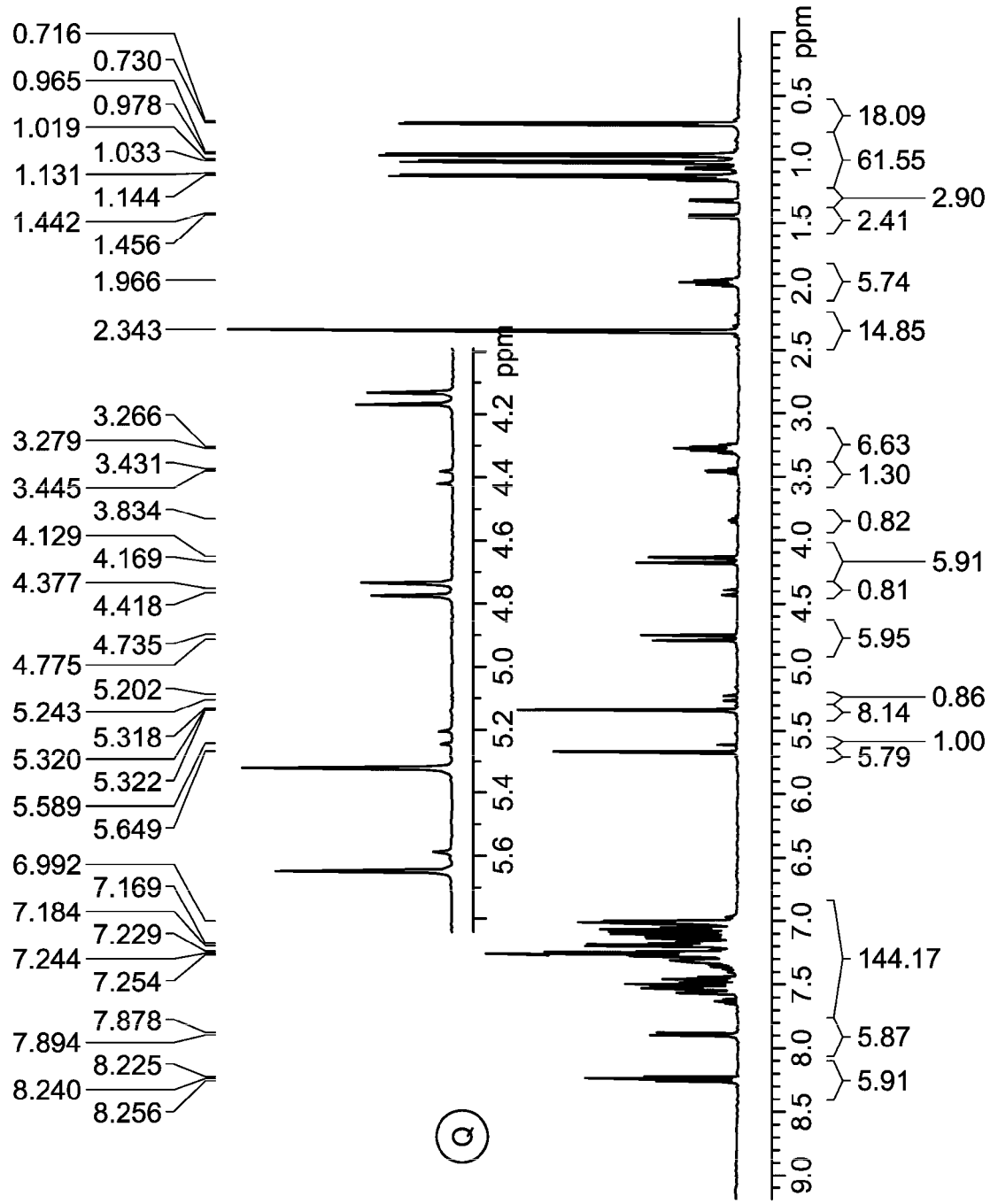
Figure 27:
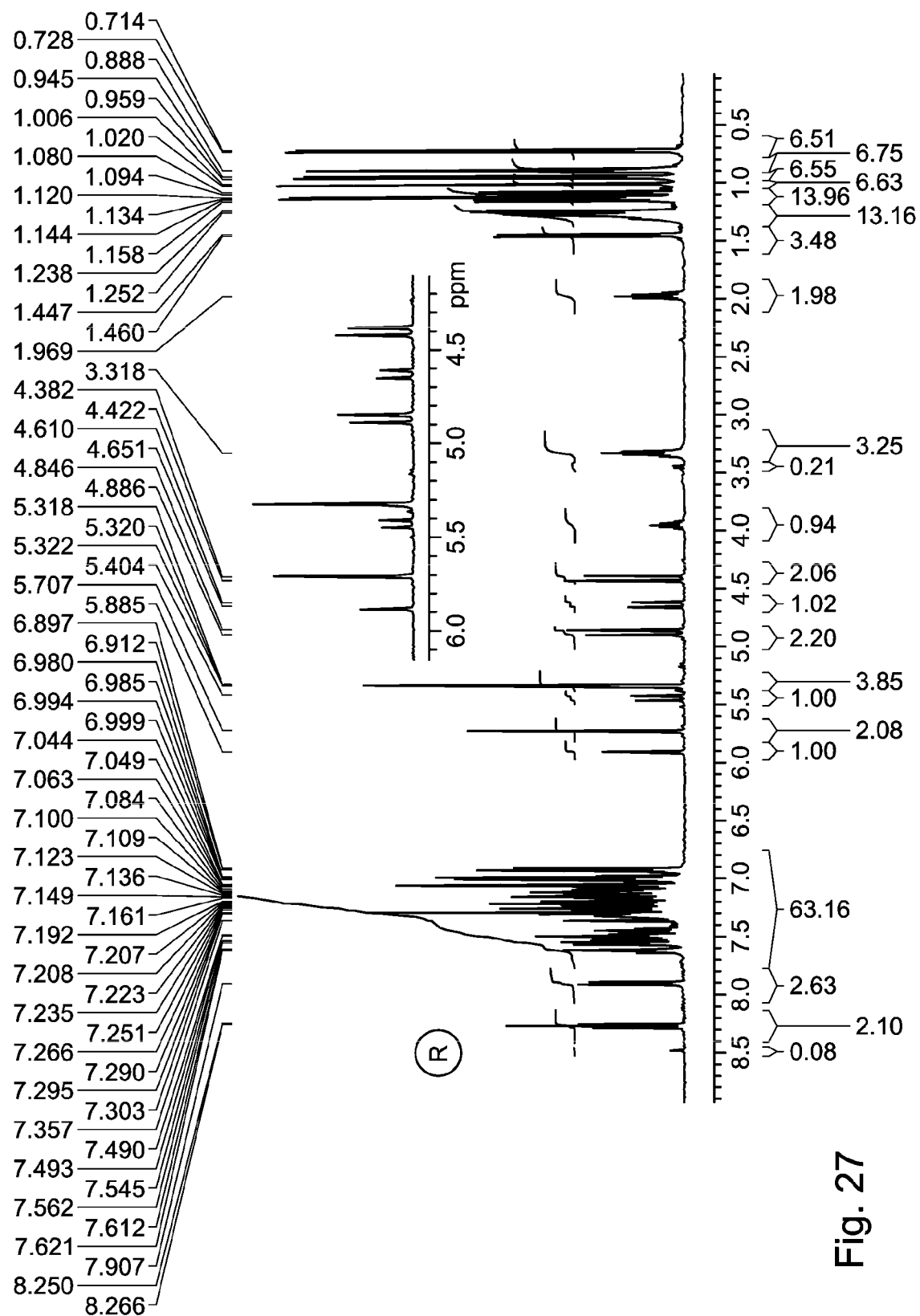
Figure 28:
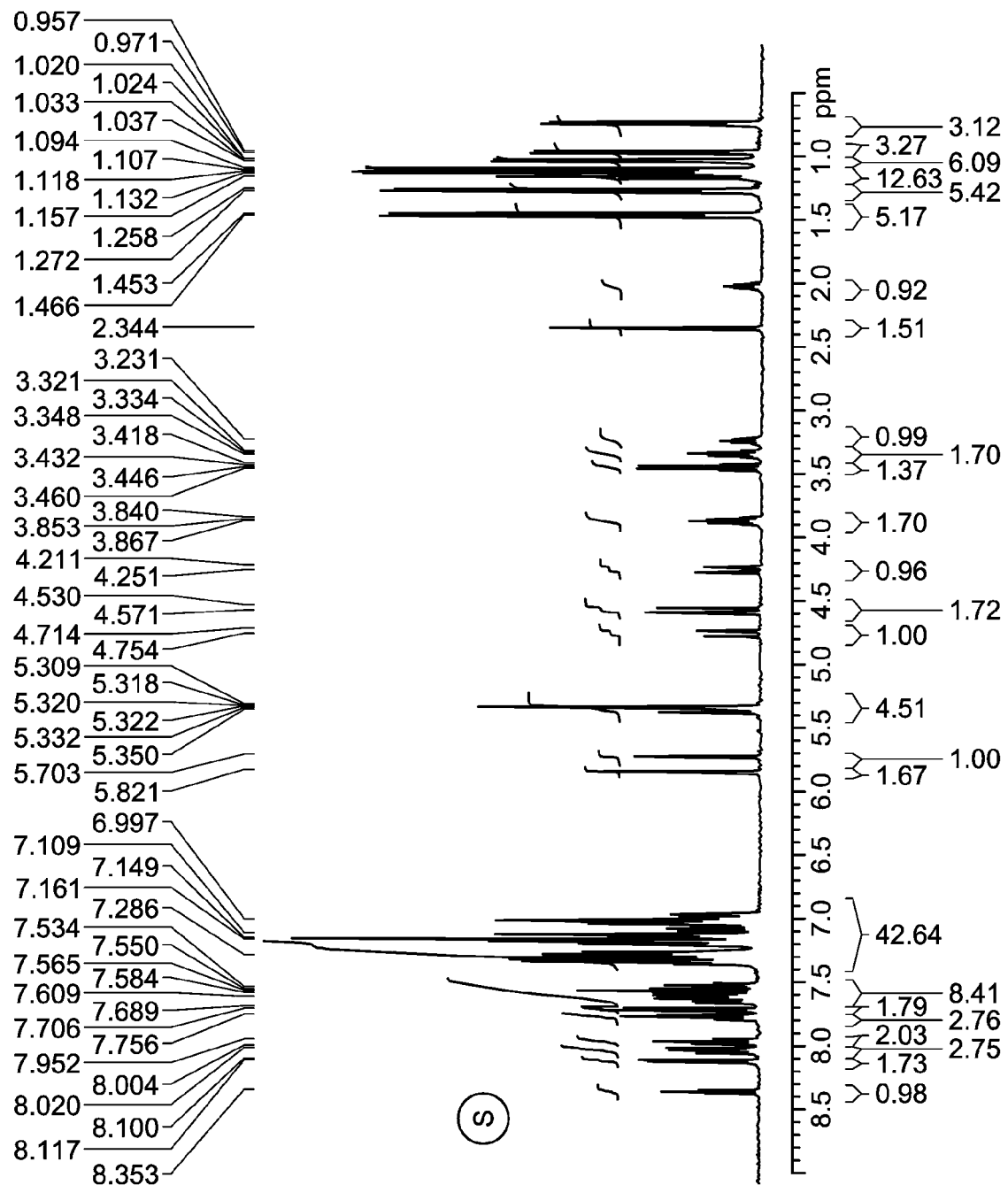
Figure 29:
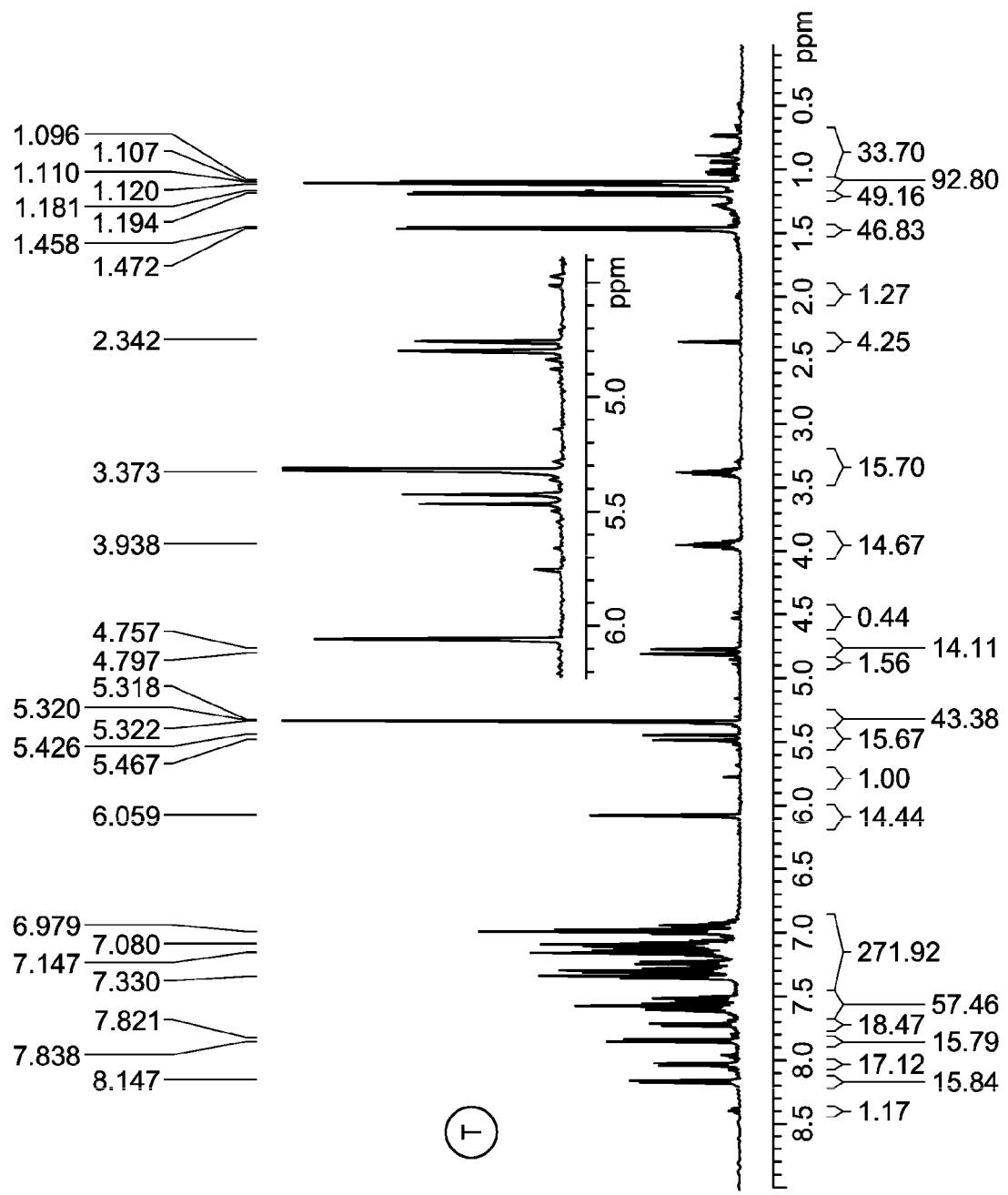
Figure 30:
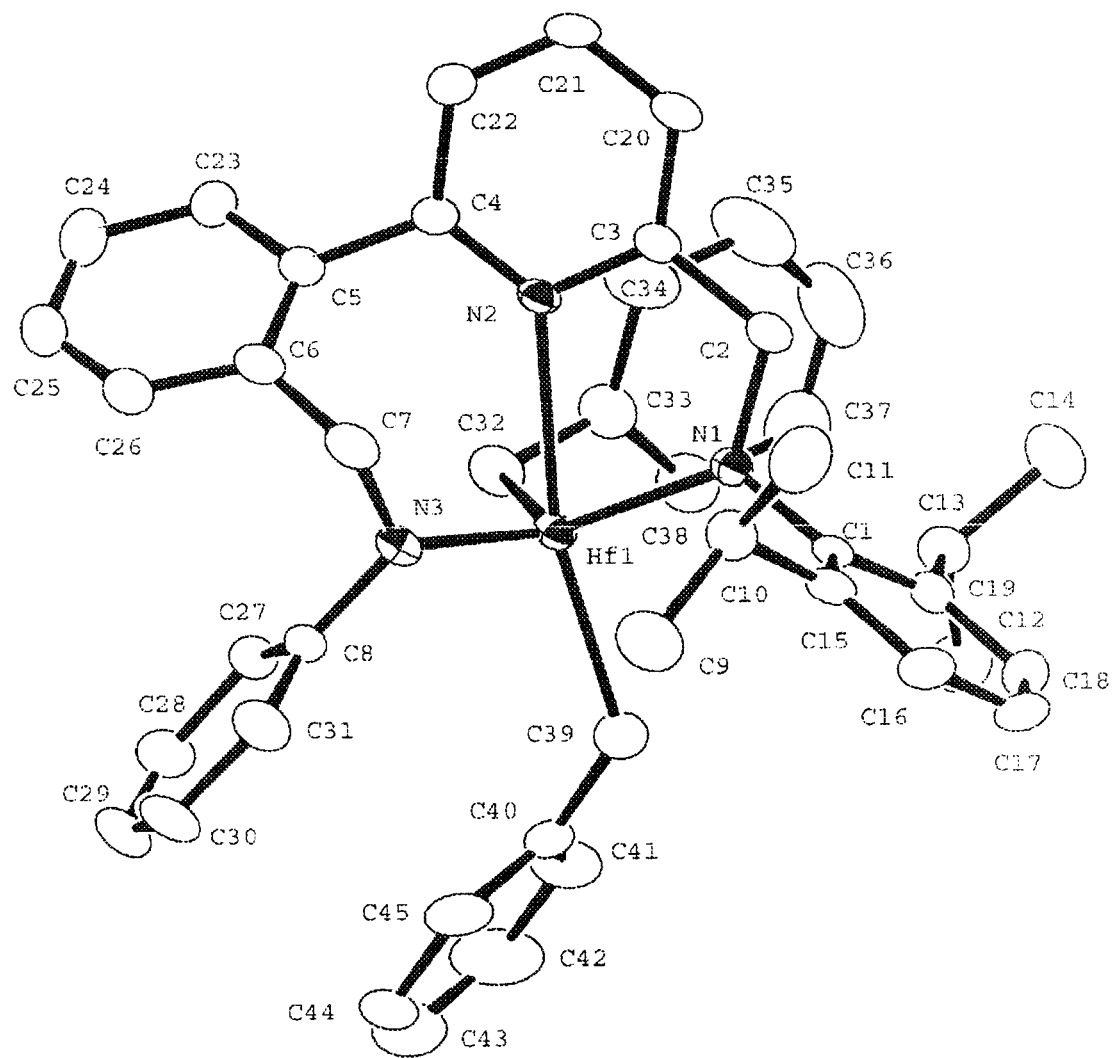
FIG. 30—Molecular structure (shown with 30% thermal ellipsoids) of complex D as determined by single-crystal X-ray diffraction.
Figure 31:
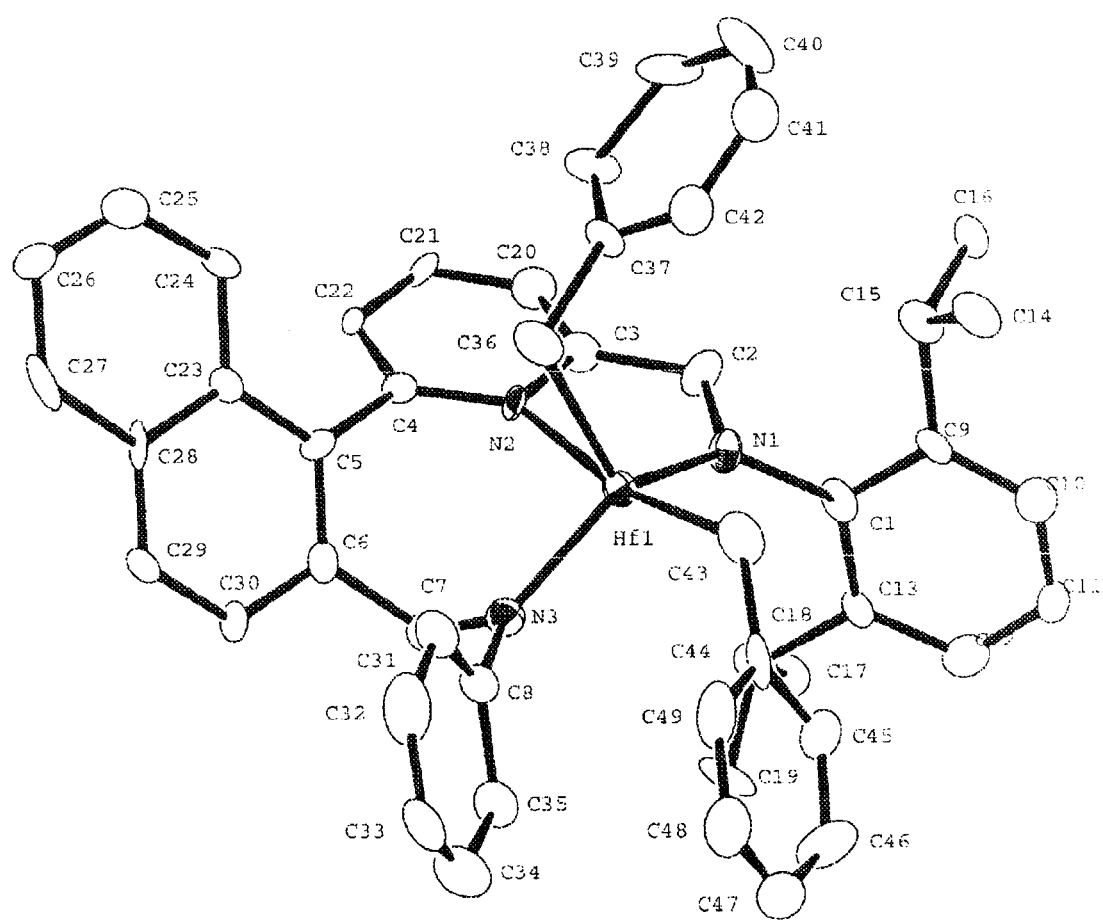
FIG. 31—Molecular structure (shown with 20% thermal ellipsoids) of complex H as determined by single-crystal X-ray diffraction.

Pyridyl diamide complexes may have fluxional structures in solution. Shown in FIG. 24 are $^1$H NMR spectra acquired for a pyridyl dimide complex that displays a complete lack of symmetry ($C_1$ symmetry) at −22° C., but higher symmetry ($C_S$ symmetry) at 80° C. This change in observed symmetry reflects a dynamic process that involves rotation about the pyridyl-carbon(aryl) bond to effectively inverts the structure. This fluxional process may be used to develop "fluxional catalysts", which can be used to produce polymeric products containing blocky structures. A polyolefin molecule with a blocky structure has a non-homogeneous compositional and/or stereochemical distribution of monomers along the polymeric chain. Our studies indicate that the above described fluxionality is fastest for Group 4 pyridyl diamide (PDA) complexes of the general formula (PDA)MX$_2$, where X is alkyl, the PDA ligand lacks substitution at the RIO position (based on Formula (III) described herein), and Z is a benzenyl (i.e., C$_6$H$_4$) group. Substitution of the PDA ligand at the RIO position slows down the fluxionality a modest amount. Changing the X groups to halide slows' down the fluxionality a larger amount. Changing Z to naphthalenyl (i.e., C$_{10}$H$_6$) stops the fluxionality. One method for controlling the fluxionalty in these systems would be to use a sub-stoichiometric amount of activator to form a mixture of activated and unactivated species. Of the two, the unactivated species would be expected to undergo relatively fast fluxionality. Thus this would provide a mechanism to produce blocky polyolefins when this system is employed in the presence of, or in the absence of, Group 12 or 13 organometallics (e.g., ZnEt$_2$, AlEt$_3$) that can facilitate polymeryl chain transfer.

Activators

After the complexes have been synthesized, catalyst systems may be formed by combining them with activators in any manner known from the literature including by supporting them for use in slurry or gas phase polymerization. The catalyst systems may also be added to or generated in solution polymerization or bulk polymerization (in the monomer). The catalyst system typically comprises a complex as described above and an activator such as alumoxane or a non-coordinating anion. Activation may be performed using alumoxane solution including methyl alumoxane, referred to as MAO, as well as modified MAO, referred to herein as MMAO, containing some higher alkyl groups to improve the solubility. Particularly useful MAO can be purchased from Albemarle, typically in a 10 wt % solution in toluene. The catalyst system employed in the present invention preferably uses an activator selected from alumoxanes, such as methyl alumoxane, modified methyl alumoxane, ethyl alumoxane, iso-butyl alumoxane, and the like.

When an alumoxane or modified alumoxane is used, the complex-to-activator molar ratio is from about 1:3000 to 10:1; alternatively 1:2000 to 10:1; alternatively 1:1000 to 10:1; alternatively, 1:500 to 1:1; alternatively 1:300 to 1:1; alternatively 1:200 to 1:1; alternatively 1:100 to 1:1; alternatively 1:50 to 1:1; alternatively 1:10 to 1:1. When the activator is an alumoxane (modified or unmodified), some embodiments select the maximum amount of activator at a 5000-fold molar excess over the catalyst precursor (per metal catalytic site). The preferred minimum activator-to-complex ratio is 1:1 molar ratio.

Activation may also be performed using non-coordinating anions, referred to as NCA's, of the type described in EP 277 003 A1 and EP 277 004 A1. NCA may be added in the form of an ion pair using, for example, [DMAH]$^+$ [NCA]$^-$ in which the N,N-dimethylanilinium (DMAH) cation reacts with a basic leaving group on the transition metal complex to form a transition metal complex cation and [NCA]$^-$. The cation in the precursor may, alternatively be trityl. Alternatively, the transition metal complex may be reacted with a neutral NCA precursor, such as B(C$_6$F$_5$)$_3$, which abstracts an anionic group from the complex to form an activated species. Useful activators include N,N-dimethylanilinium tetrakis (pentafluorophenyl)borate (i.e., [PhNMe$_2$H]B(C$_6$F$_5$)$_4$) and N,N-dimethylanilinium tetrakis (heptafluoronaphthyl)borate, where Ph is phenyl, and Me is methyl.

Additionally preferred activators useful herein include those described in U.S. Pat. No. 7,247,687 at column 169, line 50 to column 174, line 43, particularly column 172, line 24 to column 173, line 53.

When an NCA (such as an ionic or neutral stoichiometric activator) is used, the complex-to-activator molar ratio is typically from 1:10 to 1:1; 1:10 to 10:1; 1:10 to 2:1; 1:10 to 3:1; 1:10 to 5:1; 1:2 to 1.2:1; 1:2 to 10:1; 1:2 to 2:1; 1:2 to 3:1; 1:2 to 5:1; 1:3 to 1.2:1; 1:3 to 10:1; 1:3 to 2:1; 1:3 to 3:1; 1:3 to 5:1; 1:5 to 1:1; 1:5 to 10:1; 1:5 to 2:1; 1:5 to 3:1; 1:5 to 5:1; 1:1 to 1:1.2.

Alternately a co-activator, such as a group 1, 2, or 13 organometallic species (e.g., an alkyl aluminum compound such as tri-n-octyl aluminum), may also be used in the catalyst system herein. The complex-to-co-activator molar ratio is from 1:100 to 100:1; 1:75 to 75:1; 1:50 to 50:1; 1:25 to 25:1; 1:15 to 15:1; 1:10 to 10:1; 1:5 to 5:1; 1:2 to 2:1; 1:100 to 1:1; 1:75 to 1:1; 1:50 to 1:1; 1:25 to 1:1; 1:15 to 1:1; 1:10 to 1:1; 1:5 to 1:1; 1:2 to 1:1; 1:10 to 2:1.

Supports

The complexes described herein may be supported (with or without an activator) by any method effective to support other coordination catalyst systems, effective meaning that the catalyst so prepared can be used for oligomerizing or polymerizing olefin in a heterogeneous process. The catalyst precursor, activator, co-activator if needed, suitable solvent, and support may be added in any order or simultaneously. Typically, the complex and activator may be combined in solvent to form a solution. Then the support is added, and the mixture is stirred for 1 minute to 10 hours. The total solution volume may be greater than the pore volume of the support, but some embodiments limit the total solution volume below that needed to form a gel or slurry (about 90% to 400%, preferably about 100% to 200% of the pore volume). After stirring, the residual solvent is removed under vacuum, typically at ambient temperature and over 10-16 hours. But greater or lesser times and temperatures are possible.

The complex may also be supported absent the activator; in that case, the activator (and co-activator if needed) is added to a polymerization process's liquid phase. Additionally, two or more different complexes may be placed on the same support. Likewise, two or more activators or an activator and co-activator may be placed on the same support.

Suitable solid particle supports are typically comprised of polymeric or refractory oxide materials, each being preferably porous. Preferably, any support material that has an average particle size greater than 10 µm is suitable for use in this invention. Various embodiments select a porous support material, such as for example, talc, inorganic oxides, inorganic chlorides, for example magnesium chloride and resinous support materials such as polystyrene polyolefin or polymeric compounds or any other organic support material and the like. Some embodiments select inorganic oxide materials as the support material including Group-2, -3, -4, -5, -13, or -14 metal or metalloid oxides. Some embodiments select the catalyst support materials to include silica, alumina, silica-alumina, and their mixtures. Other inorganic oxides may serve either alone or in combination with the silica, alumina, or silica-alumina. These are magnesia, titania, zirconia, and the like. Lewis acidic materials such as montmorillonite and similar clays may also serve as a support. In this case, the support can optionally double as the activator component; however, an additional activator may also be used.

The support material may be pretreated by any number of methods. For example, inorganic oxides may be calcined, chemically treated with dehydroxylating agents such as aluminum alkyls and the like, or both.

As stated above, polymeric carriers will also be suitable in accordance with the invention, see for example the descriptions in WO 95/15815 and U.S. Pat. No. 5,427,991. The methods disclosed may be used with the catalyst complexes, activators or catalyst systems of this invention to adsorb or absorb them on the polymeric supports, particularly if made up of porous particles, or may be chemically bound through functional groups bound to or in the polymer chains.

Useful supports typically have a surface area of from 10-700 $m^2/g$, a pore volume of 0.1-4.0 cc/g and an average particle size of 10-500 µm. Some embodiments select a surface area of 50-500 $m^2/g$, a pore volume of 0.5-3.5 cc/g, or an average particle size of 20-200 µm. Other embodiments select a surface area of 100-400 $m^2/g$, a pore volume of 0.8-3.0 cc/g, and an average particle size of 30-100 µm. Useful supports typically have a pore size of 10-1000 Angstroms, alternatively 50-500 Angstroms, or 75-350 Angstroms.

The catalyst complexes described herein are generally deposited on the support at a loading level of 10-100 micromoles of complex per gram of solid support; alternately 20-80 micromoles of complex per gram of solid support; or 40-60 micromoles of complex per gram of support. But greater or lesser values may be used provided that the total amount of solid complex does not exceed the support's pore volume.

Polymerization

Invention catalyst complexes are useful in polymerizing unsaturated monomers conventionally known to undergo metallocene-catalyzed polymerization such as solution, slurry, gas-phase, and high-pressure polymerization. Typically one or more of the complexes described herein, one or more activators, and one or more monomers are contacted to produce polymer. The complexes may be supported and as such will be particularly useful in the known, fixed-bed, moving-bed, fluid-bed, slurry, solution, or bulk operating modes conducted in single, series, or parallel reactors.

One or more reactors in series or in parallel may be used in the present invention. The complexes, activator and when required, co-activator, may be delivered as a solution or slurry, either separately to the reactor, activated in-line just prior to the reactor, or preactivated and pumped as an activated solution or slurry to the reactor. Polymerizations are carried out in either single reactor operation, in which monomer, comonomers, catalyst/activator/co-activator, optional scavenger, and optional modifiers are added continuously to a single reactor or in series reactor operation, in which the above components are added to each of two or more reactors connected in series. The catalyst components can be added to the first reactor in the series. The catalyst component may also be added to both reactors, with one component being added to first reaction and another component to other reactors. In one preferred embodiment, the complex is activated in the reactor in the presence of olefin.

In a particularly preferred embodiment, the polymerization process is a continuous process.

Polymerization process used herein typically comprises contacting one or more alkene monomers with the complexes (and, optionally, activator) described herein. For purpose of this invention alkenes are defined to include multi-alkenes (such as dialkenes) and alkenes having just one double bond. Polymerization may be homogeneous (solution or bulk polymerization) or heterogeneous (slurry—in a liquid diluent, or gas phase—in a gaseous diluent). In the case of heterogeneous slurry or gas phase polymerization, the complex and activator may be supported. Silica is useful as a support herein. Chain transfer agents (such as hydrogen or diethyl zinc) may be used in the practice of this invention.

The present polymerization processes may be conducted under conditions preferably including a temperature of about 30° C. to about 200° C., preferably from 60° C. to 195° C., preferably from 75° C. to 190° C. The process may be conducted at a pressure of from 0.05 to 1500 MPa. In a preferred embodiment, the pressure is between 1.7 MPa and 30 MPa, or in another embodiment, especially under supercritical conditions, the pressure is between 15 MPa and 1500 MPa.

Monomers

Monomers useful herein include olefins having from 2 to 40 carbon atoms, alternately 2 to 12 carbon atoms (preferably ethylene, propylene, butylene, pentene, hexene, heptene, octene, nonene, decene, and dodecene) and optionally also polyenes (such as dienes). Particularly preferred monomers include ethylene, and mixtures of $C_2$ to $C_{10}$ alpha olefins, such as ethylene-propylene, ethylene-hexene, ethylene-octene, propylene-hexene, and the like.

The complexes described herein are also particularly effective for the polymerization of ethylene, either alone or in combination with at least one other olefinically unsaturated monomer, such as a $C_3$ to $C_{20}$ α-olefin, and particularly a $C_3$ to $C_{12}$ α-olefin. Likewise, the present complexes are also particularly effective for the polymerization of propylene, either alone or in combination with at least one other olefinically unsaturated monomer, such as ethylene or a $C_4$ to $C_{20}$ α-olefin, and particularly a $C_4$ to $C_{20}$ α-olefin. Examples of preferred α-olefins include ethylene, propylene, butene-1, pentene-1, hexene-1, heptene-1, octene-1, nonene-1, decene-1, dodecene-1,4-methylpentene-1,3-methylpentene-1,3,5,5-trimethylhexene-1, and 5-ethylnonene-1.

In some embodiments, the monomer mixture may also comprise one or more dienes at up to 10 wt %, such as from 0.00001 to 1.0 wt %, for example from 0.002 to 0.5 wt %, such as from 0.003 to 0.2 wt %, based upon the monomer mixture. Non-limiting examples of useful dienes include, cyclopentadiene, norbornadiene, dicyclopentadiene, 5-ethylidene-2-norbornene, 5-vinyl-2-norbornene, 1,4-hexadiene, 1,5-hexadiene, 1,5-heptadiene, 1,6-heptadiene, 6-methyl-1,6-heptadiene, 1,7-octadiene, 7-methyl-1,7-octadiene, 1,9-decadiene, and 9-methyl-1,9-decadiene.

Where olefins are used that give rise to short chain branching, such as propylene, the catalyst systems may, under appropriate conditions, generate stereoregular polymers or polymers having stereoregular sequences in the polymer chains.

In a preferred embodiment, the catalyst complexes described herein, preferably as represented by formula (I), (II), or (III), preferably formula (III) are used in any polymerization process described above to produce ethylene homopolymers or copolymers, propylene homopolymers or copolymers. In a preferred embodiment, the catalyst complexes described herein, preferably as represented by formula (I), (II), or (III), preferably formula (III) are used in any polymerization process described above to produce polyalphaolefins (PAO's), e.g., polymers of $C_3$ to Co alphaolefins, having low number average molecular weight (e.g., 30,000 g/mol or less (as determined as described in US 2008/0045638. pg 36-38), such as dimers, trimers, tetramers, pentamers) of $C_4$ to $C_{24}$ (preferably $C_5$ to $C_{18}$, preferably $C_6$ to $C_{14}$, even preferably $C_8$ to $C_{12}$, most preferably $C_{10}$) branched or linear alpha-olefins, provided that $C_3$ and $C_4$ alpha-olefins are present at 10 wt % or less. Suitable olefins include propylene, 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, and blends thereof. Polymers of linear alpha olefins (LAO's) with only even carbon numbers between 6 and 18 (inclusive) are particularly preferred. In one embodiment, a single LAO is used to prepare the oligomers. In this case, a preferred embodiment involves the oligomerization of 1-decene, and the PAO is a mixture of oligomers (including, for example, dimers, trimers, tetramers, pentamers, and higher) of 1-decene. In another embodiment, the PAO comprises oligomers of two or more $C_3$ to $C_{18}$ LAOs (preferably $C_5$ to $C_{18}$ LAOs), to make 'bipolymer' or 'terpolymer' or higher-order copolymer combinations, provided that $C_3$ and $C_4$ LAOs are present at 10 wt % or less. In this case, a preferred embodiment involves the polymerization of a mixture of 1-octene, 1-decene, and 1-dodecene, and the PAO is a mixture of oligomers (for example, dimers, trimers, tetramers, pentamers, and higher) of 1-octene, 1-decene, and 1-dodecene. In a preferred embodiment, the PAO has a viscosity index (ASTM D 2270) of 120 or more, preferably 150 or more, preferably 200 or more and a pour point (ASTM D 97) of −20° C. or less, preferably −25° C. or less, preferably −30° C. or less and a flash point (ASM D 92) of 200° C. or more, preferably 220° C. or more preferably 250° C. or more.

Scavengers

In some embodiments, when using the complexes described herein, particularly when they are immobilized on a support, the catalyst system will additionally comprise one or more scavenging compounds. Here, the term scavenging compound means a compound that removes polar impurities from the reaction environment. These impurities adversely affect catalyst activity and stability. Typically, the scavenging compound will be an organometallic compound such as the Group-13 organometallic compounds of U.S. Pat. Nos. 5,153,157, 5,241,025 and WO-A-91/09882, WO-A-94/03506, WO-A-93/14132, and that of WO 95/07941. Exemplary compounds include triethyl aluminum, triethyl borane, tri-iso-butyl aluminum, methyl alumoxane, iso-butyl alumoxane, and tri-n-octyl aluminum. Those scavenging compounds having bulky or $C_6$-$C_{20}$ linear hydrocarbyl substituents connected to the metal or metalloid center usually minimize adverse interaction with the active catalyst. Examples include triethylaluminum, but more preferably, bulky compounds such as tri-iso-butyl aluminum, tri-iso-prenyl aluminum, and long-chain linear alkyl-substituted aluminum compounds, such as tri-n-hexyl aluminum, tri-n-octyl aluminum, or tri-n-dodecyl aluminum. When alumoxane is used as the activator, any excess over that needed for activation will scavenge impurities and additional scavenging compounds may be unnecessary. Alumoxanes also may be added in scavenging quantities with other activators, e.g., methylalumoxane, $[Me_2HNPhr]^+[B(pfp)_4]^-$ or $B(pfp)_3$ (perfluorophenyl=pfp=$C_6F_5$).

In a preferred embodiment, two or more complexes are combined with diethyl zinc in the same reactor with monomer. Alternately, one or more complexes are combined with another catalyst (such as a metallocene) and diethyl zinc in the same reactor with monomer.

Polymer Products

While the molecular weight of the polymers produced herein is influenced by reactor conditions including temperature, monomer concentration and pressure, the presence of chain terminating agents and the like, the homopolymer and copolymer products produced by the present process may have an Mw of about 1,000 to about 2,000,000 g/mol, alternately of about 30,000 to about 600,000 g/mol, or alternately of about 100,000 to about 500,000 g/mol, as determined by Gel Permeation Chromatography. Preferred polymers produced here may be homopolymers or copolymers. In a preferred embodiment, the comonomer(s) are present at up to 50 mol %, preferably from 0.01 to 40 mol %, preferably 1 to 30 mol %, preferably from 5 to 20 mol %.

End Uses

Articles made using polymers produced herein may include, for example, molded articles (such as containers and bottles, e.g., household containers, industrial chemical containers, personal care bottles, medical containers, fuel tanks, and storageware, toys, sheets, pipes, tubing) films, non-wovens, and the like. It should be appreciated that the list of applications above is merely exemplary, and is not intended to be limiting.

In another embodiment, this invention relates to:

1. A pyridyldiamido transition metal complex for use in alkene polymerization represented by the formula: (I), (II), or (III):

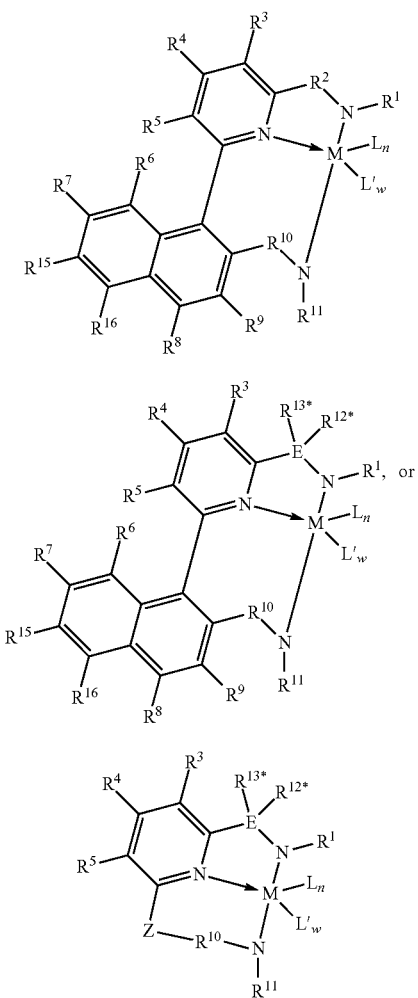

wherein:

M is a Group 3, 4, 5, 6, 7, 8, 9, 10, 11, or 12 metal (preferably a Group 4 metal, preferably Ti, Zr or Hf);

$R^1$ and $R^{11}$ are independently selected from the group consisting of hydrocarbyls, substituted hydrocarbyls, and silyl groups (preferably alkyl, aryl, heteroaryl, and silyl groups);

$R^2$ and $R^{10}$ are each, independently, -E($R^{12}$)($R^{13}$)— (preferably $R^{12}$ and $R^{13}$ are the same, preferably $R^{10}$ is $CH_2$;

E is carbon, silicon, or germanium (preferably carbon);

each $R^{12}$, $R^{13}$, $R^{12*}$, and $R^{13*}$ is independently selected from the group consisting of hydrogen, hydrocarbyl, and substituted hydrocarbyl, alkoxy, silyl, amino, aryloxy, halogen, and phosphino (preferably hydrogen, alkyl, aryl, alkoxy, silyl, amino, aryloxy, heteroaryl, halogen, and phosphino), $R^{12}$ and $R^{13}$ and/or $R^{12*}$ and $R^{13*}$ may be joined to form a saturated, substituted or unsubstituted hydrocarbyl ring, where the ring has 4, 5, 6, or 7 ring carbon atoms and where substitutions on the ring can join to form additional rings, or $R^{12}$ and $R^{13}$ and/or $R^{12*}$ and $R^{13*}$ may be joined to form a saturated heterocyclic ring, or a saturated substituted heterocyclic ring where substitutions on the ring can join to form additional rings, provided that at least one of $R^{12*}$ and $R^{13*}$ is a $C_1$ to $C_{100}$ (preferably $C_6$ to $C_0$, preferably $C_7$ to $C_{30}$, preferably $C_8$ to $C_{20}$) substituted or unsubstituted hydrocarbyl group (preferably aryl, phenyl, substituted phenyl, alkyl or aryl substituted phenyl, $C_2$ to $C_{30}$ alkyl or aryl substituted phenyl, 2-substituted phenyl, 2-isopropylphenyl, 2,4,6-trimethylphenyl, and the like);

$R^3$, $R^4$, and $R^5$ are independently selected from the group consisting of hydrogen, hydrocarbyls, substituted hydrocarbyls, alkoxy, aryloxy, halogen, amino, and silyl, (preferably hydrogen, alkyl, alkoxy, aryloxy, halogen, amino, silyl, and aryl), and wherein adjacent R groups ($R^3$ & $R^4$ and/or $R^4$ & $R^5$) may be joined to form a substituted or unsubstituted hydrocarbyl or heterocyclic ring, where the ring has 5, 6, 7, or 8 ring atoms and where substitutions on the ring can join to form additional rings;

$R^6$, $R^7$, $R^8$, $R^9$, $R^{15}$, and $R^{16}$ are independently selected from the group consisting of hydrogen, hydrocarbyls, substituted hydrocarbyls, alkoxy, halogen, amino, and silyl, and the pairs of positions, and wherein adjacent R groups ($R^6$ & $R^7$, and/or $R^7$ & $R^{15}$, and/or $R^{16}$ & $R^{15}$, and/or $R^8$ & $R^9$) may be joined to form a saturated, substituted or unsubstituted hydrocarbyl or heterocyclic ring, where the ring has 5, 6, 7, or 8 ring carbon atoms and where substitutions on the ring can join to form additional rings;

L is an anionic leaving group, where the L groups may be the same or different and any two L groups may be linked to form a dianionic leaving group;

n is 0, 1, 2, 3, or 4;

L' is neutral Lewis base;

w is 0, 1, 2, 3, or 4;

Z is —($R^{14*}$)$_p$-Q-J($R^{15*}$)$_q$— where Q or J is bonded to $R^{10}$;

J is C or Si, preferably C;

Q is C, O, N, or Si, preferably C;

$R^{14*}$ and $R^{15*}$ are independently selected from the group consisting of hydrogen, hydrocarbyls, and substituted hydrocarbyls, (preferably hydrogen and alkyls), and wherein adjacent $R^{14*}$ and $R^{15*}$ groups may be joined to form an aromatic or saturated, substituted or unsubstituted hydrocarbyl ring, where the ring has 5, 6, 7, or 8 ring carbon atoms and where substitutions on the ring can join to form additional rings;

p is 1 or 2; and q is 1 or 2.

2. A complex according to paragraph 1 in which M is Ti, Zr, or Hf.

3. A complex according to paragraph 1 or 2 in which $R^2$ is $CH_2$, and/or $R^{10}$ is $CH_2$.

4. A complex according to any of the preceding paragraphs 1 to 3 in which R' and $R^3$ to $R^9$ and/or $R^{11}$ to $R^{15}$ above, including $R^{14*}$, $R^{15*}$, $R^{12*}$ and $R^{13*}$, contain no more than 30 carbon atoms, preferably from 2 to 20 carbon atoms.

5. A complex according to any of the preceding paragraphs 1 to 4 in which E is carbon and $R_1$ and $R_{11}$ are independently selected from phenyl groups that are variously substituted with between zero to five substituents that include F, Cl, Br, I, $CF_3$, $NO_2$, alkoxy, dialkylamino, hydrocarbyl (such as alkyl and aryl), and substituted hydrocarbyls (such as heteroaryl), groups with from one to ten carbons.

6. A complex according to any of the preceding paragraphs 1 to 5 in which each L is, independently, selected from halide, alkyl, aryl, alkoxy, amido, hydrido, phenoxy, hydroxy, silyl, allyl, alkenyl, triflate, alkylsulfonate, arylsulfonate, and alkynyl; and/or L' is, independently, selected from ethers, thioethers, amines, nitriles, imines, pyridines, and phosphines.

7. A complex according to any of the preceding paragraphs 1 to 6 in which one of $R^{12*}$ and $R^{13*}$ is preferably hydrogen.

8. A complex according to any of the preceding paragraphs 1 to 7 in which the pyridyldiamido transition metal complex is represented by the Formula (III) above and at least one of $R^{12*}$ and $R^{13*}$ is a group containing from 1 to 100 (preferably 6 to 40, preferably 7 to 30) carbons.

9. A complex according to any of the preceding paragraphs 1 to 8 in which the pyridyldiamido transition metal complex is represented by the Formula (III) above, $R^{12*}$ is H, $R^{13*}$ is a group containing from 1 to 100 (preferably 6 to 40, preferably 7 to 30) carbons, M is a Group 4 metal, preferably Zr or Hf, E, and E* are carbon and $R^{12}$ and $R^{13}$ are the same, preferably $R^{10}$ is $CH_2$.

10. A complex according to any of the preceding paragraphs 1 to 7 in which the pyridyldiamido transition metal complex is represented by the Formula (II) above, $R^{12*}$ is H, $R^{13*}$ is a group containing from 1 to 100 (preferably 6 to 40, preferably 7 to 30) carbons, M is a Group 4 metal (preferably Zr or Hf, preferably Hf), E, and E* are carbon, $R^{12}$ and $R^{13}$ are the same, and preferably $R^{10}$ is $CH_2$.

11. A complex according to any of the preceding paragraphs 1 to 7, wherein the complex comprises one or more of the following structures:

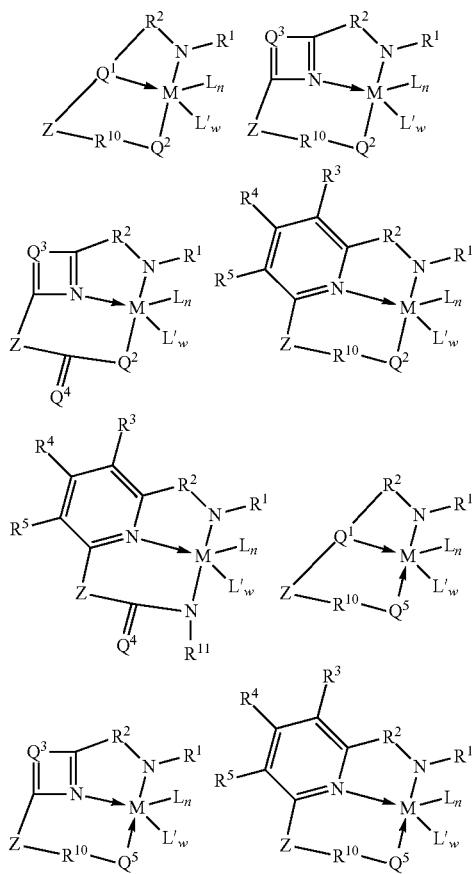

where in M, L, L', w, n, $R^{14*}$, $R^{15}$, $R^{15*}$, $R^1$, $R^{11}$, $R^2$, $R^{10}$, $R^3$, $R^4$, and $R^5$ are as defined in paragraphs 1 to 10 above;

Z is —$(R^{14*})_pQJ(R^{15*})_q$— and either Q or J is bonded to $R^{10}$;

J is C or Si, preferably C;

where Q is C, O, N, or Si, preferably C;

p is 1 or 2;

q is 1 or 2;

$R^{17}$, $R^{18}$, $R^{19}$, and $R^{20}$ are independently selected from the group consisting of hydrocarbyls (such as alkyls, aryls), substituted hydrocarbyls (such as heteroaryls), and silyl groups ($R^{17}$, $R^{18}$, $R^{19}$, and $R^{20}$ may, independently, be any preferred embodiment described above for $R^1$ in Formula (I), (II), or (III) above);

$Q^1$ is a group that links $R^2$ and Z by a three atom bridge with one of the three atoms being a group 15 or 16 element that preferably forms a dative bond to M;

$Q^2$ is a group that forms an anionic bond with M, including but not limited to a group 16 element or $NR^{17}$ or $PR^{17}$;

$Q^3$ is -(TT)- or -(TTT)- (where each T is carbon or a heteroatom, preferably C, O, S, or N, and said carbon or heteroatom may be substituted or unsubstituted) that together with the "—C—N═C—" fragment, forms a 5- or 6-membered cyclic group or a polycyclic group including the 5- or 6-membered cyclic group;

$Q^4$ is a Group 16 element, $NR^{18}$, or $PR^{18}$; and $Q^5$ is a group that forms a dative bond with M, including but not limited to $OR^{19}$, $N(R^{19})(R^{20})$, or $N(R^{19})(R^{20})$.

12. A catalyst system comprising a complex according to any of paragraphs 1 to 11 and an activator or cocatalyst such as alumoxane or a non-coordinating anion.

13. A polymerization process comprising contacting alkene monomer with a complex according to any of paragraphs 1 to 11 or the catalyst system of paragraph 12.

14. A process for preparing a Group 4 pyridyldiamido complex of any of paragraphs 1 to 11 comprising reaction of a pyridyldiamine with a group 4 transition metal complex of the general formula $MY_2L_2L'_w$, where M is Ti, Zr, or Hf, Y is a deprotonated amine or hydrocarbanion group;

L is an anionic leaving group, where the L and Y groups may be the same or different and any two L and/or Y groups may be linked to form a dianionic group;

L' is neutral Lewis base; and w is 0, 1, 2, 3, or 4.

Examples

Sources of Chemicals. Unless stated otherwise the chemicals used in the syntheses described below were purchased from commercial suppliers. 6-Bromopyridine-2-carboxaldehyde (Acros), 1-bromo-2-methylnaphthalene (Aldrich), 2-isopropoxy-4,4,5,5-tetramethyl-1,3,2-dioxaborolane (Aldrich), tert-butylamine (Merck), 2,4,6-trimethylaniline (Acros), 2,6-diisopropylaniline (Acros), 2-methylaniline (Acros), 2.5 M nBuLi in hexanes (Acros), tert-butyl phenylcarbamate (Acros), $NaBH_3CN$ (Aldrich), 1,2-dibromoethane (Acros), N-bromosuccinimide (Acros), $Pd(PPh_3)_4$ (Aldrich), triethylamine (Acros), ether, (Merck), THF (Merck), ethyl acetate (Merck), carbon tetrachloride (Merck), DMF, dimethylformamide, (Merck), methanol (Merck), toluene (Merck), hexanes (Merck), dichloromethane (Merck), dry ethanol (Merck), magnesium turnings (Acros), $MgSO_4$ (Merck), molecular sieves 4 angstrom (Merck), $Na_2CO_3(H_2O)_{10}$ (Merdk), $K_2CO_3$ (Merck), 12 M hydrochloric acid (Merck), 88% formic acid (Merck) and $CDCl_3$ (Deutero GmbH), 2-(bromomethyl)phenyl boronic acid pinacol ester (Aldrich) were used as received. Additionally, 1.6 M PhLi in ether was obtained from phenyl bromide (Acros) and magnesium turnings in ether. DMF (Merck) was dried and distilled over $CaH_2$. Diethyl ether and THF freshly distilled from benzophenone ketyl were used for organometallic synthesis and catalysis. $Zr(NMe_2)_2Cl_2(dme)$ (dme=1,2-dimethoxyethane) and $Hf(NMe_2)_2Cl_2(dme)$ were prepared as described by Erker and coworkers in Organometallics 2000, 19, 127-134. $ZrBn_2Cl_2(Et_2O)_n$ (n=1-2) was prepared by reaction of one equivalent of $ZrBn_4$ (Strem) with $ZrCl_4$ (Strem) in $Et_2O$ for 5 hours followed by filtration and crystallization of the product. $HfBn_2Cl_2(Et_2O)_n$ (n=1-2) was prepared by reaction of one equivalent of $HfBn_4$ (Strem) with $ZrCl_4$ (Strem) in $Et_2O$ for 5 hours followed by filtration and crystallization of the product.

Synthesis of Pyridyl Diamines

Outlined in Schemes 1 and 2 are general synthetic routes that were used to prepare pyridyl diamines. In the Schemes pin is pinacolate (2,3 dimethyl butane 2,3 diolate), Me is methyl, Mes is mesityl, Boc is t-butylcarbonate, t-Bu and tBu are t-butyl, Ph is phenyl, 2-Tol is ortho-tolyl, Dipp is 2,6-diisopropylphenyl, 2-iPrPh is 2-isopropylphenyl.

Scheme 1.

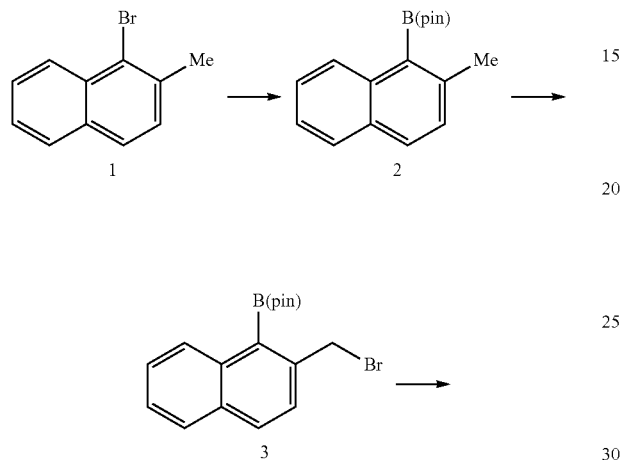

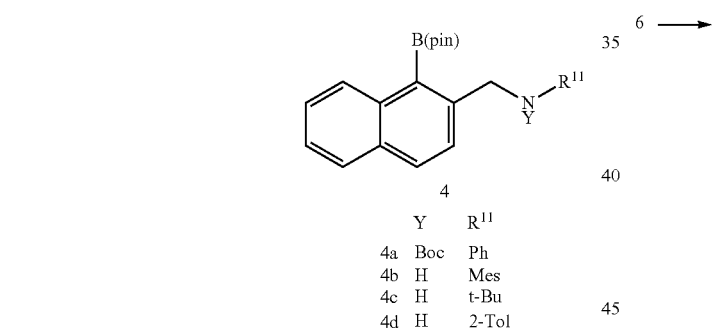

| Y | R¹¹ |
|---|---|
| 4a Boc | Ph |
| 4b H | Mes |
| 4c H | t-Bu |
| 4d H | 2-Tol |

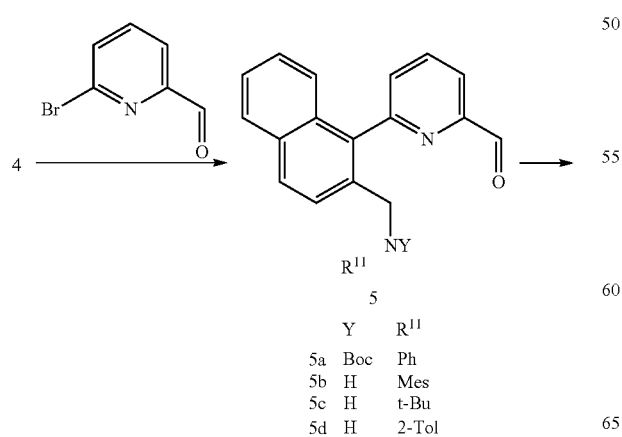

| Y | R¹¹ |
|---|---|
| 5a Boc | Ph |
| 5b H | Mes |
| 5c H | t-Bu |
| 5d H | 2-Tol |

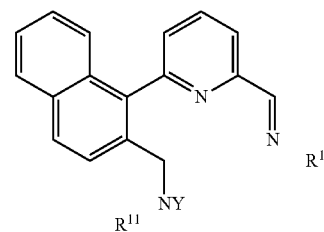

6

| | Y | R¹ | R¹¹ |
|---|---|---|---|
| 6a | Boc | Dipp | Ph |
| 6b | H | Dipp | Mes |
| 6c | H | Dipp | tBu |
| 6d | H | Dipp | 2-Tol |
| 6e | H | Mes | Mes |
| 6f | H | Mes | tBu |
| 6g | H | Mes | 2-Tol |
| 6h | H | t-Bu | Mes |
| 6i | H | t-Bu | tBu |
| 6j | H | t-Bu | 2-Tol |

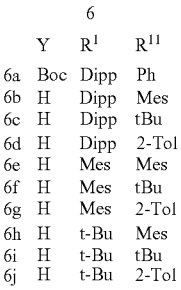

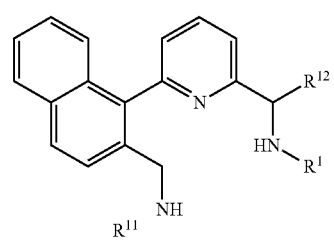

7

| | R¹ | R¹¹ | R¹² |
|---|---|---|---|
| 7a | Dipp | Ph | H |
| 7b | Dipp | Ph | 2-iPrPh |
| 7c | Mes | 2-Tol | H |
| 7d | Dipp | 2-Tol | Ph |
| 7e | t-Bu | 2-Tol | H |
| 7f | Mes | 2-Tol | Ph |
| 7g | Dipp | 2-Tol | H |
| 7h | t-Bu | 2-Tol | Ph |
| 7i | Mes | tBu | H |
| 7j | Dipp | tBu | Ph |
| 7k | t-Bu | tBu | H |
| 7l | Mes | tBu | Ph |
| 7m | Dipp | tBu | H |
| 7n | t-Bu | tBu | Ph |

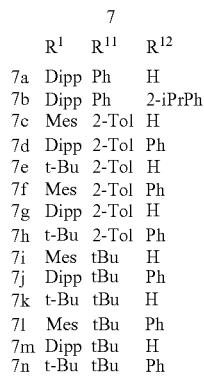

Scheme 2.

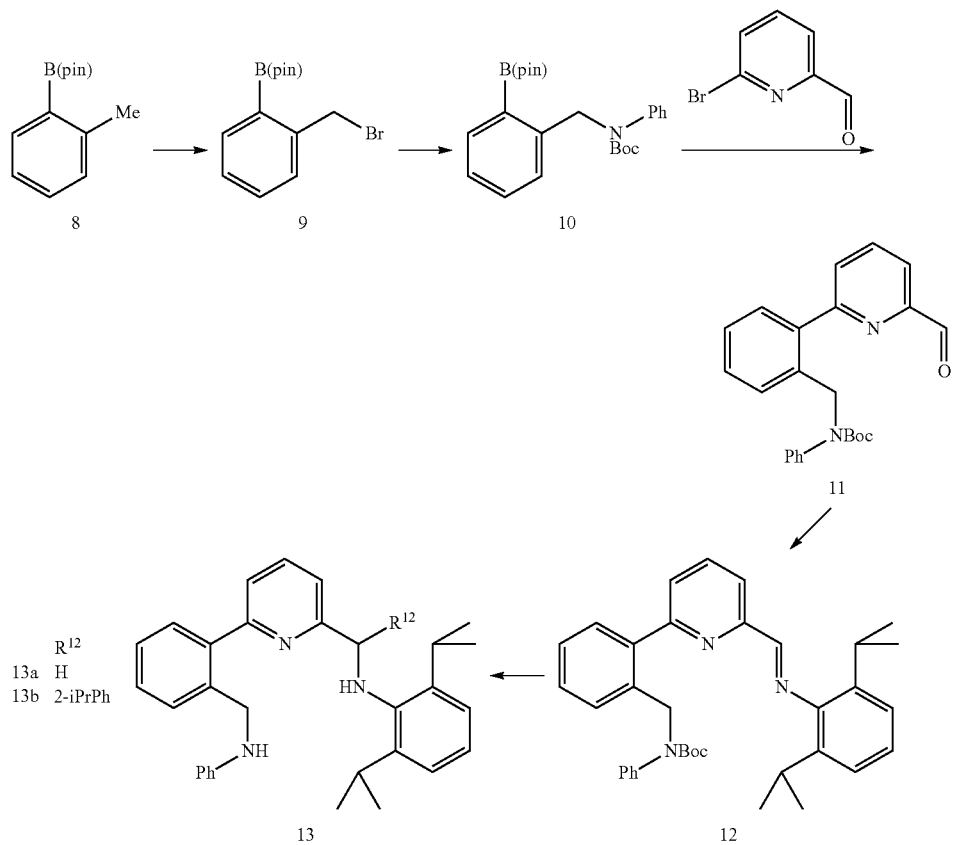

4,4,5,5-Tetramethyl-2-(2-methyl-1-naphthyl)-1,3,2-dioxaborolane (2). 1,2-Dibromoethane (~0.3 ml) was added to 6.10 g (250 mmol) magnesium turnings in 1000 cm³ of THF. This mixture was stirred for 10 min, and then 55.3 g (250 mmol) of 1-bromo-2-methylnaphthalene was added for 1 h by vigorous stirring at room temperature for 3.5 h. Further on, 46.5 g (250 mmol) of 2-isopropoxy-4,4,5,5-tetramethyl-1,3,2-dioxaborolane was added in one portion. The resulting mixture was stirred for 15 minutes and then was poured into 1000 cm³ of cold water. The product was extracted with 3×300 ml of ethyl acetate. The organic layer was separated, washed by water, brine, then dried over $MgSO_4$, and, finally, evaporated to dryness. The resulting white solid was washed by 2×75 ml of pentane and dried in vacuum. Yield 47.3 g (70%). Anal. calc. for $C_{17}H_{21}BO_2$: C, 76.14; H, 7.89. Found: C, 76.31; H, 8.02. ¹H NMR ($CDCl_3$): 8.12 (m, 1H, 8-H), 7.77 (m, 1H, 5-H), 7.75 (d, J=8.4 Hz, 1H, 4-H), 7.44 (m, 1H, 7-H), 7.38 (m, 1H, 6-H), 7.28 (d, J=8.4 Hz, 1H, 3-H), 2.63 (s, 3H, 2-Me), 1.48 (s, 12H, $CMe_2CMe_2$).

2-[2-(Bromomethyl)-1-naphthyl]-4,4,5,5-tetramethyl-1,3,2-dioxaborolane (3). A mixture of 47.3 g (176 mmol) of 4,4,5,5-tetramethyl-2-(2-methyl-1-naphthyl)-1,3,2-dioxaborolane, 33.0 g (185 mmol) of NBS (N-Bromosuccinimide) and 0.17 g of benzoyl peroxide in 340 ml of $CCl_4$ was stirred at 75° C. for 14 h. Further on, the reaction mixture was cooled to room temperature, filtered through glass fit (G3), and the filtrate was evaporated to dryness. This procedure gave 62.2 g (99%) of beige solid. Anal. calc. for $C_{17}H_{20}BBrO_2$: C, 58.83; H, 5.81. Found: C, 59.00; H, 5.95. ¹H NMR ($CDCl_3$): 8.30 (m, 1H, 8-H), 7.84 (d, J=8.3 Hz, 1H, 4-H), 7.79 (m, 1H, 5-H), 7.43-7.52 (m, 3H, 3,6,7-H), 4.96 (s, 2H, $CH_2Br$), 1.51 (s, 12H, $CMe_2CMe_2$).

tert-Butyl phenyl{[1-(4,4,5,5-tetramethyl-1,3,2-dioxaborolan-2-yl)-2-naphthyl]methyl}carbamate (4a). To a suspension of 17.0 g (88.1 mmol) of tert-butyl phenylcarbamate in 150 ml of hexanes 35.2 ml (88.1 mmol) of 2.5 M nBuLi in hexanes was slowly added at gentle reflux for ca. 15 min. This mixture was stirred for additional 30 minutes and then evaporated to dryness. The resulting white powder was added to a solution of 30.6 g (88.1 mmol) of 2-[2-(bromomethyl)-1-naphthyl]-4,4,5,5-tetramethyl-1,3,2-dioxaborolane in 300 ml of DMF. This mixture was stirred for 20 minutes at 75° C. and then poured into 1200 cm³ of cold water. The product was extracted with 3×200 ml of ethyl acetate. The combined organic extract was washed by 2×300 ml of water, dried over $MgSO_4$, and then evaporated to dryness. The crude product was purified by flash chromatography on silica gel 60 (40-63 um, eluent: hexanes-ethyl acetate=20:1, vol. then 10:1, vol.). Yield 28.0 g (69%) of yellowish oil. Anal. calc. for $C_{28}H_{34}BNO_4$: C, 73.21; H, 7.46; N, 3.05. Found: C, 73.12; H, 7.62; N, 3.24. ¹H NMR ($CDCl_3$): 8.19 (m, 1H, 8-H in naphthyl), 7.85 (d, J=8.6 Hz, 1H, 4-H in naphthyl), 7.77 (m, 1H, 5-H in naphthyl), 7.60 (d, J=8.6 Hz, 1H, 3-H in naphthyl), 7.45 (m, 1H, 7-H in naphthyl), 7.40 (m, 1H, 6-H in naphthyl), 7.20 (m, 2H, 3,5-H in Ph), 7.13 (m, 2H, 2,6-H in Ph), 7.08 (m, 1H, 4-H in Ph), 5.21 (s, 2H, $CH_2N$), 1.42 (s, 9H, $^tBu$), 1.38 (s, 12H, $CMe_2CMe_2$).

tert-Butyl {[1-(6-formylpyridin-2-yl)-2-naphthyl]methyl}phenylcarbamate (5a). A solution of 24.3 g (84.8 mmol) of $Na_2CO_3(H_2O)_1$ in a mixture of 120 ml of methanol and 450 ml of water was added to a mixture of 6.30 g (33.9 mmol) of 6-bromopyridine-2-carbaldehyde, 15.6 g (33.9 mmol) of tert-butyl phenyl{[1-(4,4,5,5-tetramethyl-1,3,2-dioxaborolan-2-yl)-2-naphthyl]methyl}carbamate and 1.96 g (1.70 mmol) of Pd(PPh$_3$)$_4$ in 600 ml of toluene by vigorous stirring at room temperature. The resulting mixture was stirred at 80° C. for 12 h. Further on, this mixture was cooled to room temperature, the organic layer was separated, dried over MgSO$_4$, and then evaporated to dryness. The product was isolated by flash chromatography on silica gel 60 (40-63 um; eluent: hexanes-ethyl acetate=50:1 and then 10:1, vol.). Yield 9.50 g (64%). Anal. calc. for C$_{28}$H$_{26}$N$_2$O$_3$: C, 76.69; H, 5.98; N, 6.39. Found: C, 76.87; H, 6.12; N, 6.25. $^1$H NMR (CDCl$_3$): 10.03 (s, 1H, CHO), 7.94-7.98 (m, 2H, 3,5-H in Py), 7.88 (m, 1H, 8-H in naphthyl), 7.83 (m, 1H, 4-H in Py), 7.75 (d, J=8.6 Hz, 1H, 4-H in naphthyl), 7.45 (m, 1H, 7-H in naphthyl), 7.34 (m, 1H, 6-H in naphthyl), 7.11-7.18 (m, 4H, 5-H in naphthyl and 3,4,5-H in Ph), 7.03 (d, J=8.6 Hz, 1H, 3-H in naphthyl), 6.93 (m, 2H, 2,6-H in Ph), 5.06 (d, J=15.9 Hz, 1H, CHH'N), 4.52 (d, J=15.9 Hz, 1H, CHH'N), 1.40 (s, 9H, $^t$Bu).

2,4,6-Trimethyl-N-{[1-(4,4,5,5-tetramethyl-1,3,2-dioxaborolan-2-yl)-2-naphthyl]methyl}aniline (4b). A mixture of 29.2 g (216 mmol) of 2,4,6-trimethylaniline, 50.0 g (144 mmol) of 2-[2-(bromomethyl)-1-naphthyl]-4,4,5,5-tetramethyl-1,3,2-dioxaborolane, and 22.0 g (159 mmol) of K$_2$CO$_3$ in 1100 cm$^3$ of DMF was stirred at 80° C. for 12 h. The resulting mixture was poured into 2000 cm$^3$ of water. The product was extracted with 3×400 ml of ethyl acetate. The combined extract was dried over MgSO$_4$ and then evaporated to dryness. The product was isolated by flash chromatography on silica gel 60 (40-63 um; eluent: dichloromethane). Yield 45.0 g (78%). Anal. Calc. For C$_{26}$H$_{32}$BNO$_2$: C, 77.81; H, 8.04; N, 3.49. Found: C, 77.99; H, 8.24; N, 3.26. $^1$H NMR (CDCl$_3$): 8.27 (m, 1H, 8-H in naphthyl), 7.84 (m, 1H, 5-H in naphthyl), 7.81 (d, J=8.4 Hz, 1H, 4-H in naphthyl), 7.54 (m, 1H, 7-H in naphthyl), 7.48 (m, 1H, 6-H in naphthyl), 7.37 (d, J=8.4 Hz, 1H, 3-H in naphthyl), 6.87 (s, 2H, 3,5-H in mesityl), 4.39 (s, 2H, CH$_2$N), 3.68 (br. s, 1H, NH), 2.31 (s, 6H, 2,6-Me in mesityl), 2.30 (s, 3H, 4-H in mesityl), 1.49 (s, 12H, CMe$_2$CMe$_2$).

6-{2-[(Mesitylamino)methyl]-1-naphthyl}pyridine-2-carbaldehyde (5b). A solution of 32.4 g (113 mmol) of Na$_2$CO$_3$ (H$_2$O)$_{10}$ in a mixture of 180 ml of methanol and 600 ml of water was added to a mixture of 8.37 g (45.0 mmol) of 6-bromopyridine-2-carbaldehyde, 18.1 g (45.0 mmol) of 2,4,6-trimethyl-N-{[1-(4,4,5,5-tetramethyl-1,3,2-dioxaborolan-2-yl)-2-naphthyl]methyl}aniline and 2.65 g (2.30 mmol) of Pd(PPh$_3$)$_4$ in 600 ml of toluene by vigorous stirring at room temperature. The resulting mixture was stirred at 80° C. for 12 h. Further on, this mixture was cooled to room temperature, the organic layer was separated, dried over MgSO$_4$, and then evaporated to dryness. The product was isolated by flash chromatography on silica gel 60 (40-63 um; eluent: dichloromethane-ethyl acetate=100:1 and then 10:1, vol.). Yield 10.7 g (63%). Anal. calc. for C$_{26}$H$_{24}$N$_2$O: C, 82.07; H, 6.36; N, 7.36. Found: C, 82.24; H, 6.49; N, 7.18. $^1$H NMR (CDCl$_3$): 10.12 (s, 1H, CHO), 8.06 (m, 1H, 3-H in Py), 7.90-7.99 (m, 3H, 5,7,8-H in naphthyl), 7.63 (d, J=8.3 Hz, 4-H in naphthyl), 7.54 (m, 1H, 5-H in Py), 7.49 (m, 1H, 4-H in Py), 7.39 (m, 1H, 6-H in naphthyl), 7.28 (d, J=8.3 Hz, 3-H in naphthyl), 6.74 (s, 2H, 3,5-H in mesityl), 3.98 (d, J=13.1 Hz, 1H, CHH'N), 3.89 (d, J=13.1 Hz, 1H, CHH'N), 3.37 (br. s, 1H, NH), 2.20 (s, 3H, 4-Me in mesityl), 2.04 (s, 6H, 2,6-Me in mesityl).

tert-Butyl{[1-(4,4,5,5-tetramethyl-1,3,2-dioxaborolan-2-yl)-2-naphthyl]methyl}amine (4c). A mixture of 30.0 g (86.5 mmol) of 2-[2-(bromomethyl)-1-naphthyl]-4,4,5,5-tetramethyl-1,3,2-dioxaborolane and 91.0 ml (63.3 g, 865 mmol) of tert-butylamine in 200 ml of THF was stirred at room temperature for 48 h. The resulting mixture was filtered through glass frit (G3) and then evaporated to dryness. The product was isolated by flash chromatography on silica gel 60 (40-63 urn; eluent: dichloromethane and then dichloromethane-methanol=1:1, vol.). Yield 27.4 g (94%). Anal. Calc. for C$_{21}$H$_{30}$BNO$_2$: C, 74.34; H, 8.91; N, 4.13. Found: C, 74.49; H, 9.09; N, 3.98. $^1$H NMR (CDCl$_3$): 8.80 (br. s, 1H, NH), 8.53 (m, 1H, 8-H in naphthyl), 7.88 (d, J=8.3 Hz, 1H, 4-H in naphthyl), 7.83 (d, J=8.3 Hz, 1H, 3-H in naphthyl), 7.71 (m, 1H, 5-H in naphthyl), 7.47 (m, 1H, 7-H in naphthyl), 7.41 (m, 1H, 6-H in naphthyl), 4.44 (s, 2H, CH$_2$N), 1.49 (s, 12H, CMe$_2$CMe$_2$), 1.41 (s, 9H, $^t$Bu).

6-{2-[(tert-Butylamino)methyl]-1-naphthyl}pyridine-2-carbaldehyde (5c). A solution of 37.0 g (129 mmol) of Na$_2$CO$_3$(H$_2$O)$_{10}$ in a mixture of 200 ml of methanol and 600 ml of water was added to a mixture of 9.58 g (51.5 mmol) of 6-bromopyridine-2-carbaldehyde, 17.5 g (51.5 mmol) of tert-butyl{[1-(4,4,5,5-tetramethyl-1,3,2-dioxaborolan-2-yl)-2-naphthyl]methyl}amine and 3.00 g (2.60 mmol) of Pd(PPh$_3$)$_4$ in 1000 ml of toluene by vigorous stirring at room temperature. The resulting mixture was stirred at 80° C. for 12 h. Further on, this mixture was cooled to room temperature; the organic layer was separated and evaporated to dryness. The residue was dissolved in 700 ml of 2 M HCl, and this solution was extracted with 3×200 ml of toluene. To the aqueous layer a solution of K$_2$CO$_3$ was added to pH 9, and the product was extracted with 2×300 ml of dichloromethane. This organic extract was dried over MgSO$_4$ and then evaporated to dryness. Yield 15.2 g (46%). Anal. calc. for C$_{21}$H$_{22}$N$_2$O: C, 79.21; H, 6.96; N, 8.80. Found: C, 79.30; H, 7.14; N, 8.65. $^1$H NMR (CDCl$_3$): 10.18 (s, 1H, CHO), 8.07 (m, 1H, 3-H in Py), 8.02 (m, 1H, 4-H in Py), 7.92 (m, 1H, 8-H in naphthyl), 7.88 (m, 1H, 5-H in naphthyl), 7.71 (m, 1H, 5-H in Py), 7.66 (d, J=8.3 Hz, 1H, 4-H in naphthyl), 7.45 (m, 1H, 7-H in naphthyl), 7.36 (m, 1H, 6-H in naphthyl), 7.28 (d, J=8.3 Hz, 1H, 3-H in naphthyl), 3.53 (m, 2H, CH$_2$N), 1.55 (br. s, 1H, NH), 0.94 (s, 9H, $^t$Bu).

N-[(6-{2-[(tert-Butylamino)methyl]-1-naphthyl}pyridin-2-yl)methylene]-2,4,6-trimethylaniline (6f). A mixture of 4.80 g (15.0 mmol) of 6-{2-[(tert-butylamino)methyl]-1-naphthyl}pyridine-2-carbaldehyde and 2.00 g (15.0 mmol) of 2,4,6-trimethylaniline in 50 ml of dry ethanol was refluxed overnight. The resulting mixture was evaporated to dryness. The product was isolated by flash chromatography on silica gel 60 (40-63 um; eluent: dichloromethane-methanol-triethylamine=100:10:1, vol.). Yield 5.80 g (88%) of orange oil. Anal. calc. for C$_{30}$H$_{33}$N$_3$: C, 82.72; H, 7.64; N, 9.65. Found: C, 82.89; H, 7.73; N, 9.54. $^1$H NMR (CDCl$_3$): 8.40-8.42 (m, 2H, CH=N and 3-H in Py), 7.99 (m, 1H, 4-H in Py), 7.91 (d, J=8.4 Hz, 1H, 4-H in naphthyl), 7.87 (m, 1H, 8-H in naphthyl), 7.66 (d, J=8.4 Hz, 1H, 3-H in naphthyl), 7.55 (m, 1H, 5-H in Py), 7.36-7.47 (m, 3H, 5,6,7-H in naphthyl), 6.90 (s, 2H, 3,5-H in mesityl), 3.60 (d, J=10.9 Hz, 1H, CHH'N), 3.53 (d, J=10.9 Hz, CHH'N), 3.40 (s, 1H, NH), 2.29 (s, 3H, 4-Me in mesityl), 2.17 (s, 6H, 2,6-Me in mesityl), 0.96 (s, 9H, $^t$Bu).

N-[(6-{2-[(tert-Butylamino)methyl]-1-naphthyl}pyridin-2-yl)methyl]-2,4,6-trimethylaniline (7i). To a solution of 1.75 g (4.10 mmol) of N-[(6-{2-[(tert-butylamino)methyl]-1-naphthyl}pyridin-2-yl)methylene]-2,4,6-trimethylaniline in 20 ml of methanol, 0.42 g (6.70 mmol) of NaBH$_3$CN was added in one portion followed by addition of three drops of 88% formic acid. The reaction mixture was refluxed under inert atmosphere for 1 hour and then poured into 50 ml of water. The crude product was extracted with 3×20 ml of ether. The organic extract was washed with water, dried over K$_2$CO$_3$, and then evaporated to dryness. The product was isolated by flash chromatography on silica gel 60 (40-63 um; eluent: dichloromethane-methanol-triethylamine=100:10:1, vol.). Yield 1.60 g (90%) of orange oil. Anal. calc. for C$_{30}$H$_{35}$N$_3$: C, 82.34; H, 8.06; N, 9.60. Found: C, 82.56; H, 8.21; N, 9.59. $^1$H NMR (CDCl$_3$): 7.89 (d, J=8.5 Hz, 1H, 4-H in naphthyl), 7.86 (m, 1H, 8-H in naphthyl), 7.77 (m, 1H, 4-H in Py), 7.65 (d, J=8.5 Hz, 3-H in naphthyl), 7.43 (m, 1H, 7-H in naphthyl)), 7.87 (m, 1H, 3-H in Py), 7.30-7.35 (m, 3H, 5-H in Py and 5,6-H in naphthyl), 6.80 (s, 2H, 3,5-H in mesityl), 4.35 (m, 2H, CH$_2$NH$^t$Bu), 3.55 (m, 2H, CH$_2$NMes), 2.94 (br. s, 2H, NH), 2.24 (s, 6H, 2,6-Me in mesityl), 2.22 (s, 3H, 4-Me in mesityl), 0.96 (s, 9H, $^t$Bu).

N-[(6-{2-[(tert-Butylamino)methyl]-1-naphthyl}pyridin-2-yl)(phenyl)methyl]-2,4,6-trimethylaniline (7l). To a solution of 1.56 g (3.60 mmol) of N-[(6-{2-[(tert-butylamino) methyl]-1-naphthyl}pyridin-2-yl)methyl]-2,4,6-trimethylaniline in 30 ml of THF 14.5 ml (10.7 mmol) of 0.74 M PhLi in ether was added by vigorous stirring at −78° C. The resulting mixture was heated to room temperature and then stirred for 10 min. Further on, 2 ml of water was added, and the resulting mixture was poured into 50 ml of water. The crude product was extracted with 3×30 ml of ether. The organic extract was washed with water, dried over K$_2$CO$_3$, and then evaporated to dryness. The product was isolated by flash chromatography on silica gel 60 (40-63 um; eluent: dichloromethane, then dichloromethane-methanol 20/1 vol., then dichloromethane-methanol-triethylamine=100:10:1, vol.). Yield 1.66 g (90%) of orange oil. Anal. calc. for C$_{36}$H$_{39}$N$_3$: C, 84.17; H, 7.65; N, 8.18. Found: C, 84.31; H, 7.77; N, 8.05. For $^1$H NMR (in CDCl$_3$) see FIG. 1—Top spectrum.

N-[(6-{2-[(tert-Butylamino)methyl]-1-naphthyl}pyridin-2-yl)methylene]-2,6-diisopropylaniline (6c). A mixture of 4.80 g (15.0 mmol) of 6-{2-[(tert-butylamino)methyl]-1-naphthyl}pyridine-2-carbaldehyde and 2.70 g (15.0 mmol) of 2,6-diisopropylaniline in 50 ml of dry ethanol was refluxed overnight. The resulting mixture was evaporated to dryness. The product was isolated by flash chromatography on silica gel 60 (40-63 um; eluent: dichloromethane-methanol-triethylamine=100:10:1, vol.). Yield 5.50 g (76%) of orange oil which crystallized at room temperature. Anal. calc. for C$_{33}$H$_{39}$N$_3$: C, 82.97; H, 8.23; N, 8.80. Found: C, 83.10; H, 8.41; N, 8.68. $^1$H NMR (CDCl$_3$): 8.41 (m, 1H, 3-H in Py), 8.38 (s, 1H, CH=N), 8.00 (m, 1H, 4-H in Py), 7.91 (d, J=8.6 Hz, 4-H in naphthyl), 7.88 (m, 1H, 8-H in naphthyl), 7.66 (d, J=8.6 Hz, 3-H in naphthyl), 7.56 (m, 1H, 5-H in Py), 7.37-7.47 (m, 3H, 5,6,7-H in naphthyl), 7.10-7.18 (m, 3H, 3,4,5-H in Ph), 3.60 (m, 2H, CH$_2$N), 3.02 (sept, J=6.8 Hz, 2H, CHMe$_2$), 1.18 (d, J=6.8 Hz, 6H, CHMeMe'), 1.19 (d, J=6.8 Hz, 6H, CHMeMe'), 0.95 (s, 9H, $^t$Bu).

N-[(6-{2-[(tert-Butylamino)methyl]-1-naphthyl}pyridin-2-yl)methyl]-2,6-diisopropylaniline (7m). To a solution of 2.45 g (5.10 mmol) of N-[(6-{2-[(tert-butylamino) methyl]-1-naphthyl}pyridin-2-yl)methylene]-2,6-diisopropylaniline in 50 ml of hot methanol 0.53 g (8.40 mmol) of NaBH$_3$CN was added in one portion followed by the addition of four drops of 88% formic acid. The resulting mixture was refluxed under inert atmosphere for 1 hour and then poured into 50 ml of water. The crude product was extracted with 3×20 ml of ether. The combined extract was washed by 2×50 ml of water, dried over K$_2$CO$_3$, and then evaporated to dryness. The product was isolated by flash chromatography on silica gel 60 (40-63 um; eluent: dichloromethane-methanol-triethylamine=100:5:1, vol.). Yield 1.60 g (65%) of orange oil. Anal. calc. for C$_{33}$H$_{41}$N$_3$: C, 82.63; H, 8.61; N, 8.76. Found: C, 82.74; H, 8.79; N, 8.60. $^1$H NMR (CDCl$_3$): 7.89 (d, J=8.3 Hz, 1H, 4-H in naphthyl), 7.86 (m, 1H, 8-H in naphthyl), 7.82 (m, 1H, 4-H in Py), 7.65 (d, J=8.3 Hz, 1H, 3-H in naphthyl), 7.47 (m, 11-1, 3-H in Py), 7.44 (m, 1H, 7-H in naphthyl), 7.33-7.40 (m, 3H, 5-H in Py and 5,6-H in naphthyl), 7.04-7.11 (m, 3H, 3,4,5-H in Ph), 4.37 (d, J=14.7 Hz, 1H, CHH'N'Bu), 4.25 (d, J=14.7 Hz, 1H, CHH'N'Bu), 3.56 (m, 2H, CH$_2$NAr), 3.33 (sept, J=7.1 Hz, 2H, CH$_2$Me$_2$), 2.04 (s, 1H, NHAr), 1.18 (d, J=7.1 Hz, 6H, CHMeMe'), 1.16 (d, J=7.1 Hz, 6H, CHMeMe'), 0.96 (s, 9H, $^t$Bu).

N-[(6-{2-[(tert-Butylamino)methyl]-1-naphthyl}pyridin-2-yl)(phenyl)methyl]-2,6-diisopropylaniline (7j). To a solution of 2.35 g (4.90 mmol) of N-[(6-{2-[(tert-butylamino) methyl]-1-naphthyl}pyridin-2-yl) methyl]-2,6-diisopropylaniline in 50 ml of THF 20.0 ml (14.8 mmol) of 0.74 M PhLi in ether was added by vigorous stirring at −78° C. The reaction mixture was heated to room temperature and stirred for 10 minutes. Further on, 2 ml of water was added, and the resulting mixture was poured into 50 ml of water. The crude product was extracted with 3×30 ml of ether. The organic extract was washed by 2×50 ml of water, dried over K$_2$CO$_3$, and then evaporated to dryness. The product was isolated by flash chromatography on silica gel 60 (40-63 um; eluent: dichloromethane-methanol-triethylamine=100:10:1, vol.). Yield 2.38 g (86%) of orange oil. Anal. calc. for C$_{39}$H$_{45}$N$_3$: C, 84.28; H, 8.16; N, 7.56. Found: C, 84.41; H, 8.17; N, 7.38. For $^1$H NMR (in CDCl$_3$) see FIG. 1—Bottom spectrum.

N-[(6-{2-[(tert-Butylamino)methyl]-1-naphthyl}pyridin-2-yl)methyl]-2-methylpropan-2-amine (7k). A mixture of 2.68 g (8.43 mmol) of 6-{2-[(tert-butylamino)methyl]-1-naphthyl}pyridine-2-carbaldehyde, 3.07 g (42.1 mmol) of tert-butylamine and 800 mg (12.7 mmol) of NaBH$_3$CN and 100 ml of dry ethanol was stirred overnight at room temperature. The resulting mixture was evaporated to dryness, and the product was isolated by flash chromatography on silica gel 60 (40-63 um; ethyl acetate-triethylamine=20:1, vol.). Yield 1.61 g (51%) of white solid. Anal. calc. for C$_{25}$H$_{33}$N$_3$: C, 79.95; H, 8.86; N, 11.19. Found: C, 80.11; H, 8.95; N, 10.95. $^1$H NMR (CDCl$_3$): 8.87 (d, J=8.6 Hz, 1H, 4-H in naphthyl), 7.83 (m, 1H, 8-H in naphthyl), 7.77 (m, 1H, 4-H in Py), 7.63 (d, J=8.6 Hz, 1H, 3-H in naphthyl), 7.46 (m, 1H, 3-H in Py), 7.41 (m, 1H, 7-H in naphthyl), 7.31-7.34 (m, 2H, 5,6-H in naphthyl), 7.27 (m, 1H, 5-H in Py), 3.97 (m, 2H, NaphCH$_2$N), 3.53 (s, 21-1, PyCH$_2$N), 1.17 (s, 9H, PyCH$_2$NH'Bu), 0.96 (s, 9H, NaphCH$_2$NH'Bu).

Figure 2:
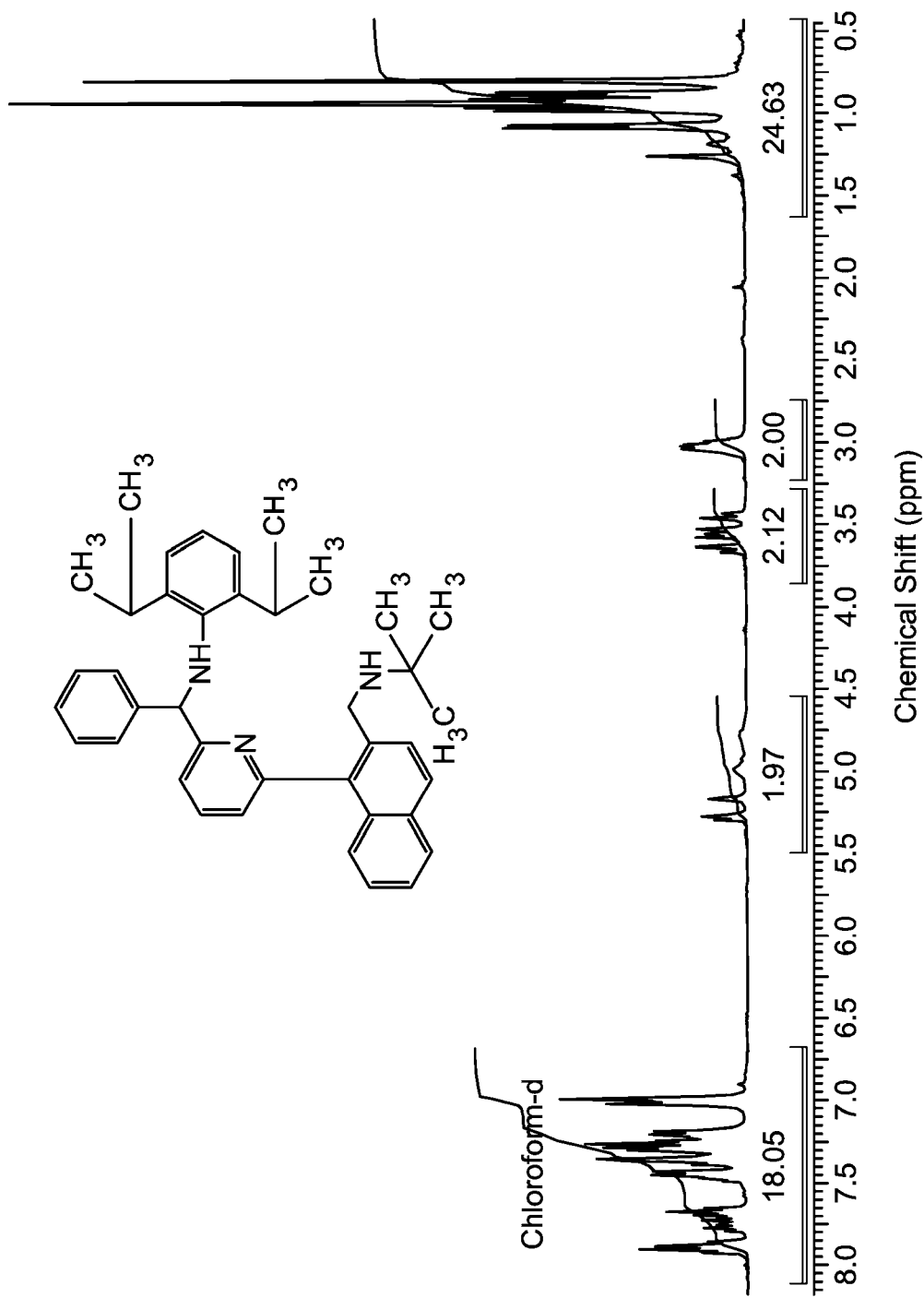
FIG. 2—$^1$H NMR spectrum of ligand 7j dissolved in $CDCl_3$.

N-[(6-{2-[(tert-Butylamino)methyl]-1-naphthyl}pyridin-2-yl)(phenyl)methyl]-2-methylpropan-2-amine (7n). A mixture of 4.10 g (12.9 mmol) of 6-{2-[(tert-butylamino)methyl]-1-naphthyl}pyridine-2-carbaldehyde, 2.83 g (38.7 mmol) of tert-butylamine, 90 g of molecular sieves (4A), and 80 ml of THF was stirred overnight. After decantation of the molecular sieves (they were additionally washed by 2×50 ml of THF), the resulting combined solution was additionally centrifuged to remove slight precipitate. The obtained solution was evaporated to dryness. A solution of the residue in 80 ml of THF was cooled to −80° C., and 50.0 ml (37.5 mmol) of 0.75 M of PhLi in ether was added. The resulting mixture was stirred for 1 h at room temperature. Further on, 20 ml of water was added. The organic layer was separated, and the aqueous layer was extracted with 2×40 ml of ether. The combined organic extract was washed by 20 ml of water, dried over K$_2$CO$_3$, and then evaporated to dryness. The product was isolated by flash chromatography on silica gel 60 (40-63 um; ethyl acetate-triethylamine=20:1, vol.). Yield 2.84 g (49%) of white solid of a ca. 1 to 1 mixture of two diastereomers. Anal.

calc. for C$_{31}$H$_{37}$N$_3$: C, 82.44; H, 8.26; N, 9.30. Found: C, 82.59; H, 8.35; N, 9.19. For $^1$H NMR (in CDCl$_3$) see FIG. 2—Top spectrum.

2-Methyl-N-{[1-(4,4,5,5-tetramethyl-1,3,2-dioxaborolan-2-yl)-2-naphthyl]methyl}aniline (4d). A mixture of 8.75 g (63.4 mmol) of K$_2$CO$_3$, 9.25 g (86.4 mmol) of 2-methylaniline and 20.0 g (57.6 mmol) of 2-[2-(bromomethyl)-1-naphthyl]-4,4,5,5-tetramethyl-1,3,2-dioxaborolane in 450 ml of DMF was stirred at 80° C. for 12 h. The resulting mixture was poured into 100 cm$^3$ of water, and the product was extracted with 3×250 ml of ethyl acetate. The combined organic extract was dried over MgSO$_4$ and then evaporated to dryness. Crystallization of this crude product from 250 ml of hexanes gave 14.4 g (67%) of brown crystals of the title compound. Anal. Calc. for C$_{24}$H$_{28}$13NO$_2$: C, 77.22; H, 7.56; N, 3.75. Found: C, 77.39; H, 7.70; N, 3.64. $^1$H NMR (CDCl$_3$): 8.20 (m, 1H, 8-H in naphthyl), 7.84 (d, J=8.5 Hz, 1H, 4-H in naphthyl), 7.82 (m, 1H, 5-H in naphthyl), 7.43-7.52 (m, 3H, 3,6,7-H in naphthyl), 7.14 (m, 1H, 5-H in Ph), 7.06 (m, 1H, 3-H in Ph), 6.79 (m, 1H, 6-H in Ph), 6.68 (m, 1H, 4-H in Ph).

6-(2-{[(2-Methylphenyl)amino]methyl}-1-naphthyl)pyridine-2-carbaldehyde (5d). A solution of 28.4 g (99.0 mmol) of Na$_2$CO$_3$(H$_2$O)$_{10}$ in a mixture of 150 ml of methanol and 580 ml of water was added to a mixture of 7.38 g (39.7 mmol) of 6-bromopyridine-2-carbaldehyde, 14.8 g (39.7 mmol) of 2-methyl-N-{ [1-(4,4,5,5-tetramethyl-1,3,2-dioxaborolan-2-yl)-2-naphthyl]methyl}aniline and 2.29 g (2.00 mmol) of Pd(PPh$_3$)$_4$ in 720 ml of toluene by vigorous stirring at room temperature. The resulting mixture was stirred at 80° C. for 12 h. Further on, this mixture was cooled to room temperature, the organic layer was separated, dried over MgSO$_4$, and then evaporated to dryness. The product was isolated by flash chromatography on silica gel 60 (40-63 um; eluent: dichloromethane-ethyl acetate=100:1 and then 20:1). Yield 10.7 g (76%). Anal. calc. for C$_{24}$H$_{20}$N$_2$O: C, 81.79; H, 5.72; N, 7.95. Found: C, 81.91; H, 5.80; N, 7.81. $^1$H NMR (CDCl$_3$): 10.10 (s, 1H, CHO), 8.01-8.05 (m, 2H, 3,4-H in Py), 7.96 (d, J=8.6 Hz, 1H, 4-H in naphthyl), 7.90 (m, 1H, 8-H in naphthyl), 7.68-7.70 (m, 2H, 5-H in Py and 3-H in naphthyl), 7.60 (m, 1H, 7-H in naphthyl), 7.41 (m, 1H, 6-H in naphthyl), 7.81 (m, 1H, 5-H in naphthyl), 7.03 (m, 2H, 3,5-H in Ph), 6.63 (m, 1H, 4-H in Ph), 6.50 (m, 1H, 6-H in Ph), 4.22 (m, 2H, CH$_2$N), 3.93 (br. s, 3H, Me).

Mesityl{[6-(2-{[(2-methylphenyl)amino]methyl}-1-naphthyl)pyridin-2-yl]methylene}amine (6g). A mixture of 1.50 g (4.26 mmol) of 6-(2-{[(2-methylphenyl)amino]methyl}-1-naphthyl)pyridine-2-carbaldehyde and 0.58 g (4.26 mmol) 2,4,6-trimethylaniline in 15 ml of dry ethanol was refluxed for 3 h. The resulting mixture was evaporated to dryness. The product was isolated from the residue by flash chromatography on silica gel 60 (40-63 um; eluent: hexanes-ethyl acetate=5:1, vol.). Yield 1.80 g (90%) of yellow oil. Anal. calc. for C$_{33}$H$_{31}$N$_3$: C, 84.40; H, 6.65; N, 8.95. Found: C, 84.62; H, 6.73; N, 8.88. $^1$H NMR (CDCl$_3$): 8.37 (m, 1H, 3-H in Py), 8.36 (s, 1H, CH=N), 7.97 (m, 1H, 4-H in Py), 7.93 (d, J=8.3 Hz, 1H, 4-H in naphthyl), 7.90 (m, 1H, 8-H in naphthyl), 7.68 (d, J=8.3 Hz, 1H, 3-H in naphthyl), 7.66 (m, 1H, 5-H in Py), 7.49 (m, 1H, 7-H in naphthyl), 7.39-7.44 (5,6-H in naphthyl), 7.03 (m, 1H, 5-H in Ph), 7.01 (m, 1H, 3-H in ortho-tolyl), 6.89 (s, 2H, 3,5-H in mesityl), 6.62 (m, 1H, 4-H in ortho-tolyl), 6.65 (m, 1H, 6-H in ortho-tolyl), 4.27 (m, 2H, CH$_2$N), 3.97 (br. s, 1H, NH), 2.29 (s, 3H, Me in ortho-tolyl), 2.14 (s, 6H, 2,6-Me in mesityl), 2.08 (s, 3H, 4-Me in mesityl).

2,4,6-Trimethyl-N-{[6-(2-{[(2-methylphenyl)amino]methyl}-1-naphthyl)pyridin-2-yl]methyl}aniline (7c). To a solution of 1.25 g (2.67 mmol) of mesityl{[6-(2-{[(2-methylphenyl)amino]methyl}-1-naphthyl)pyridin-2-yl]methylene}amine in 20 ml of methanol 0.27 g (4.30 mmol) of NaBH$_3$CN was added in one portion followed by addition of three drops of 88% formic acid. The reaction mixture was refluxed for 1 h and then poured into 50 ml of water. The crude product was extracted with 2×20 ml of ether. The organic extract was washed by 2×30 ml of water, dried over K$_2$CO$_3$, and then evaporated to dryness. The product was isolated by flash chromatography on silica gel 60 (40-63 um; eluent: hexanes-ethyl acetate=5:1, vol.). Yield 1.00 g (80%) of yellow oil. Anal. calc. for C$_{33}$H$_{33}$N$_3$: C, 84.04; H, 7.05; N, 8.91. Found: C, 84.19; H, 7.20; N, 8.76. $^1$H NMR (CDCl$_3$): 7.90 (d, J=8.5 Hz, 1H, 4-H in naphthyl), 7.88 (m, 1H, 8-H in naphthyl), 7.74 (m, 1H, 4-H in Py), 7.66 (d, J=8.5 Hz, 1H, 3-H in naphthyl), 7.47 (m, 1H, 7-H in naphthyl), 7.38 (m, 2H, 5,6-H in naphthyl), 7.32 (m, 1H, 3-H in Py), 7.31 (m, 1H, 5-H in Py), 7.02 (m, 1H, 5-H in ortho-tolyl), 7.01 (m, 1H, 3-H in ortho-tolyl), 6.78 (s, 2H, 3,5-H in mesityl), 6.62 (m, 1H, 4-H in ortho-tolyl), 6.51 (m, 1H, 6-H in ortho-tolyl), 4.31 (m, 2H, PyCH$_2$N), 4.22 (m, 2H, NaphCH$_2$N), 3.94 (br. s, 2H, NH), 2.21 (s, 3H, Me in ortho-tolyl), 2.19 (s, 6H, 2,6-Me in mesityl), 2.10 (s, 3H, 4-Me in mesityl).

2,4,6-Trimethyl-N-[[6-(2-{[(2-methylphenyl)amino]methyl}-1-naphthyl)pyridin-2-yl](phenyl)methyl]aniline (7f). To a solution of 1.05 g (2.23 mmol) of mesityl{[6-(2-{[(2-methylphenyl)amino]methyl}-1-naphthyl)pyridin-2-yl]methylene}amine in 20 ml of THF 7.60 ml (5.60 mmol) of 0.74 M PhLi in ether was added by vigorous stirring at −78° C. The resulting mixture was heated to room temperature and then stirred for 10 min. Further on, 2 ml of water was added, and then the reaction mixture was poured into 50 ml of water. The crude product was extracted with 3×20 ml of ether. The organic extract was washed by 2×30 ml of water, dried over K$_2$CO$_3$, and then evaporated to dryness. The product was isolated by flash chromatography on silica gel 60 (40-63 um; eluent: hexanes-ethyl acetate=5:1, vol.). Yield 0.90 g (66%) of yellow oil. Anal. calc. for C$_{39}$H$_{37}$N$_3$: C, 85.52; H, 6.81; N, 7.67. Found: C, 85.73; H, 6.98; N, 7.54. For $^1$H NMR (in CDCl$_3$) see FIG. 2—Bottom spectrum.

(2,6-Diisopropylphenyl){ [6-(2-{ [(2-methylphenyl)amino]methyl}-1-naphthyl)pyridin-2-yl]methylene}amine (6d). A mixture of 1.50 g (4.26 mmol) of 6-(2-{[(2-methylphenyl)amino]methyl}-1-naphthyl) pyridine-2-carbaldehyde and 0.75 g (4.26 mmol) of 2,6-diisopropylaniline in 15 ml of dry ethanol was refluxed for 3 h. Crystals precipitated from this mixture at 0° C. were collected, washed by 3×5 ml of cold ethanol, and dried in vacuum. Yield 1.92 g (88%) of yellowish crystalline solid. Anal. calc. for C$_{36}$H$_{37}$N$_3$: C, 84.50; H, 7.29; N, 8.21. Found: C, 84.73; H, 7.41; N, 8.02. $^1$H NMR (CDCl$_3$): 8.35 (m, 1H, 8-H in naphthyl), 8.33 (s, 1H, CH=N), 7.98 (m, 1H, 4-H in Py), 7.92 (d, J=8.6 Hz, 1H, 4-H in naphthyl), 7.89 (m, 1H, 5-H in naphthyl), 7.68 (d, J=8.6 Hz, 1H, 3-H in naphthyl), 7.57 (m, 1H, 3-H in Py), 7.40-7.50 (m, 3H, 5-H in Py and 6,7-H in naphthyl), 6.98-7.17 (m, 5H, 3,4,6-H in 2,6-disopropylphenyl and 3,5-H in ortho-tolyl), 6.61 (m, 1H, 4-H in ortho-tolyl), 6.53 (m, 1H, 6-H in ortho-tolyl), 4.29 (m, 2H, CH$_2$N), 3.93 (br. s, 1H, NH), 2.96 (sept, J=6.8 Hz, 2H, CHMe$_2$), 2.06 (s, 3H, Me in ortho-tolyl), 1.16 (d, J=6.8 Hz, 6H, CHMeMe'), 1.15 (d, J=6.8 Hz, 6H, CHMeMe').

2,6-Diisopropyl-N-{[6-(2-{[(2-methylphenyl)amino]methyl}-1-naphthyl)pyridin-2-yl]methyl}aniline (7g). To a solution of 1.50 g (2.90 mmol) of (2,6-diisopropylphenyl){ [6-(2-{[(2-methylphenyl)amino]methyl}-1-naphthyl)pyridin-2-yl]methylene}amine in 20 ml of methanol 0.30 g (4.70 mmol) of NaBH$_3$CN was added in one portion followed by addition of three drops of 88% formic acid. The reaction mixture was refluxed for 1 h and then poured into 50 ml of water. The crude product was extracted with 2×20 ml of ether. The organic extract was washed by water, dried over $K_2CO_3$, and then evaporated to dryness. The product was isolated by flash chromatography on silica gel 60 (40-63 um; eluent: hexanes-ethyl acetate=5:1, vol.). Yield 1.00 g (67%) of yellow oil which crystallized at room temperature. Anal. calc. for $C_{36}H_{39}N_3$: C, 84.17; H, 7.65; N, 8.18. Found: C, 84.25; H, 7.78; N, 8.00. $^1$H NMR (CDCl$_3$): 7.91 (d, J=8.4 Hz, 1H, 4-H in naphthyl), 7.89 (m, 1H, 8-H in naphthyl), 7.79 (m, 1H, 4-H in Py), 7.66 (d, J=8.4 Hz, 1H, 3-H in naphthyl), 7.47 (m, 1H, 7-H in naphthyl), 7.36-7.42 (m, 4H, 3,5-H in Py and 5,6-H in naphthyl), 7.04-7.10 (m, 3H, 3,5-H in ortho-tolyl and 4-H in 2,6-diisopropylphenyl), 7.01 (m, 2H, 3,5-H in 2,6-diisopropylphenyl), 6.61 (m, 1H, 4-H in ortho-tolyl), 6.52 (m, 1H, 6-H in ortho-tolyl), 4.22-4.35 (m, 4H, CH$_2$N), 4.02 (br. s, 1H, NH), 3.93 (br. s, 1H, NH), 3.28 (sept, J=6.8 Hz, 2H, CHMe$_2$), 2.09 (s, 3H, Me in ortho-tolyl), 1.16 (d, J=6.8 Hz, 6H, CHMeMe'), 1.14 (d, J=6.8 Hz, 6H, CHMeMe').

Figure 3:
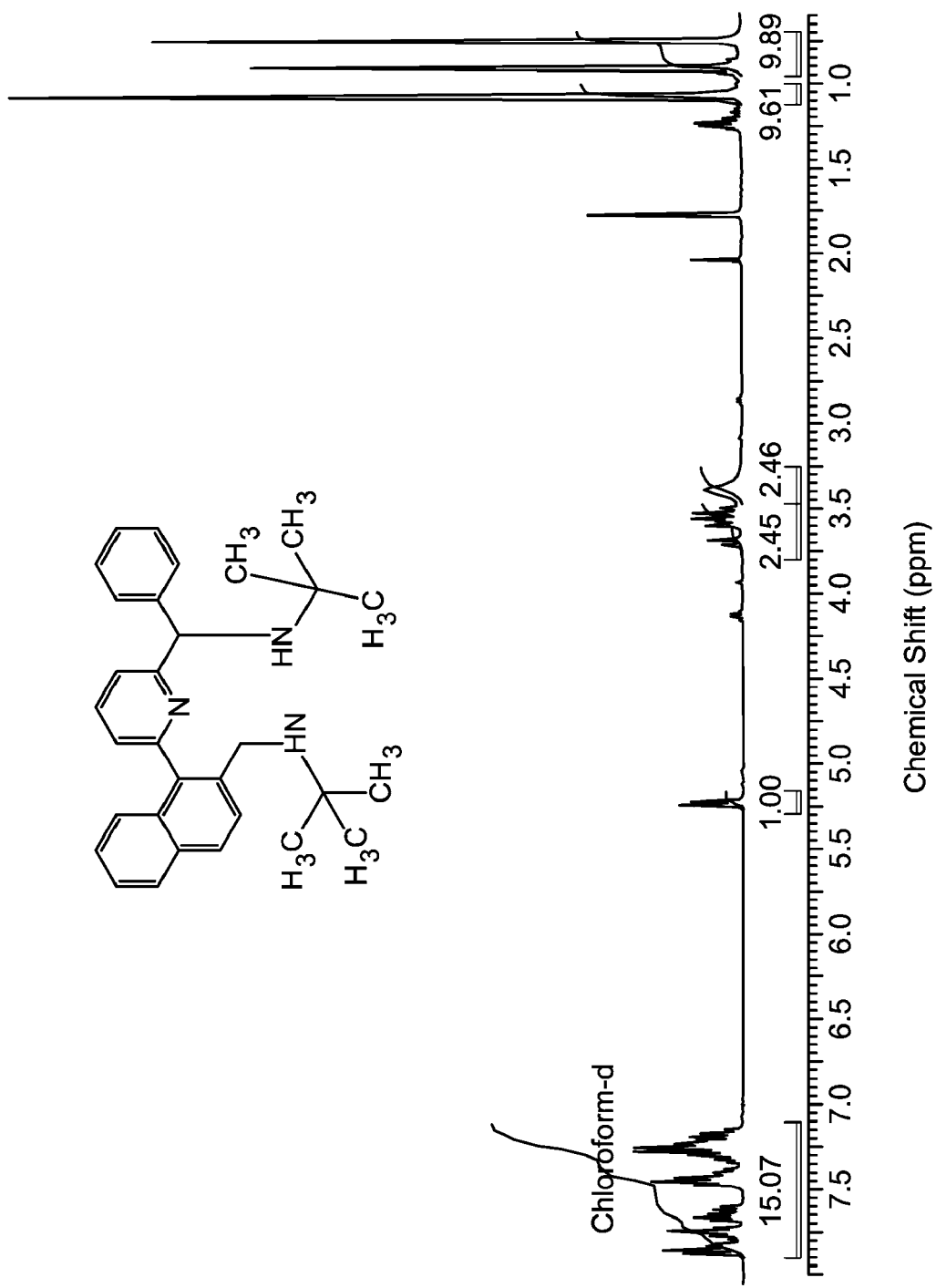
FIG. 3—$^1$H NMR spectrum of ligand 7n dissolved in $CDCl_3$.

2,6-Diisopropyl-N-[[6-(2-{[(2-methylphenyl)amino]methyl}-1-naphthyl)pyridin-2-yl](phenyl)methyl]aniline (7d). To a solution of 1.30 g (2.54 mmol) of (2,6-diisopropylphenyl){[6-(2-{[(2-methylphenyl)amino]methyl}-1-naphthyl)pyridin-2-yl]methylene}amine in 20 ml of THF 8.60 ml (6.35 mmol) of 0.74 M PhLi in ether was added by vigorous stirring at −78° C. The reaction mixture was stirred for 10 minutes at room temperature, then 2 ml of water was added, and, finally, this mixture was poured into 50 ml of water. The product was extracted with 3×20 ml of ether. The organic extract was washed by 2×30 ml of water, dried over $K_2CO_3$, and then evaporated to dryness. The product was isolated by flash chromatography on silica gel 60 (40-63 um; eluent: hexanes-ethyl acetate=5:1, vol.). Yield 1.30 g (86%) of yellow oil which crystallized at room temperature. Anal. calc. for $C_{42}H_{43}N_3$: C, 85.53; H, 7.35; N, 7.12. Found: C, 85.72; H, 7.39; N, 6.95. For $^1$H NMR (in CDCl$_3$) see FIG. 3—Top spectrum.

N-[(1-{6-[(tert-Butylamino)methyl]pyridin-2-yl}-2-naphthyl)methyl]-2-methylaniline (7e). A mixture of 1.79 g (5.09 mmol) of 6-(2-{[(2-methylphenyl)amino]methyl}-1-naphthyl)pyridine-2-carbaldehyde, 1.85 g (25.4 mmol) of tert-butylamine and 0.641 g (10.2 mmol) of NaBH$_3$CN in 100 ml of dry ethanol was stirred overnight at room temperature. The resulting mixture was evaporated to dryness. The product was isolated from the residue by flash chromatography on neutral alumina (eluent: dichloromethane, then dichloromethane-ether=1:1, vol.). Yield 1.10 g (53%) of yellowish oil. Anal. calc. for $C_{28}H_{31}N_3$: C, 82.11; H, 7.63; N, 10.26. Found: C, 82.34; H, 7.79; N, 10.11. $^1$H NMR (CDCl$_3$): 7.90 (d, J=8.6 Hz, 1H, 4-H in naphthyl), 7.88 (m, 1H, 8-H in naphthyl), 7.79 (m, 1H, 4-H in Py), 7.65 (d, J=8.6 Hz, 1H, 3-H in naphthyl), 7.38-7.48 (m, 4H, 3-H in Py and 5,6,7-H in naphthyl), 7.32 (m, 1H, 5-H in Py), 7.01-7.04 (m, 2H, 3,5-H in ortho-tolyl), 6.63 (m, 1H, 4-H in ortho-tolyl), 6.52 (m, 1H, 6-H in ortho-tolyl), 4.22 (m, 2H, Naph-CH$_2$N), 4.01 (m, 2H, Py-CH$_2$N), 3.50 (br. s, 2H, NH), 2.11 (s, 3H, Me in ortho-tolyl), 1.18 (s, 9H, $^t$Bu).

N-[(1-{6-[(tert-Butylamino)(phenyl)methyl]pyridin-2-yl}-2-naphthyl)methyl]-2-methylaniline (7h). A mixture of 2.00 g (5.68 mmol) of 6-(2-{[(2-methylphenyl)amino]methyl}-1-naphthyl)pyridine-2-carbaldehyde, 1.24 g (17.0 mmol) of tert-butylamine, 40 g of molecular sieves (4A) in 40 ml of THF was stirred overnight at room temperature. Further on, the molecular sieves were separated, washed with 2×25 ml of THF, and the resulting solution was additionally centrifuged to split off some precipitate. This solution was evaporated to dryness. A solution of the residue in 40 ml of THF was cooled to −80° C., and 23.0 ml (17.3 mmol) of 0.75 M PhLi in ether was added. The resulting mixture was heated to room temperature for 1 h, and then 10 ml of water was added. The organic layer was separated, and the aqueous layer was extracted with 2×20 ml of ether. The combined organic extract was washed by 10 ml of water, dried over $K_2CO_3$, and then evaporated to dryness. The product was isolated by flash chromatography on silica gel 60 (40-63 um; eluent: ethyl acetate-triethylamine=20:1, vol.). Yield 1.08 g (39%) of white solid as a ca. 1 to 1 mixture of two diastereomers. Anal. calc. for $C_{34}H_{35}N_3$: C, 84.08; H, 7.26; N, 8.65. Found: C, 84.26; H, 7.39; N, 8.49. For $^1$H NMR (in CDCl$_3$) see FIG. 3—Bottom spectrum.

2,6-Diisopropyl-N-((6-(2-((phenylamino)methyl)naphthalen-1-yl)pyridin-2-yl)methyl)aniline (7a). Compound 5a (1.95 g, 4.43 mmol) and tetrahydrofuran (30 mL) were combined to form a solution. Then 2,6-diisopropylaniline (0.785 g, 4.43 mmol) and 4 angstrom molecular sieves (ca. 20 mL) were added followed by a catalytic amount of p-toluenesulfonic acid monohydrate (0.005 g, 0.03 mmol). The mixture became yellow immediately. After stirring overnight the mixture was filtered and evaporated to afford the imine 6a as an oil. This was then dissolved in methanol (30 mL) and NaBH$_3$CN (0.45 g) was added followed by a few drops of 85% formic acid. The mixture was heated to reflux. Additional NaBH$_3$CN (0.45 g) and a couple drops of the formic acid were added after 15 minutes. After another 15 minutes a third portion of NaBH$_3$CN (0.45 g) and a couple drops of the formic acid were added. After a total of 2.5 hours at reflux the pale yellow mixture was poured into water (250 mL) and extracted with Et$_2$O (150 mL). The organics were dried with brine then evaporated to an oil with some water or methanol separating out. This was extracted with Et$_2$O (20 mL), dried over magnesium sulfate, filtered, and evaporated to a residue containing the Boc-protected amine product. This was dissolved chloroform (40 mL) and trifluoroacetic acid (16 mL) was added. The mixture was heated to 55° C. for 1 hour, during which time gas evolved. The mixture was then poured into 3 M NaOH (125 mL) and stirred for several minutes. The organics were extracted into Et$_2$O (200 mL) then separated, dried over sodium sulfate, and evaporated to a slightly colored oil. The crude product was purified by chromatography on basic alumina using 5:1 hexanes:CH$_2$Cl$_2$ with an increasing gradient of ethyl acetate (0.5% to 10%). The product was isolated as a thick, purple-tinted oil. $^1$H NMR (500 MHz, CD$_2$Cl$_2$): 7.93 (t, 2H), 7.85 (t, 1H), 7.69 (d, 1H), 7.37-7.52 (m, 5H), 7.00-7.11 (m, 5H), 6.63 (t, 1H), 6.57 (d, 2H), 4.06-4.37 (m, 6H), 3.33 (sept, 2H), 1.16 (d, 12H).

Figure 4:
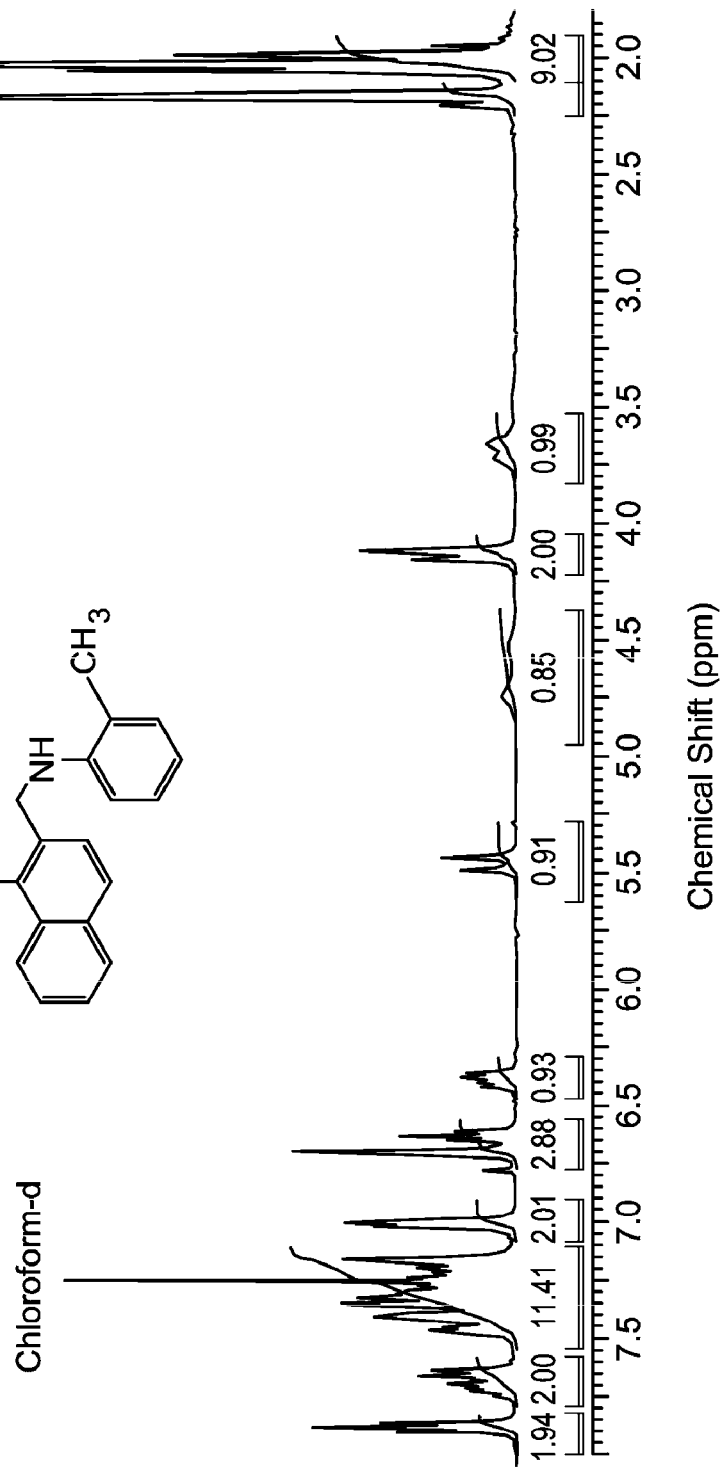
FIG. 4—$^1$H NMR spectrum of ligand 7f dissolved in $CDCl_3$.
Figure 5:
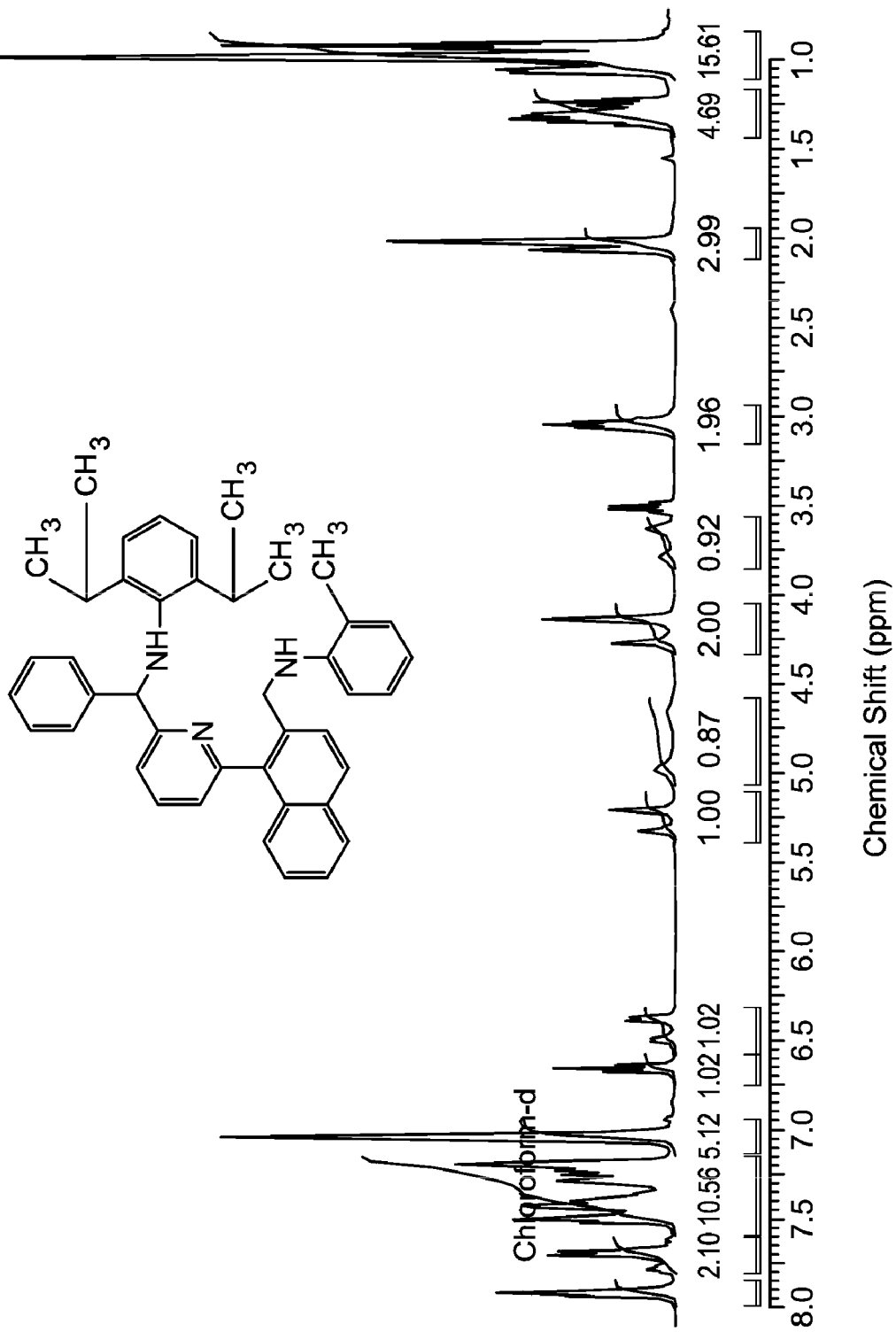
FIG. 5—$^1$H NMR spectrum of ligand 7d dissolved in $CDCl_3$.
Figure 6:
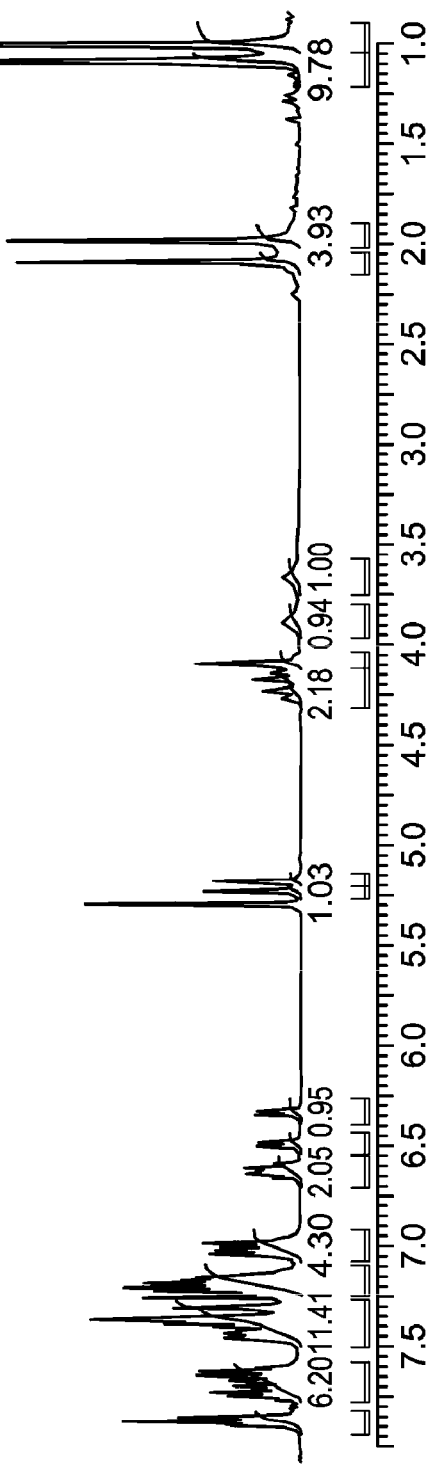
FIG. 6—$^1$H NMR spectrum of ligand 7h dissolved in $CD_2Cl_2$.
Figure 7:
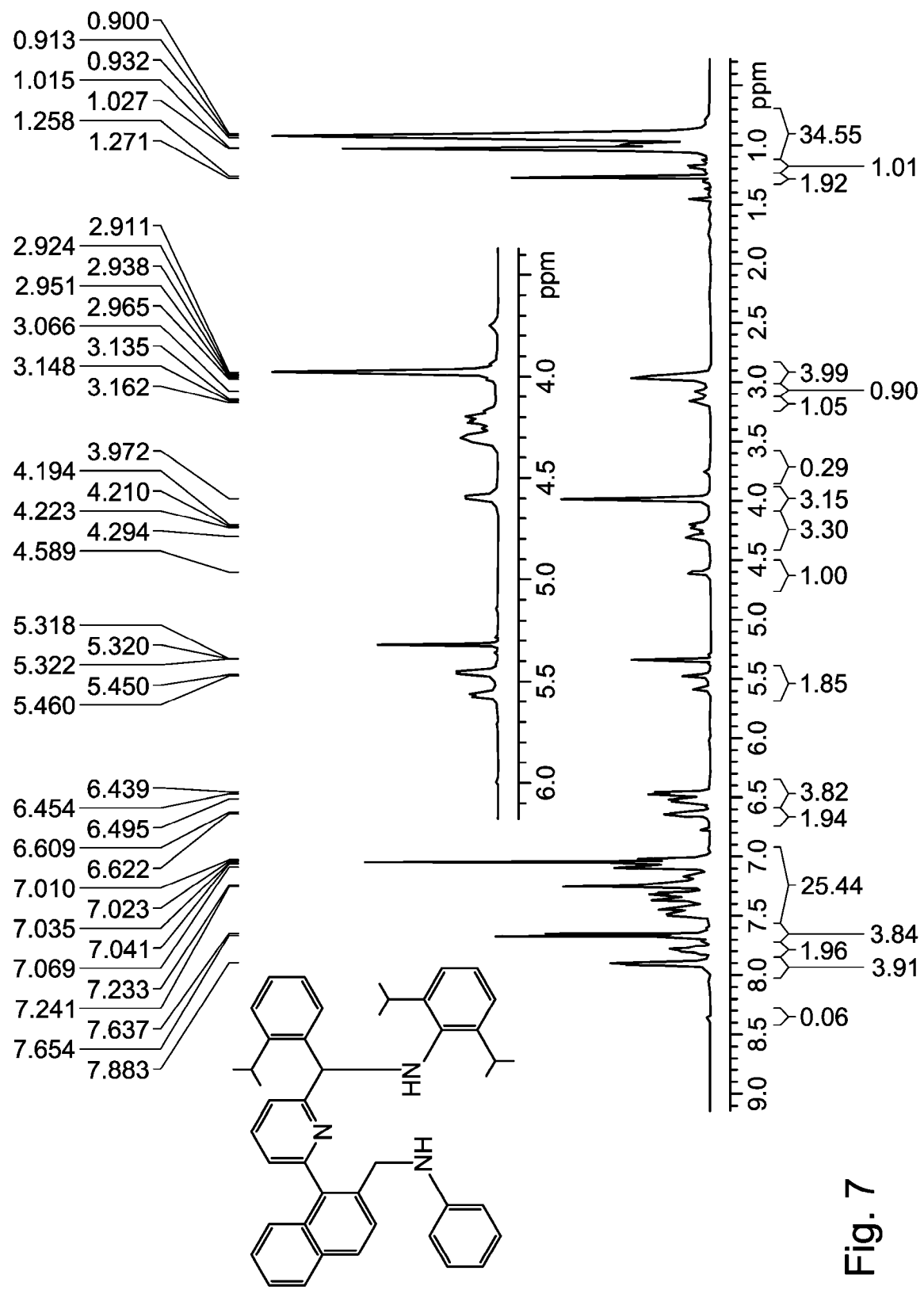
FIG. 7—$^1$H NMR spectrum of ligand 7b dissolved in $CDCl_3$.
Figure 8:
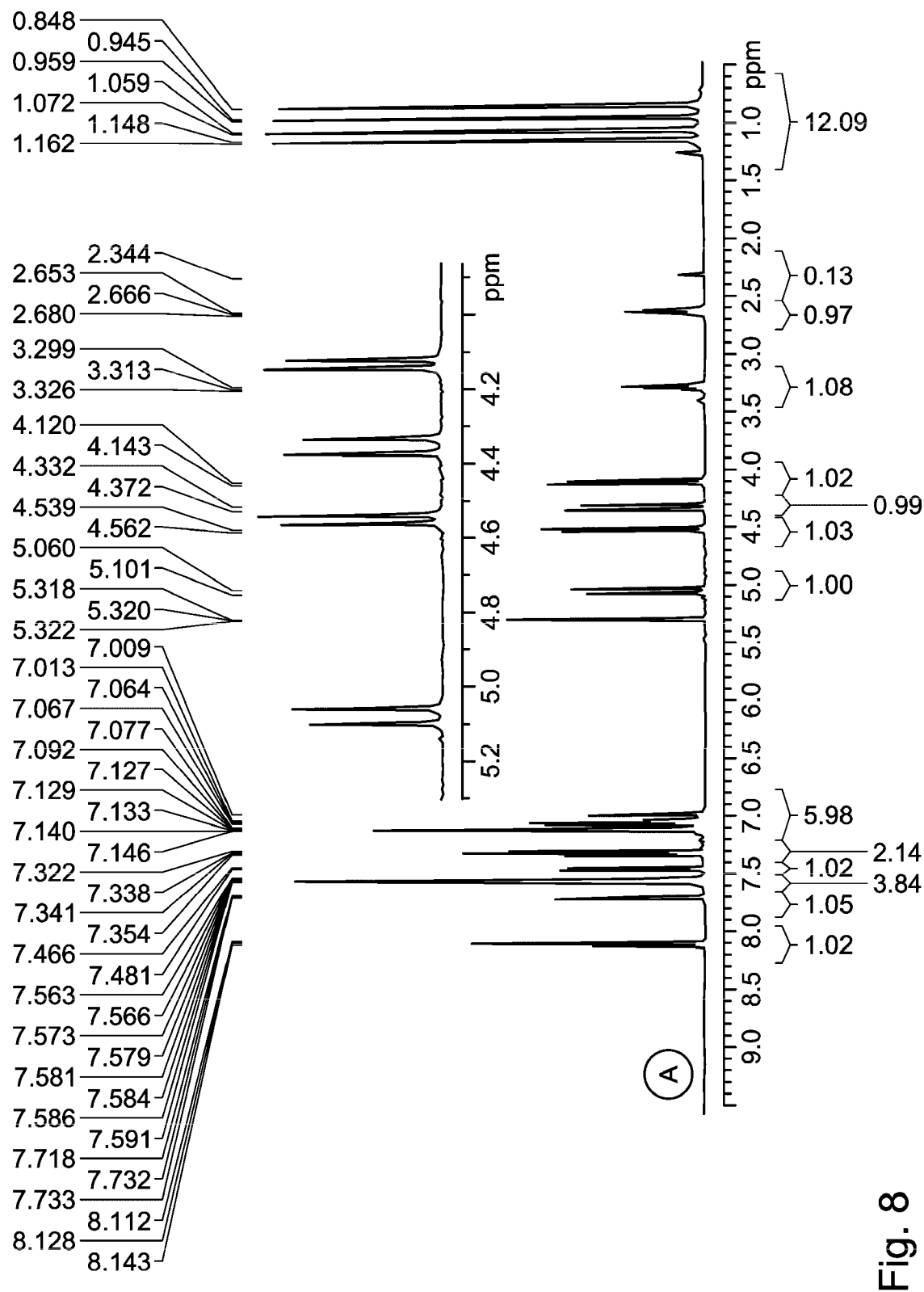
Figure 9:
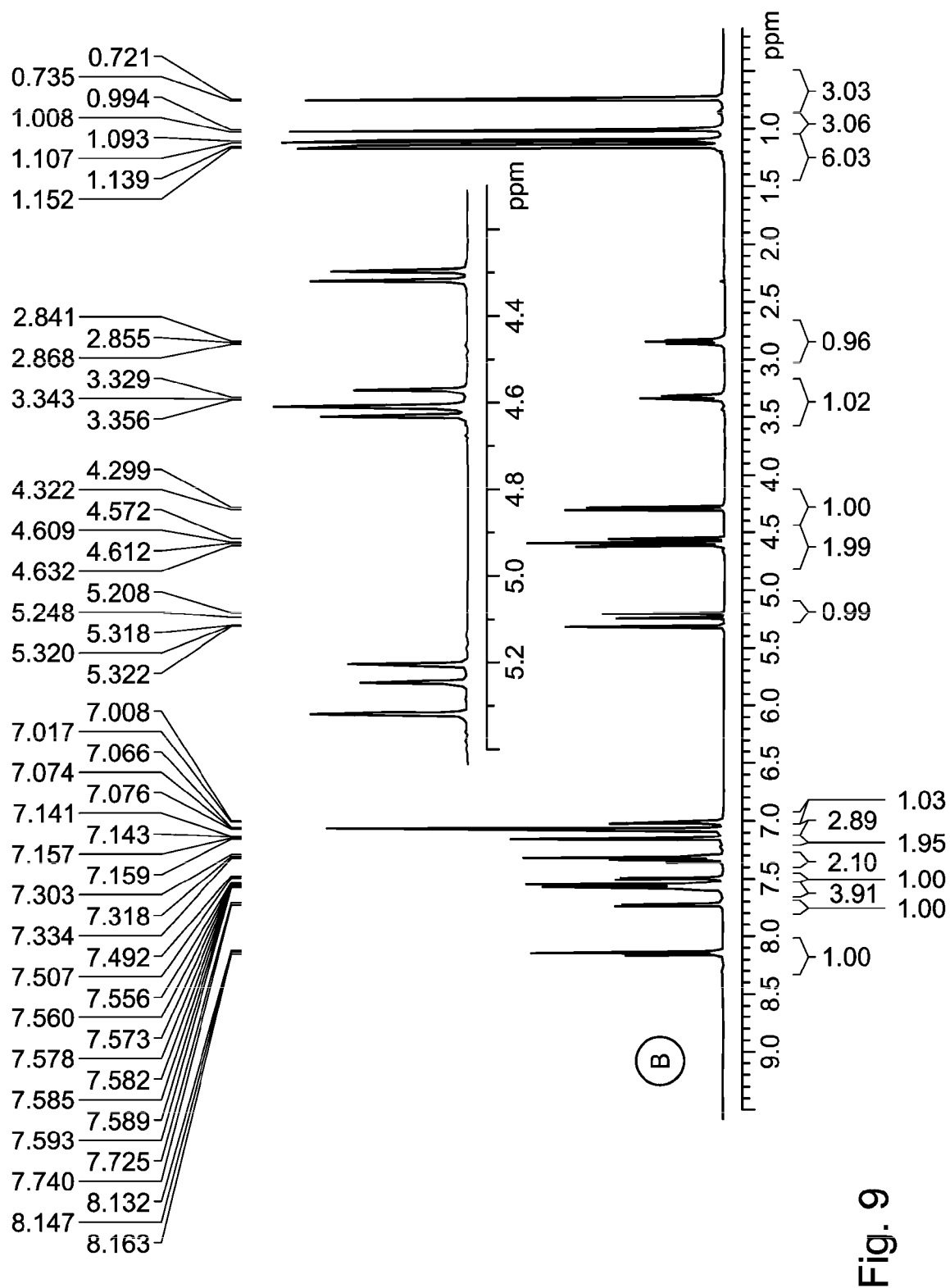
Figure 10:
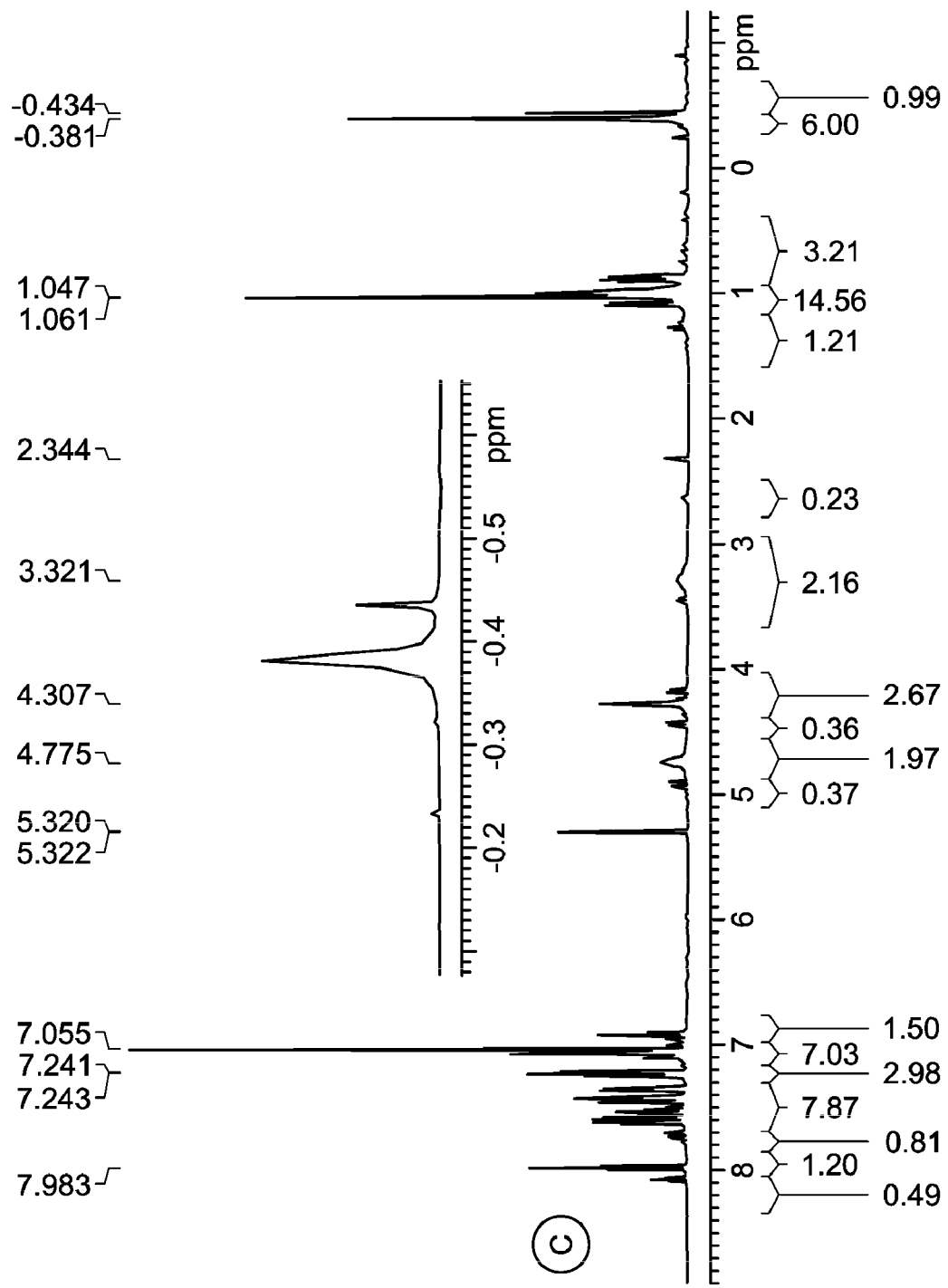
Figure 11:
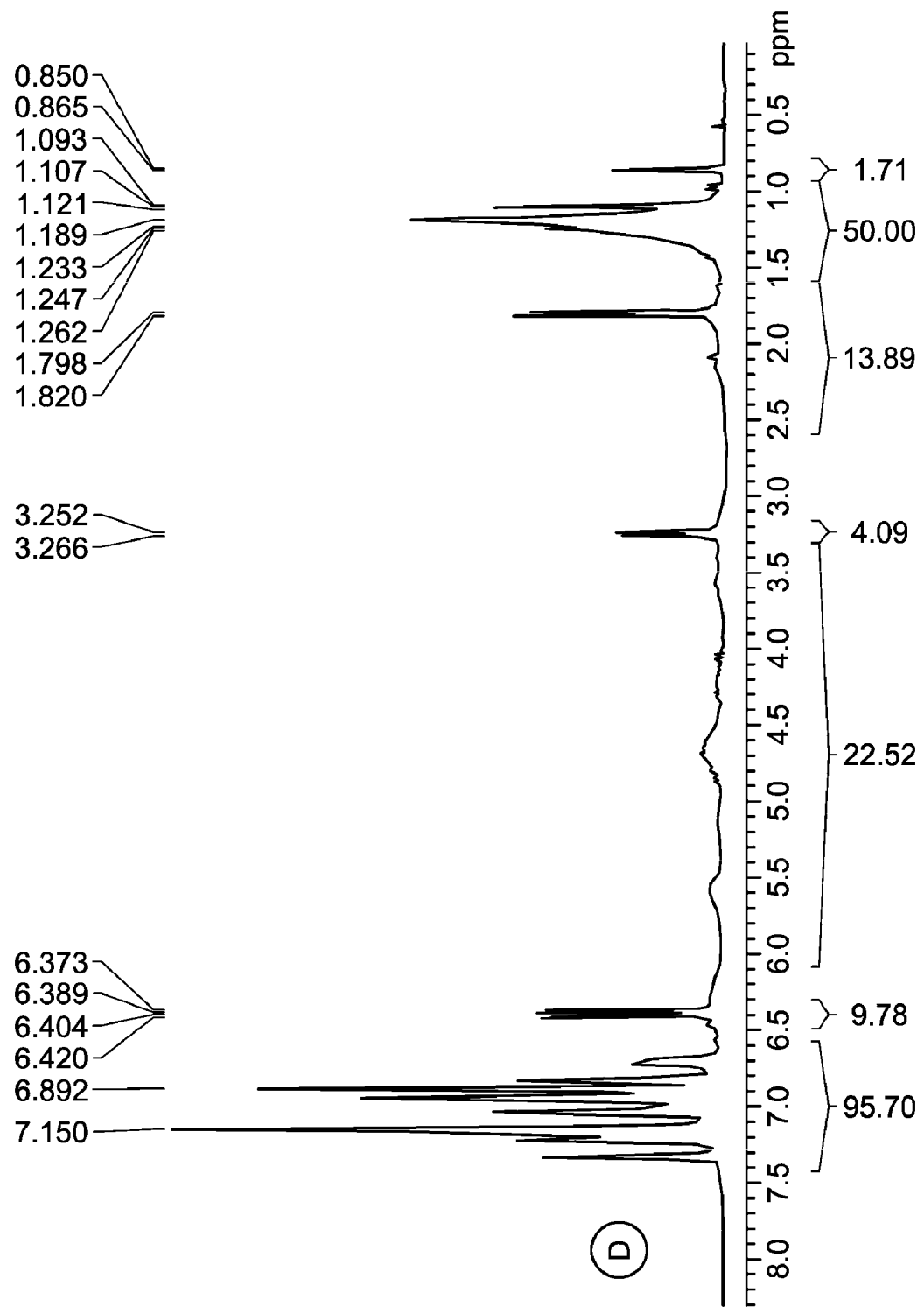
Figure 12:
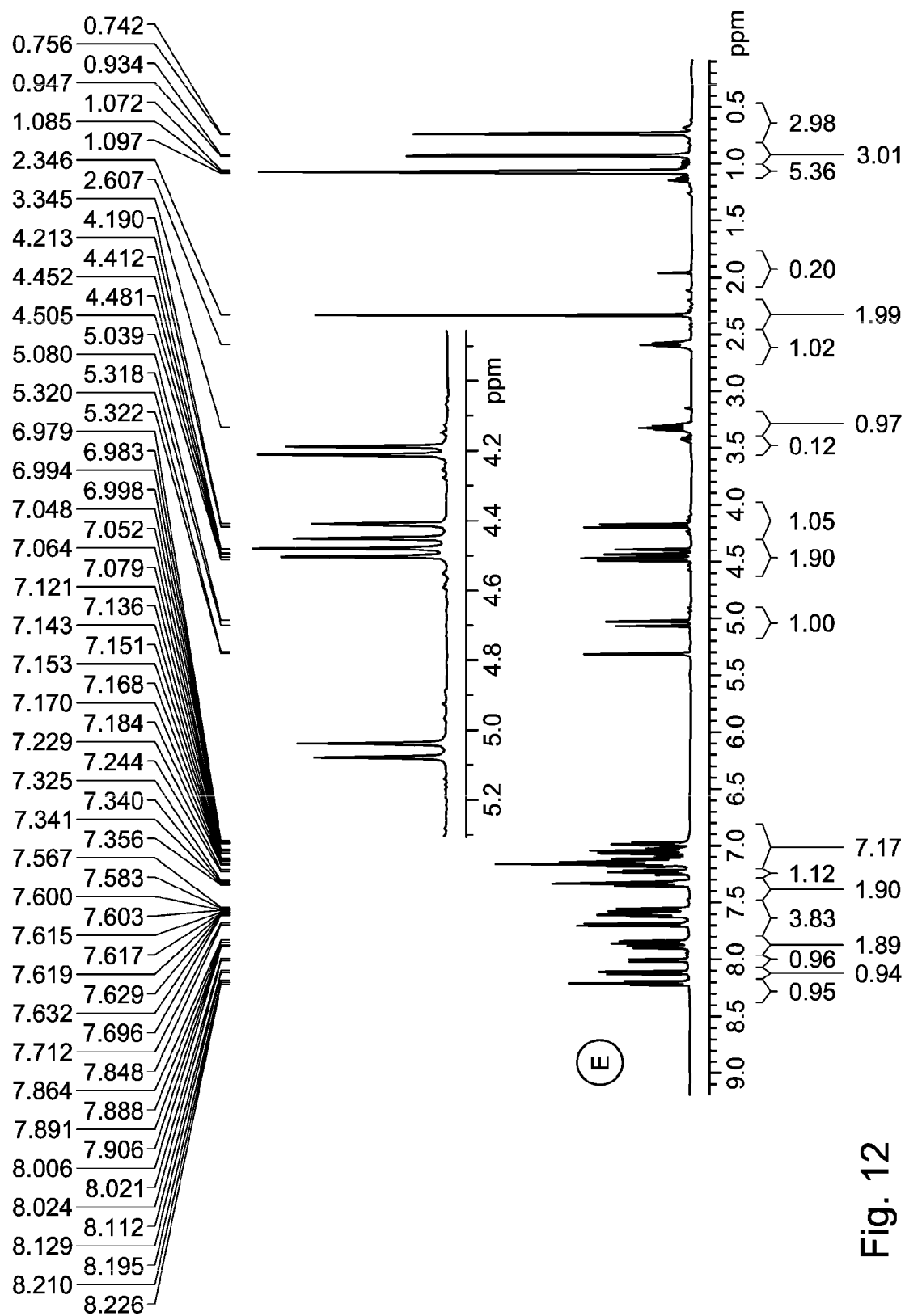
Figure 13:
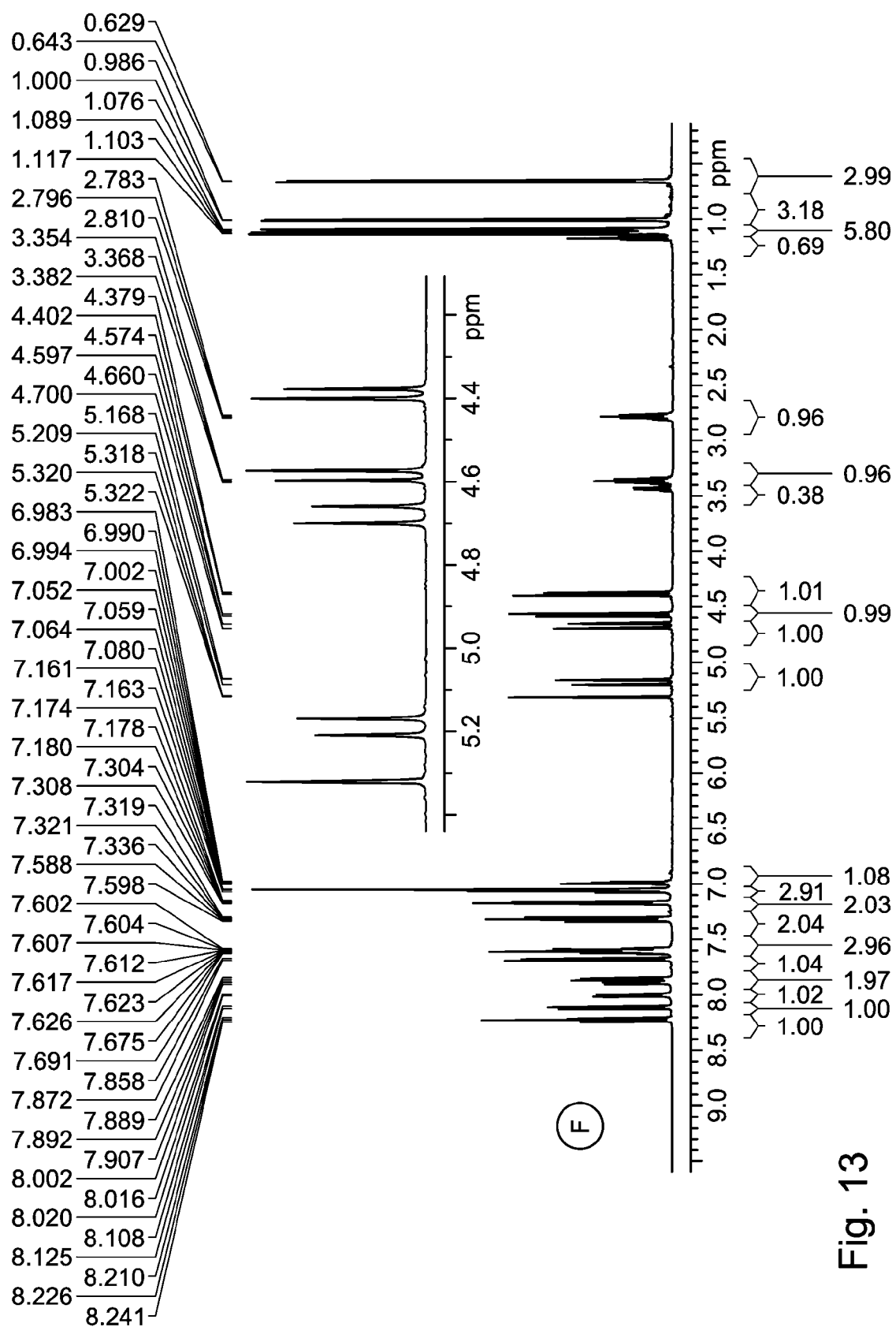
Figure 14:
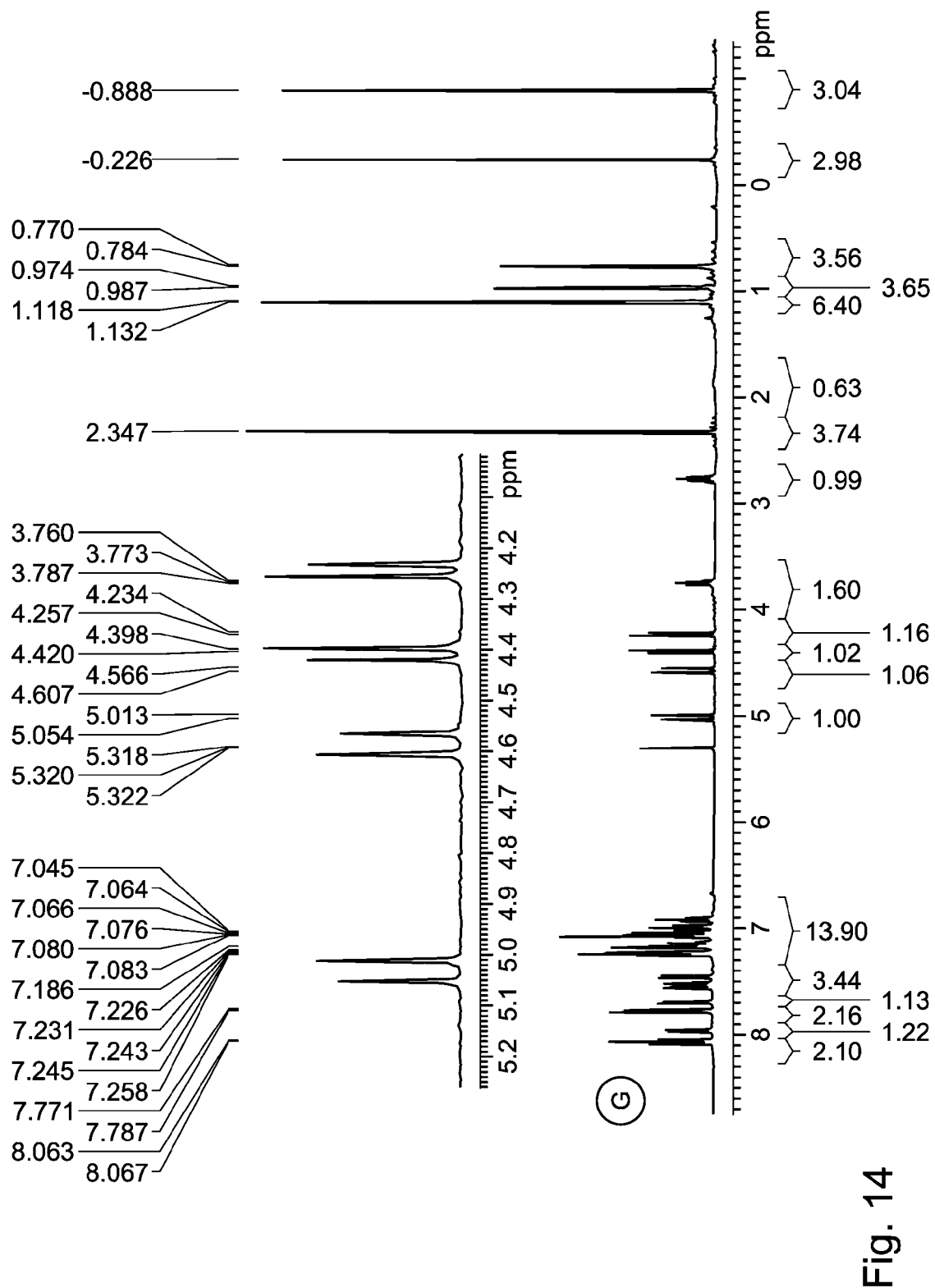
Figure 15:
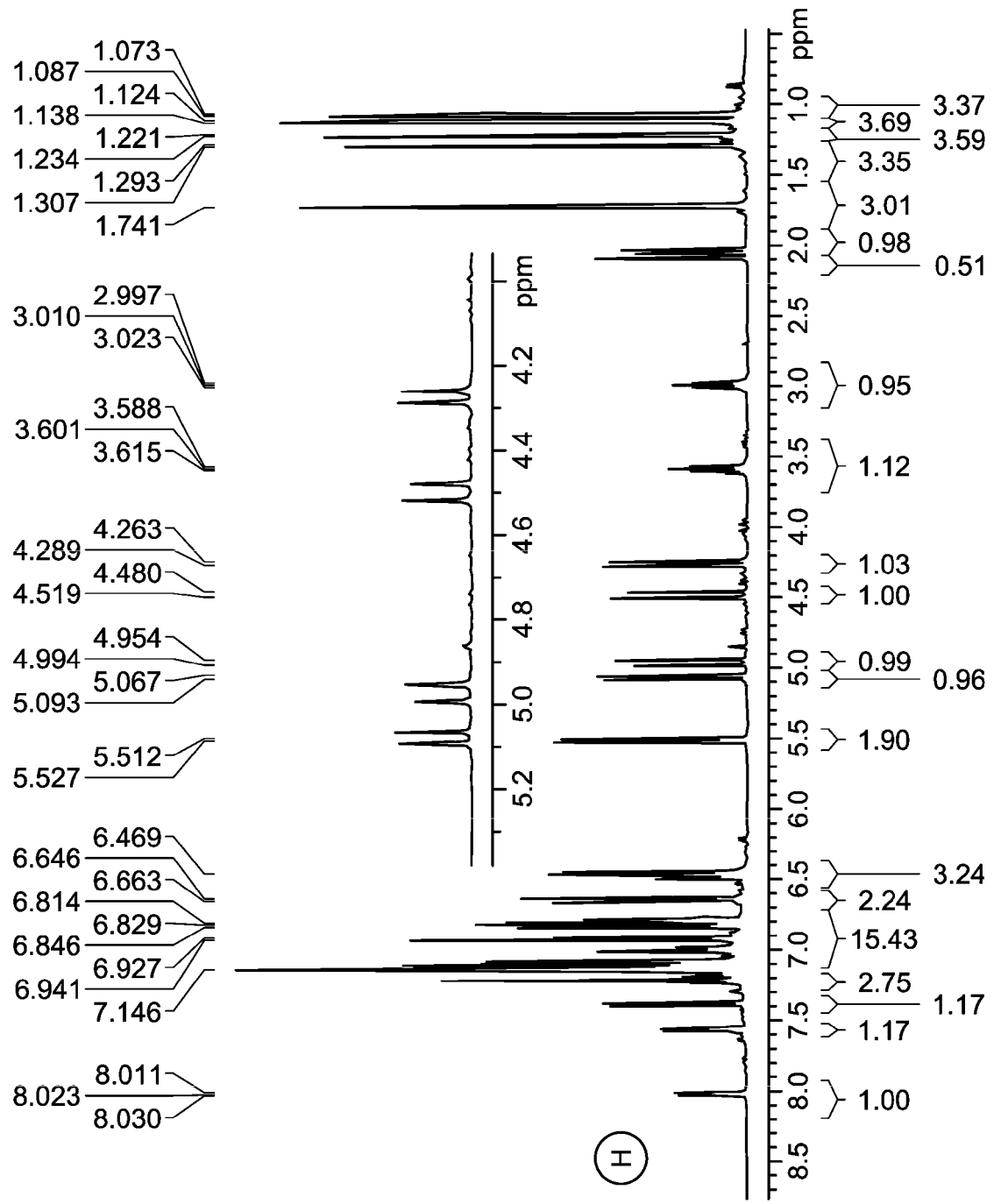
Figure 16:
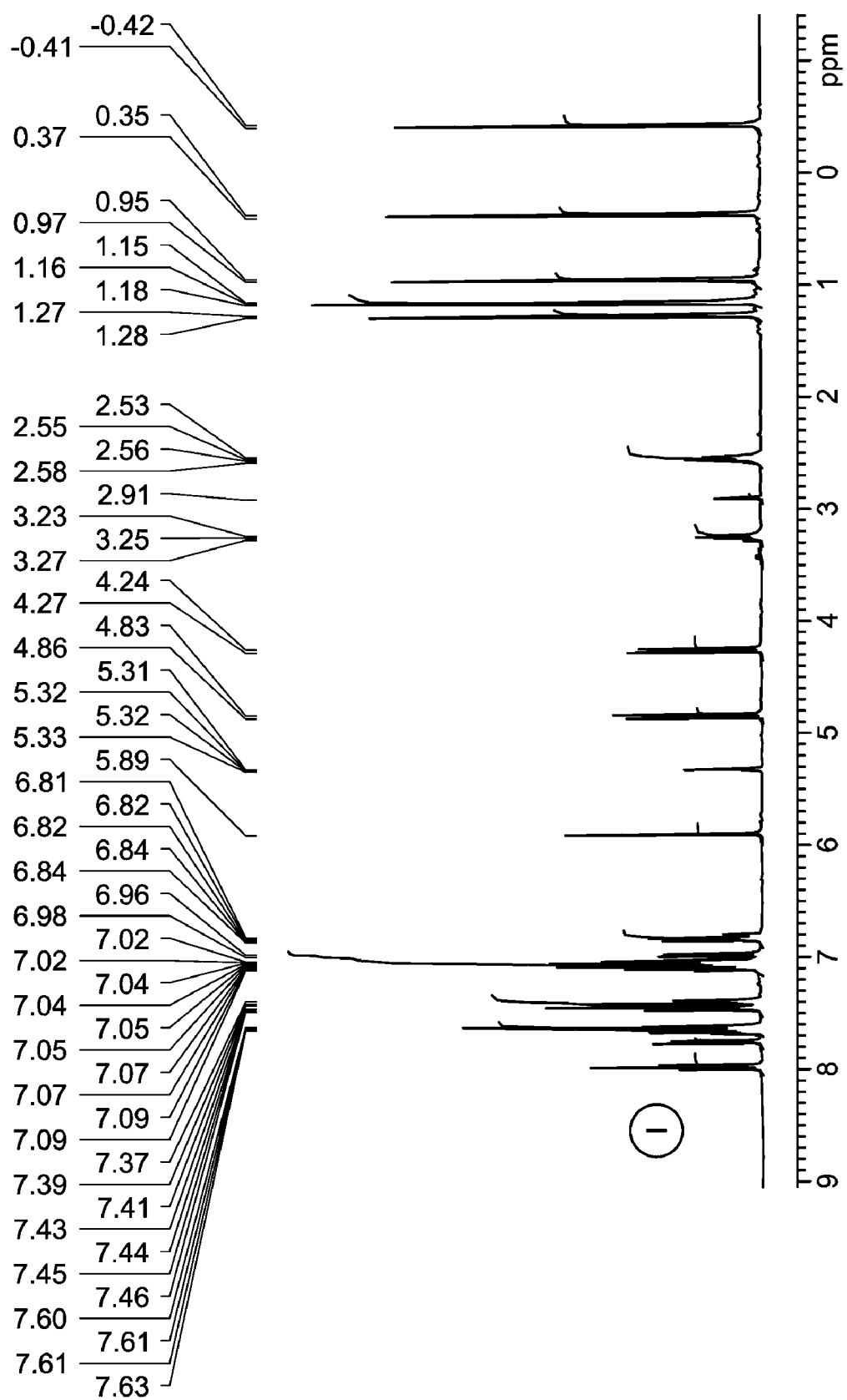
Figure 17:
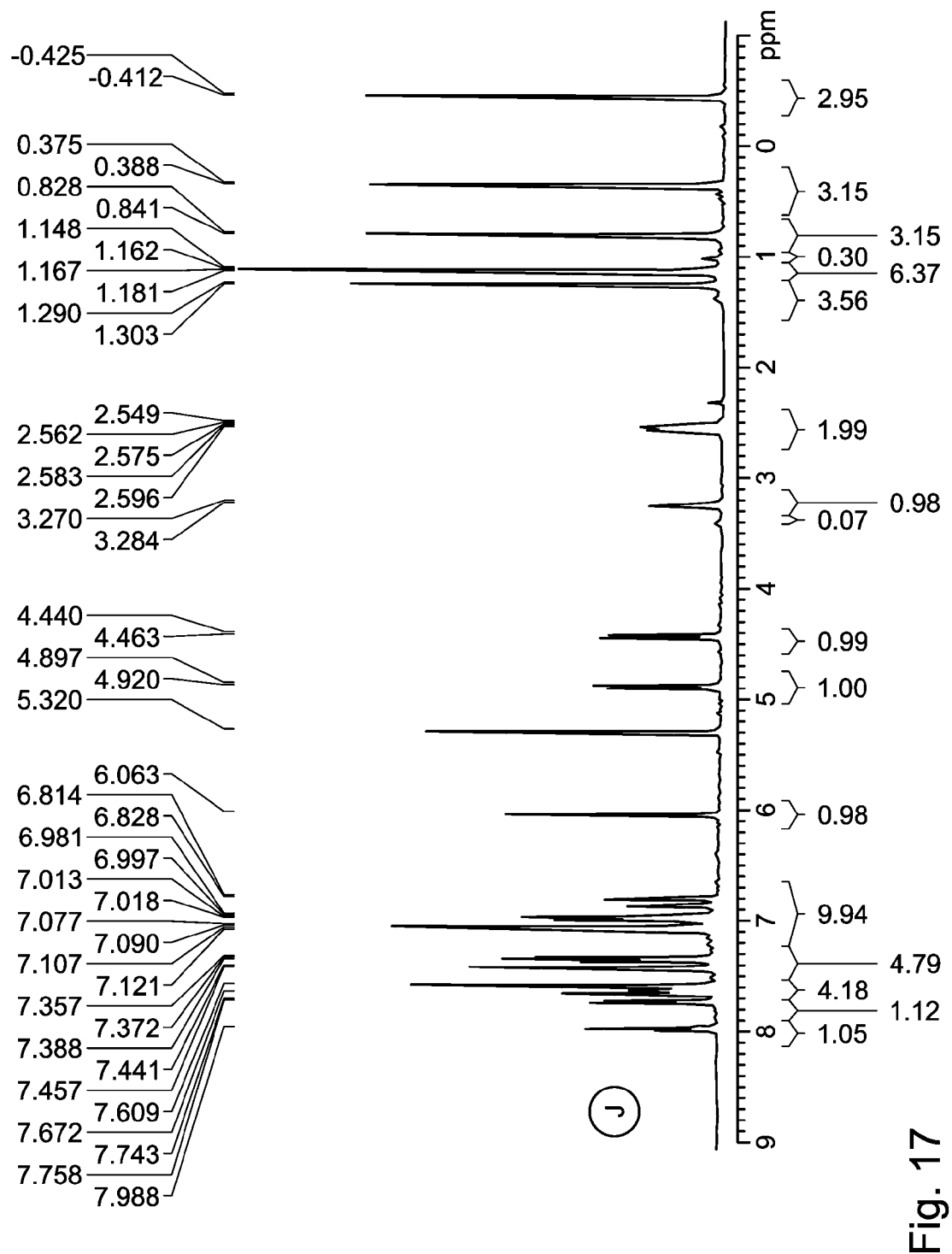
Figure 18:
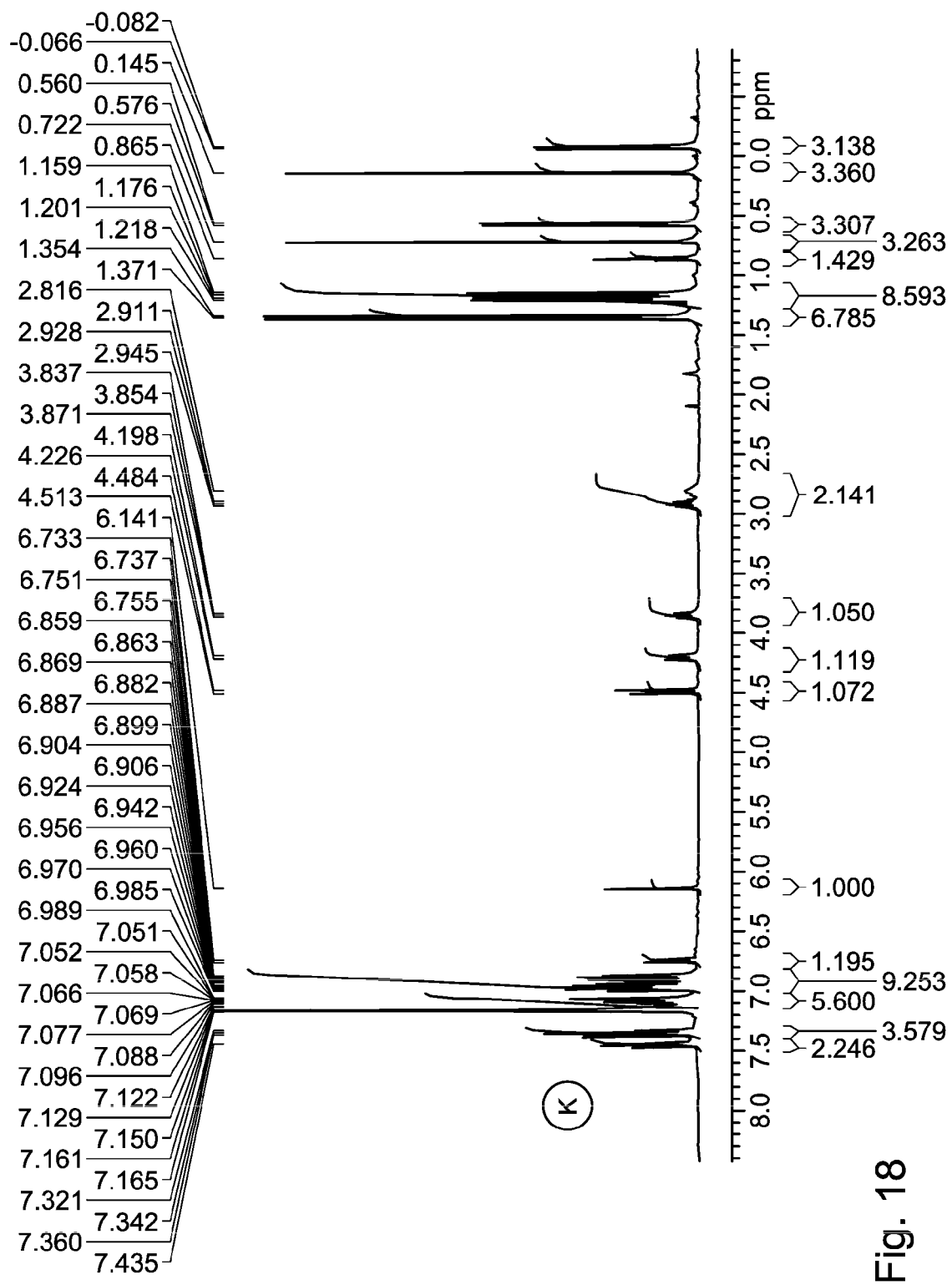

2,6-Diisopropyl-N-((2-isopropylphenyl)(6-(2-((phenylamino)methyl)naphthalen-1-yl)pyridin-2-yl)methyl)aniline (7b). Compound 5a (2.28 g, 5.18 mmol), tetrahydrofuran (50 mL), and 4 angstrom molecular sieves (ca. 20 mL) were combined. Then 2,6-diisopropylaniline (0.918 g, 5.18 mmol) and a catalytic amount of p-toluenesulfonic acid monohydrate (0.005 g, 0.03 mmol) were added. The mixture was heated to 45° C. for 14 hours. Then the mixture was filtered and fresh molecular sieves (ca. 15 mL) were added followed by additional p-toluenesulfonic acid monohydrate (0.005 g, 0.03 mmol). After heating at 50° C. for 2 hours the mixture was filtered and evaporated to a residue of the imine 6a. Then Et$_2$O (30 mL) was added, and the resulting solution was cooled to −80° C. An Et$_2$O (5 mL) solution of 2-isopropylphenyllithium (0.653 g, 5.18 mmol) was added dropwise. The mixture was then allowed to slowly warm to ambient temperature over a couple of hours. Then the mixture was poured into water (100 mL) and the organics were separated, dried over brine then magnesium sulfate, filtered, and evaporated to a residue. The residue was dissolved in chloroform (25 mL), and trifluoroacetic acid (10 mL) was added. The mixture was heated to reflux for 40 minutes, during which time gas evolved. The mixture was cooled to ambient temperature and 3 M NaOH (60 mL) was added. After stirring for several minutes, the organics were separated, dried over brine then magnesium sulfate, filtered through diatomaceous earth, and evaporated to yield the crude product. This was purified by chromatography on basic alumina using 5:1 hexanes: $CH_2Cl_2$ with an increasing gradient of ethyl acetate (1% to 10%). The product was isolated as a foam-like solid. For $^1H$ NMR (in $CD_2Cl_2$) see FIG. 4.

Tert-butyl phenyl(2-(4,4,5,5-tetramethyl-1,3,2-dioxaborolan-2-yl)benzyl)carbamate (10). Pentane (350 mL) was added to tert-butyl phenylcarbamate (20.81 g, 107.7 mmol) to form a suspension. BuLi (67.3 mL, 107.7 mmol) in hexanes was added dropwise over 1 hour. During the addition a clear solution formed briefly then a white precipitate formed. After the addition was complete the mixture was stirred for 1 hour then the solid was collected on a glass frit, washed with pentane (2×20 mL), and dried under reduced pressure to afford LiN(Boc)Ph (16.6 g, 77.4%). 2-Bromomethylphenyl boronic acid pinacol ester (compound 9) (4.66 g, 15.7 mmol) and N,N-dimethylformamide (DMF) (35 mL) were combined to form a clear colorless solution. Then solid LiN(Boc)Ph (3.13 g, 15.7 mmol) was added in small portions over three minutes. The mixture was stirred for 2 hours then the white suspension was poured into water (250 mL). $Et_2O$ (150 mL) was added and the organics were separated, dried with brine then magnesium sulfate. Filtration followed by evaporation afforded the product as a white solid. $^1H$ NMR ($CDCl_3$, 250 MHz): 7.77 (d, 1H), 7.0-7.5 (m, 8H), 5.19 (s, 2H), 1.39 (s, 9H), 1.27 (s, 12H).

tert-Butyl 2-(6-formylpyridin-2-yl)benzyl(phenyl)carbamate (11). A mixture of water (160 mL) and methanol (40 mL) was combined with sodium carbonate (3.80 g, 35.9 mmol), and the mixture was sparged with nitrogen for 30 min. In a separate flask were combined, under nitrogen, 6-bromo-2-pyridinecarboxaldehyde (2.67 g, 14.4 mmol), tert-butyl phenyl(2-(4,4,5,5-tetramethyl-1,3,2-dioxaborolan-2-yl)benzyl)carbamate (5.87 g, 14.4 mmol), tetrakis(triphenylphosphinio)palladium (0.829 g, 0.718 mmol), and toluene (150 mL). The water-methanol solution was added via cannula to the toluene solution, and the biphasic mixture was heated to 80° C. overnight. At this time $^1H$ NMR spectroscopic analysis of an aliquot indicated that the reaction was complete. The clear yellow organic layer was separated, dried with brine, then over magnesium sulfate. The crude product was purified by chromatography on silica using 1:1 hexanes:dichloromethane elutant and increasing the strength by addition of up to 10% EtOAc. The product was isolated as a sticky oil (4.7 g, 840%). $^1H$ NMR ($CD_2Cl_2$, 500 MHz): 10.0 (s, 1H), 7.83-7.92 (m, 2H), 7.56 (d, 1H), 7.50 (d, 1H), 7.44 (m, 1H), 7.36 (m, 2H), 7.17 (t, 2H), 7.01 (t, 1H), 7.0 (br d, 2H), 5.11 (s, 2H), 1.34 (s, 9H).

(E)-tert-Butyl 2-(6-((2,6-diisopropylphenylimino)methyl) pyridin-2-yl)benzyl(phenyl)carbamate (12). Tetrahydrofuran (50 mL) and 4 angstrom molecular sieves (ca. 15 mL) were added to tert-butyl 2-(6-formylpyridin-2-yl)benzyl(phenyl) carbamate (11) (03.63 g, 9.34 mmol). Then 2,6-diisopropylaniline (1.66 g, 9.34 mmol) was added followed by a catalytic amount of p-toluenesulfonic acid monohydrate (0.003 g, 0.015 mmol). The mixture was stirred overnight then filtered and evaporated to a thick yellow oil. After several days the oil began to crystallize. Methanol (40 mL) was added and the mixture was stirred to give a yellow crystalline solid. The mixture was cooled to 5° C. for a couple of hours then the solid was collected on a glass fit and dried under reduced pressure. Yield: 3.93 g, 76.8%. $^1H$ NMR ($CD_2Cl_2$, 500 MHz): 8.26 (s, 1H), 8.19 (d, 1H), 7.87 (t, 1H), 7.54 (d, 1H), 7.32-7.42 (m, 4H), 7.02-7.20 (m, 8H), 5.11 (s, 2H), 2.99 (sept, 2H), 1.34 (s, 9H), 1.18 (d, 12H).

2,6-Diisopropyl-N-((6-(2-((phenylamino)methyl)phenyl) pyridin-2-yl)methyl)aniline (13a). Methanol (40 mL) and (E)-tert-butyl 2-(6-((2,6-diisopropylphenylimino)methyl) pyridin-2-yl)benzyl(phenyl)carbamate (12) (2.56 g (4.67 mmol) were combined to form a yellow suspension. Then some $NaBH_3CN$ (0.293 g, 4.66 mmol) was added followed by four drops of 88% formic acid. Then additional $NaBH_3CN$ (0.878 g, 14.0 mmol) was added in small portions over 5 minutes. The mixture was heated to reflux for 3 hours then evaporated to near dryness. Water (20 mL) and $Et_2O$ (40 mL) were then added followed by a $CH_2Cl_2$ (6 mL). The organics were separated, dried over brine then magnesium sulfate, filtered, and evaporated to a thick oil. Chloroform (25 mL) was then added to form a solution. Trifluoroacetic acid (10 mL) was added and the mixture was heated to reflux to cause gas evolution. After 45 minutes the mixture was cooled to ambient temperature and 3 M NaOH (60 mL) was added. The biphasic mixture was rapidly stirred for several minutes. The organics were separated, washed with water (50 mL) and brine (5 mL). The organics were then separated and dried over magnesium sulfate. Filtration and evaporation afforded the product as a thick oil that was dried thoroughly under reduced pressure at 65° C. Yield: 2.0 g, 95%). $^1H$ NMR ($CD_2Cl_2$, 500 MHz): 7.77 (t, 1H), 7.39-7.58 (m, 5H), 7.31 (d, 1H), 7.02-7.12 (m, 5H), 6.63 (t, 1H), 6.58 (d, 2H), 4.62 (br, 1H), 4.41 (br, 2H), 4.23 (br, 1H), 3.97 (br, 1H), 3.35 (sept, 2H), 1.20 (d, 12H).

2,6-Diisopropyl-N-((2-isopropylphenyl)(6-(2-((phenylamino)methyl)phenyl)pyridin-2-yl)methyl)aniline (13b). $Et_2O$ (30 mL) and (E)-tert-butyl 2-(6-((2,6-diisopropylphenylimino)methyl)pyridin-2-yl)benzyl(phenyl)carbamate (12) (1.07 g (1.96 mmol) were combined to form a clear yellow solution. At −80° C. an $Et_2O$ (3 mL) solution of 2-isopropylphenyllithium (0.247 g, 1.96 mmol) was added dropwise over a few minutes. The mixture was clear red-orange. The mixture was allowed to slowly warm to ambient temperature. After stirring overnight water (20 mL) was added and the organic layer was separated. The organics were dried with brine, then over magnesium sulfate. Filtration and evaporation afforded a residue that was dissolved in $CHCl_3$ (10 mL). Trifluoroacetic acid (4 mL) was then added and the mixture was heated to reflux for 45 minutes during which time gas evolved. At ambient temperature 3 M NaOH (30 mL) was added and the biphasic mixture was stirred rapidly. Then $Et_2O$ (40 mL) was added and the organics were separated, dried with brine, dried over magnesium sulfate, filtered, then evaporated to a thick oil. The product was dried thoroughly under reduced pressure. Yield: 1.16 g, 104%). $^1H$ NMR ($CD_2Cl_2$, 500 MHz): 7.66-7.73 (pseudo quartet, 2H), 7.32-7.50 (m, 5H), 7.15-7.26 (m, 4H), 6.96-7.05 (m, 5H), 6.58 (t, 1H), 6.37 (d, 2H), 5.49 (s, 1H), 4.22 (4H, m), 3.05 (sept, 1H), 2.87 (sept, 2H), 0.97 (d, 12H), 0.92 (d, 3H), 0.90 (d, 3H).

Synthesis of Pyridyl Diamide Metal Complexes

Figure 19:
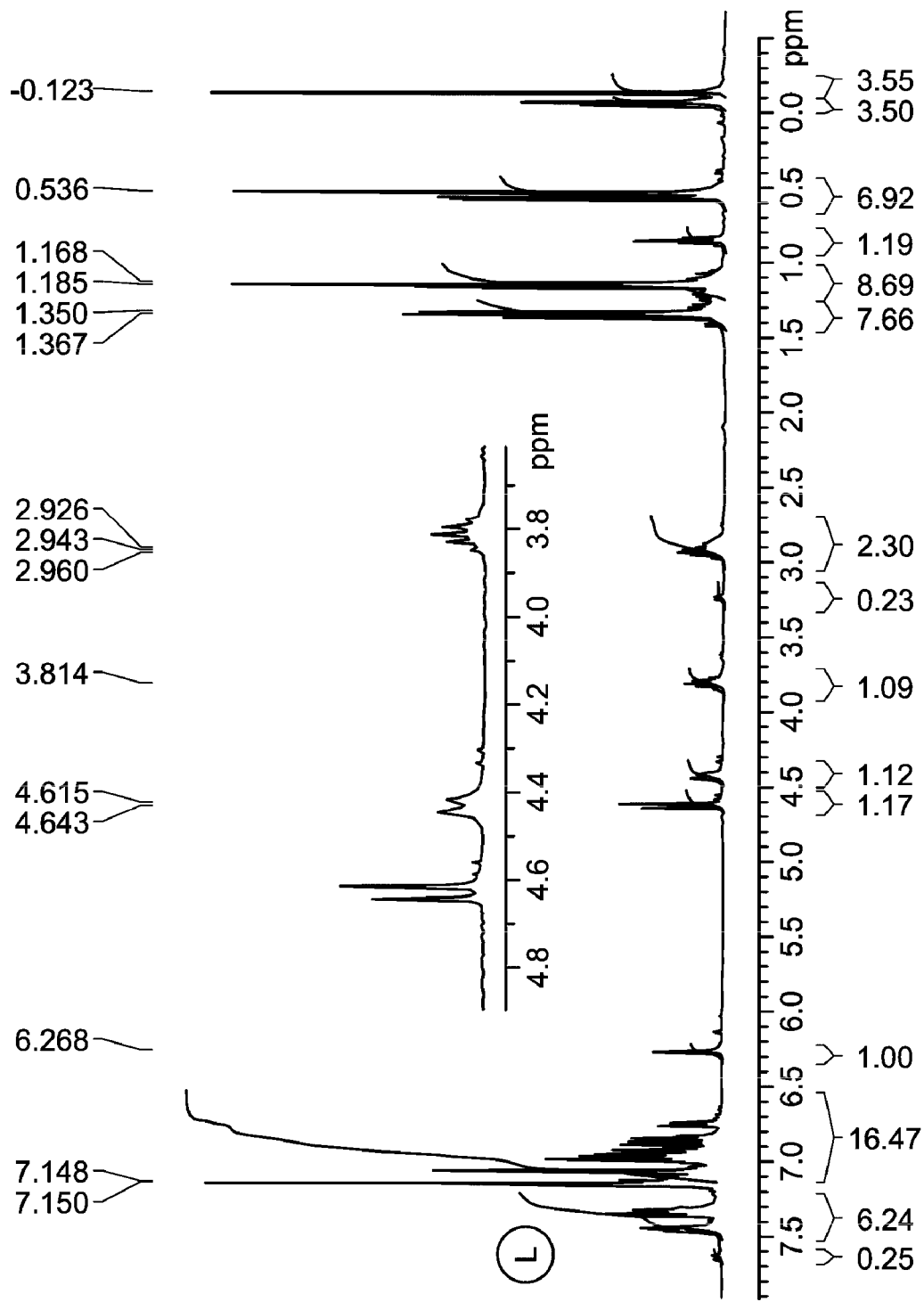
Figure 20:
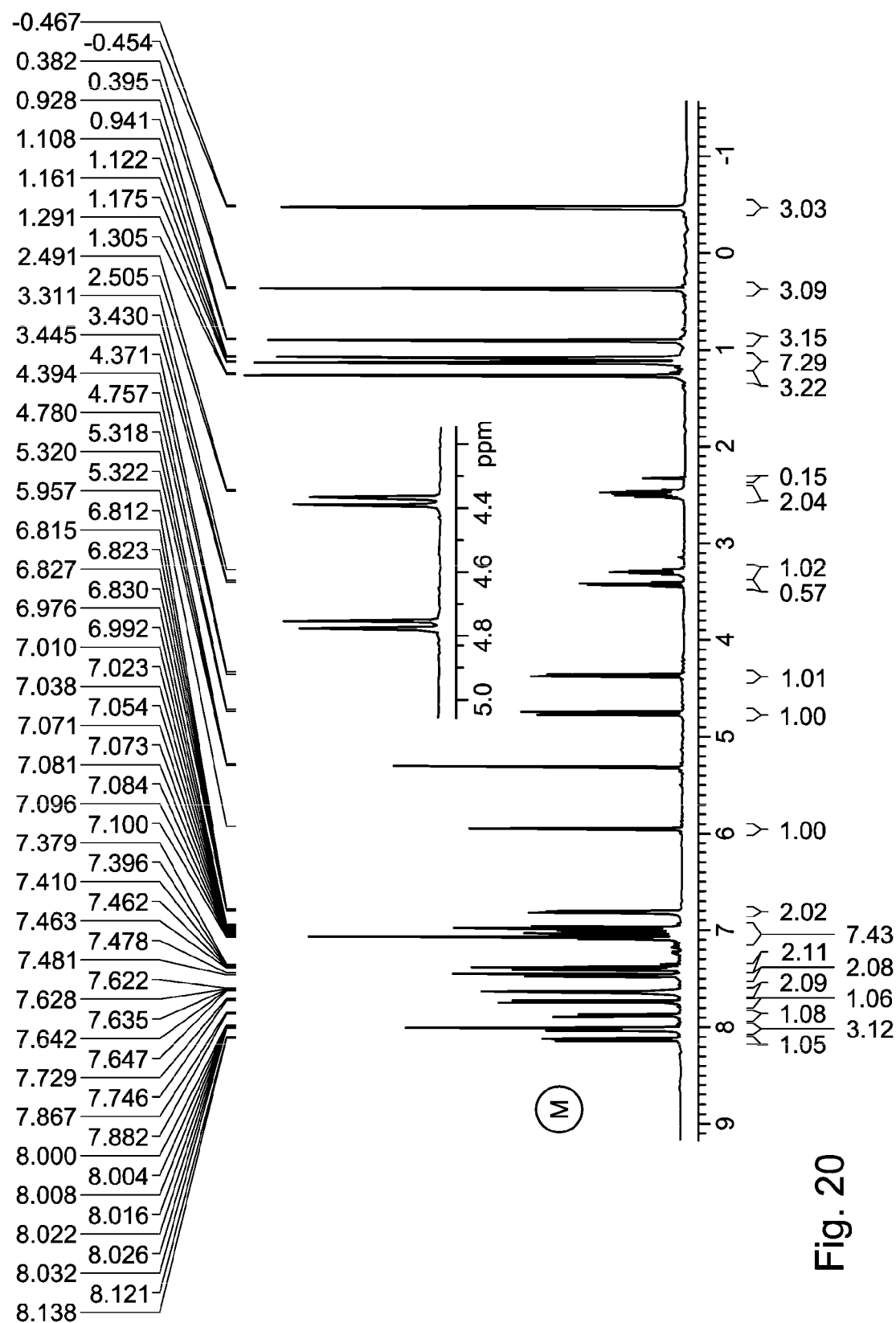
Figure 21:
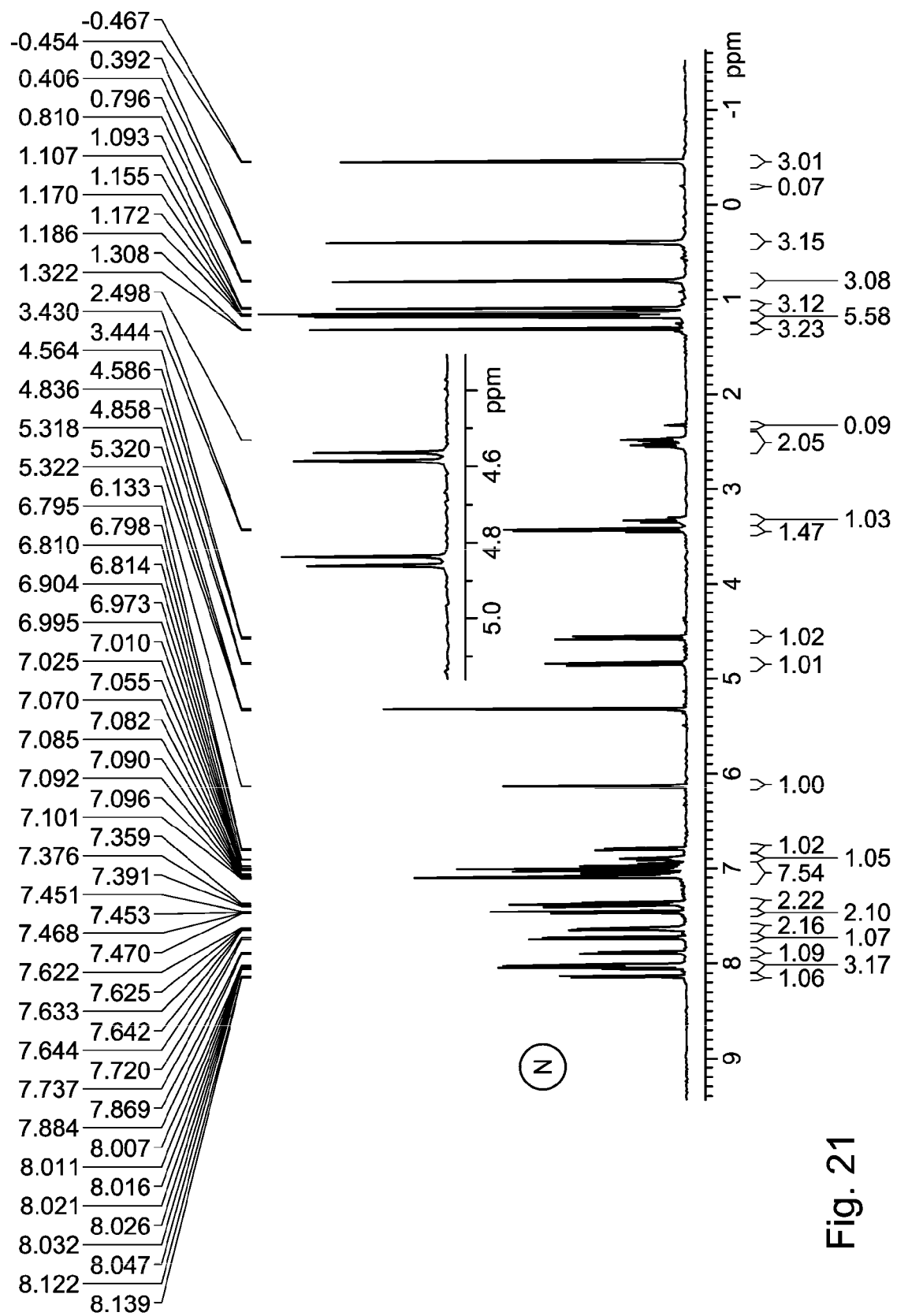
Figure 22:
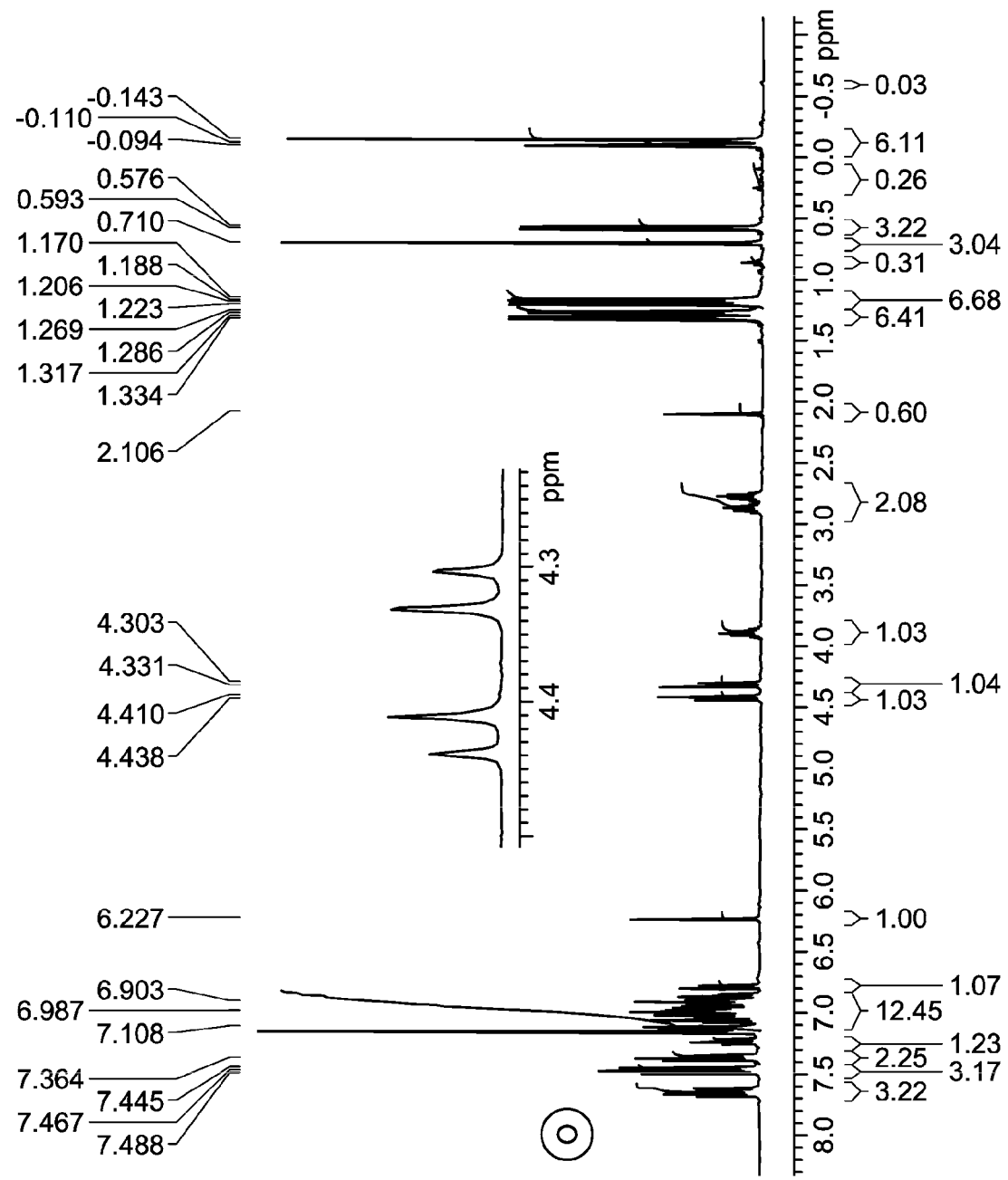
Figure 23:
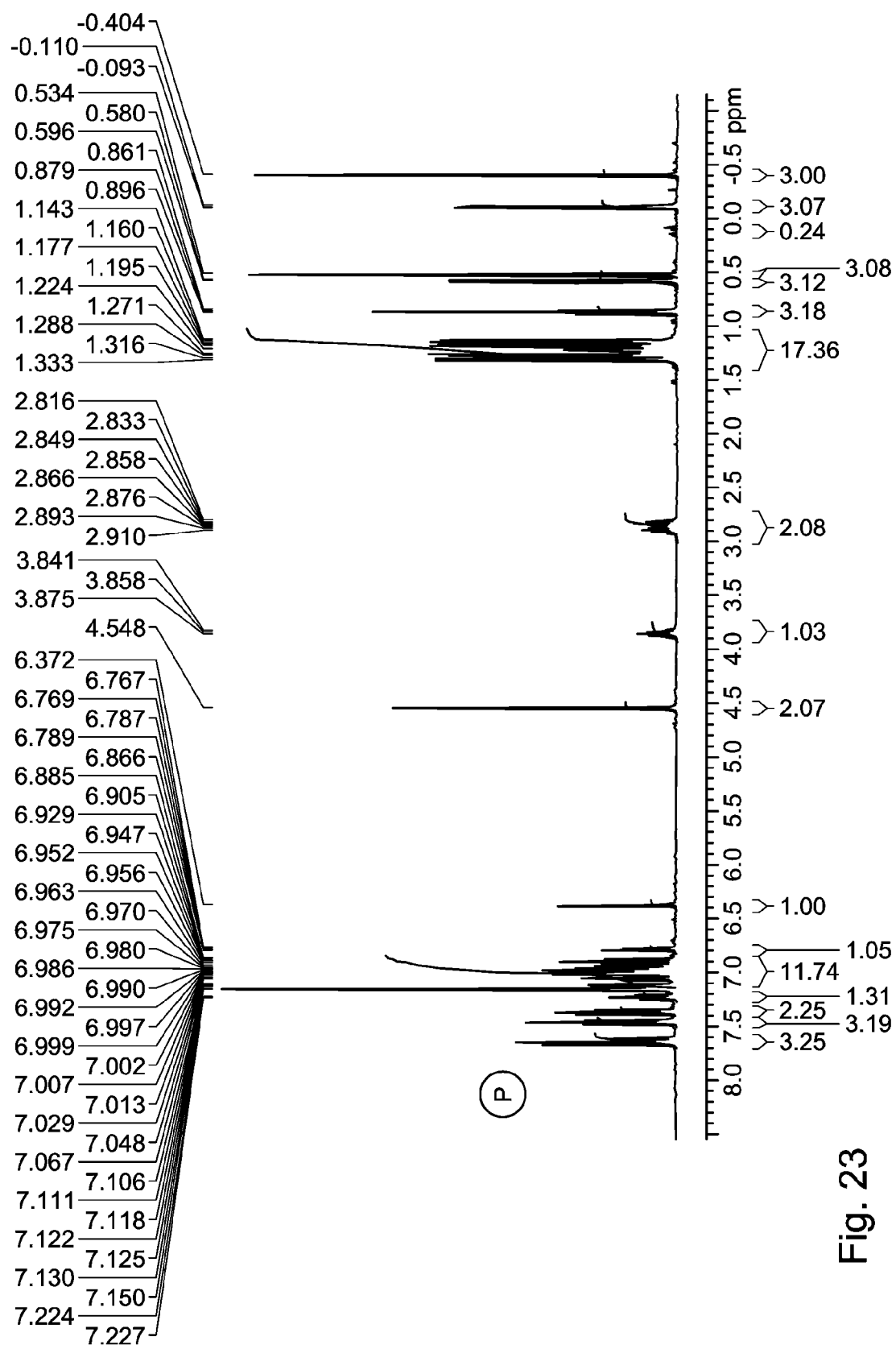

Shown below in Table 1 are 14 examples of pyridyl diamide metal complexes. They were prepared using a few different routes which are described in more detail below. The $^1H$ NMR spectra for complexes A through T are shown in FIGS. 5-18 and molecular structures for complexes D and H are shown in FIG. 19. Complexes A, B, C, D, D-Me, Q, and R are not part of the invention and are for comparative purposes only.

TABLE 1

Pyridyl diamide complexes.

| Complex | M  | X  | R¹² | R¹⁷ | LINKER |
|---------|----|----|------|------|---------|
| A*      | Zr | Cl | H    | H    | phenyl  |
| B*      | Hf | Cl | H    | H    | phenyl  |
| C*      | Zr | Me | H    | H    | phenyl  |
| D*      | Hf | Bn | H    | H    | phenyl  |
| D-Me*   | Hf | Me | H    | H    | phenyl  |
| E       | Zr | Cl | H    | H    | naphthyl |
| F       | Hf | Cl | H    | H    | naphthyl |
| G       | Zr | Me | H    | H    | naphthyl |
| H       | Hf | Bn | H    | H    | naphthyl |
| H-Me    | Hf | Me | H    | H    | naphthyl |
| I       | Zr | Cl | 2-iPrPh | H | phenyl  |
| J       | Hf | Cl | 2-iPrPh | H | phenyl  |
| K       | Zr | Me | 2-iPrPh | H | phenyl  |
| L       | Hf | Me | 2-iPrPh | H | phenyl  |
| M       | Zr | Cl | 2-iPrPh | H | naphthyl |
| N       | Hf | Cl | 2-iPrPh | H | naphthyl |
| O       | Zr | Me | 2-iPrPh | H | naphthyl |
| P       | Hf | Me | 2-iPrPh | H | naphthyl |
| Q*      | Zr | Cl | H    | Ph   | phenyl  |
| R*      | Hf | Cl | H    | Ph   | phenyl  |
| S       | Zr | Cl | H    | Ph   | naphthyl |
| T       | Hf | Cl | H    | Ph   | naphthyl |

LINKER: phenyl

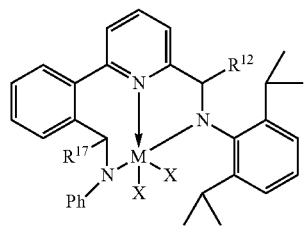

LINKER: naphthyl

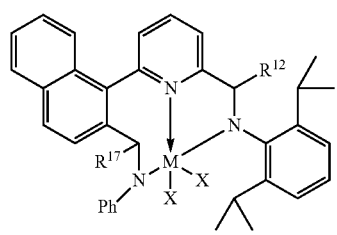

Synthesis of pyridyl diamide metal dichloride complexes. Complexes A, B, E, F, I, J, M, and N were prepared using the general methodology described in the next two following examples. Both examples involve the reaction of a pyridyl diamine with a suitable organometallic reagent containing two basic ligands that deprotonate the pyridyl diamine and form leaving groups, which are subsequently removed. Alternatively, the synthesis of pyridyl diamide metal dichloride complexes may likely be accomplished by the initial deprotonation of a pyridyl diamine followed by a salt metathesis reaction with a group 4 metal chloride.

Complex I. Toluene (6 mL) was added to 2,6-diisopropyl-N-((2-isopropylphenyl)(6-(2-((phenylamino)methyl)phenyl)pyridin-2-yl)methyl)aniline (13b) (0.328 g, 0.578 mmol) and Zr(NMe₂)₂Cl₂(dme) (dme=1,2-dimethoxyethane) (0.197 g, 0.578 mmol). The mixture was heated to 100° C. for 2 hours. The volatiles were then evaporated and Et₂O (3 mL) was added to the residue. The resulting yellow solid was collected on a glass fit, washed with Et₂O (2 mL), and pentane (10 mL), and then dried under reduced pressure. Yield 0.281 g, 66.8%.

Complex N. Benzene (4 mL) was added to 2,6-diisopropyl-N-((2-isopropylphenyl)(6-(2-((phenylamino)methyl)naphthalen-1-yl)pyridin-2-yl)methyl)aniline (7b) (0.254 g, 0.411 mmol) and HfBn₂Cl₂(OEt₂)ₙ (0.232 g, 0.411 mmol) to give a clear yellow solution. The mixture was heated to 70° C. for 5 hours. The volatiles were then evaporated and the resulting solid was dried under reduced pressure. The solid was stirred in Et₂O (4 mL), collected on a glass fit, and dried under reduced pressure. Yield 0.263 g, 74.0%.

Synthesis of pyridyl diamide metal dimethyl complexes. Complexes C, D-Me, G, H-Me, K, L, O, and P were all prepared using the general methodology described in the following example. The example involves the salt-metathesis reaction of a pyridyl diamide metal dichloride complex with a suitable main-group metal reagent (e.g., MeLi, Me₂Mg, MeMgBr, MeMgI) to form the pyridyl diamide metal dimethyl complex and a salt byproduct.

Complex O. Et₂O (8 mL) was added to complex M (0.114 g, 0.147 mmol) to form a bright yellow suspension. An Et₂O solution of MeLi (0.196 mL, 0.308 mmol) was then added dropwise. After 15 minutes the mixture was concentrated and benzene (6 mL) was added. After 2 hours it was evaporated to a yellow solid with a little brown residue. The solid was washed with Et₂O (2 mL) and extracted into benzene (6 mL). Filtration and evaporation afforded a solid. The crude product was crystallized from a toluene (3 mL) that had pentane added by vapor diffusion. Product isolated as yellow crystals that were dried under reduced pressure (0.045 g, 42%).

Synthesis of pyridyl diamide metal dibenzyl complexes. Complexes D and H were similarly prepared by reaction of the pyridyl diamine ligand with HfBn₄. The general methodology is described in the following example.

Complex H. Benzene (5 mL) was added to HfBn₄ (0.171 g, 0.315 mmol) and 2,6-diisopropyl-N-((6-(2-((phenylamino)methyl)naphthalen-1-yl) pyridin-2-yl)methyl)aniline (7a) (0.158 g, 0.315 mmol). The slightly cloudy yellow solution was heated to 50° C. After 4 hours the volatiles were evaporated to give a solid that was extracted with Et₂O (20 mL) and filtered. Concentration to 7 mL and cooling to −10° C. overnight afforded yellow crystals (0.12 g) of product that were isolated and dried under reduced pressure. A second crop formed upon concentration and cooling of the mother liquor. Total yield: 0.182 g, 67.3%.

Synthesis of pyridyl diamide metal dichloride complexes with substitution at RIO position. Complexes Q, R, S, and T were prepared using the general methodology described in the following example which involves the reaction of PhN═CHPh with a cyclometalated pyridyl amide intermediate. This general route was described in WO2010/011435 A1.

Complex Q. The pyridyl amine ligand 2,6-diisopropyl-N-((6-phenylpyridin-2-yl) methyl)aniline (0.568 g, 1.65 mmol) was combined with ZrBn₂Cl₂(OEt₂) (0.690 g, 1.65 mmol) in a 20 mL vial. Then CH₂Cl₂ (10 mL) was added to form a clear orange solution. The vial was capped and heated to 45° C. After 2 hours the mixture was evaporated to a sticky solid. Et₂O (5 mL) was added and the resulting solid was collected on a fit and washed with additional Et₂O (5 mL). The yellow solid was dried under reduced pressure to afford 0.82 g (86% yield) of intermediate U that contained one coordinated ether molecule per pyridyl amide. A portion of intermediate U (0.1131 g, 0.226 mmol) was combined with PhNCHPh (0.0422 g, 0.233 mmol) and CH₂Cl₂ (2 mL) and benzene (5 mL) to form a yellow suspension. The mixture was heated to 65° C. in a sealed vial. After 2 hours the homogeneous solution was evaporated to a residue that was dissolved in warm toluene (4 mL) and filtered. The mixture was concentrated to 1 mL then warmed to dissolve crystalline solid that had formed. After 30 minutes yellow crystals had formed which were isolated on a frit, washed with Et$_2$O. By $^1$H NMR spectroscopy the product cocrystallizes with 1.5 equivalents of toluene and is an 85:15 mixture of conformational diastereomers. Yield: 0.092 g, 50%.

Polymerizations Examples

General Polymerization Procedures

Ethylene/1-octene copolymerizations and propylene homopolymerizations were carried out in a parallel, pressure reactor, as generally described in U.S. Pat. No. 6,306,658; U.S. Pat. No. 6,455,316; U.S. Pat. No. 6,489,168; WO 00/09255; and Murphy et al., J. Am. Chem. Soc., 2003, 125, pages 4306-4317, each of which is fully incorporated herein by reference for US purposes. Although the specific quantities, temperatures, solvents, reactants, reactant ratios, pressures, and other variables are frequently changed from one polymerization run to the next, the following describes a typical polymerization performed in a parallel, pressure reactor.

A pre-weighed glass vial insert and disposable stirring paddle were fitted to each reaction vessel of the reactor, which contains 48 individual reaction vessels. The reactor was then closed and each vessel was individually heated to a set temperature (usually between 50 and 110° C.) and pressurized to a predetermined pressure of 1.38 MPa (usually between 75 and 400 psi, 2.76 MPa) ethylene. If desired, 1-octene (100 microliters, 637 micromol) was injected into each reaction vessel through a valve, followed by enough solvent (typically toluene or isohexane) to bring the total reaction volume, including the subsequent additions, to 5 mL. Tri-n-octylaluminum in toluene (100 microliters, 10 mM in toluene, 1 micromol) was then added to act as a co-catalyst/scavenger, if used.

The contents of the vessel were then stirred at 800 rpm. An activator solution (usually 1.0 molar equivalents of dimethyl anilinium tetrakis-pentafluorophenyl borate dissolved in toluene or 100-1000 molar equivalents of methyl alumoxane (MAO) in toluene) was then injected into the reaction vessel along with 500 microliters of toluene, followed by a toluene solution of catalyst (typically 0.40 mM in toluene, usually 20-40 nanomols of catalyst) and another aliquot of toluene (500 microliters). Equivalence is determined based on the mol equivalents relative to the moles of the transition metal in the catalyst complex.

The reaction was then allowed to proceed until a predetermined amount of ethylene (10 to 20 psi, (0.07 to 0.14 MPa)) had been taken up by the reaction (ethylene pressure was maintained in each reaction vessel at the pre-set level by computer control). At this point, the reaction was quenched by pressurizing the vessel with compressed air. After the polymerization reaction, the glass vial insert containing the polymer product and solvent was removed from the pressure cell and the inert atmosphere glove box, and the volatile components were removed using a Genevac HT-12 centrifuge and Genevac VC3000D vacuum evaporator operating at elevated temperature and reduced pressure. The vial was then weighed to determine the yield of the polymer product. The resultant polymer was analyzed by Rapid GPC (see below) to determine the molecular weight, by FT-IR (see below) to determine comonomer incorporation, and by DSC (see below) to determine melting point.

To determine various molecular weight related values by GPC, high temperature size exclusion chromatography was performed using an automated "Rapid GPC" system as generally described in U.S. Pat. No. 6,491,816; U.S. Pat. No. 6,491,823; U.S. Pat. No. 6,475,391; U.S. Pat. No. 6,461,515; U.S. Pat. No. 6,436,292; U.S. Pat. No. 6,406,632; U.S. Pat. No. 6,175,409; U.S. Pat. No. 6,454,947; U.S. Pat. No. 6,260,407; and U.S. Pat. No. 6,294,388; each of which is fully incorporated herein by reference for US purposes. This apparatus has a series of three 30 cm×7.5 mm linear columns, each containing PLgel 10 um, Mix B. The GPC system was calibrated using polystyrene standards ranging from 580-3,390,000 g/mol. The system was operated at an eluent flow rate of 2.0 mL/minutes and an oven temperature of 165° C. 1,2,4-trichlorobenzene was used as the eluent. The polymer samples were dissolved in 1,2,4-trichlorobenzene at a concentration of 0.1-0.9 mg/mL. 250 uL of a polymer solution was injected into the system. The concentration of the polymer in the eluent was monitored using an evaporative light scattering detector. The molecular weights presented are relative to linear polystyrene standards and are uncorrected.

Differential Scanning calorimetry (DSC) measurements were performed on a TA-Q100 instrument to determine the melting point of the polymers. Samples were pre-annealed at 220° C. for 15 minutes and then allowed to cool to room temperature overnight. The samples were then heated to 220° C. at a rate of 100° C./minutes and then cooled at a rate of 50° C./min. Melting points were collected during the heating period. The ratio of 1-octene to ethylene incorporated in the polymers (weight %) was determined by rapid FT-IR spectroscopy on a Bruker Equinox 55+ IR in reflection mode. Samples were prepared in a thin film format by evaporative deposition techniques. Weight percent 1-octene was obtained from the ratio of peak heights at 1378 and 4322 cm$^{-1}$. This method was calibrated using a set of ethylene/1-octene copolymers with a range of known wt % 1-octene content.

Effect of substitution at $R^{12}$ position on ethylene-octene copolymerization. The effect of substitution at the $R^{12}$ position on ethylene-octene copolymerization can be determined by comparing the performance of complex A ($R^{12}$=H) with complex I ($R^{12}$=2-isopropylphenyl) when activated under identical conditions. This experiment was performed and the results are shown in Table 2. Comparing runs 1-9 with runs 10-18 it is observed that in under all conditions explored (condition 1: no 1-octene, 80° C., 75 psi (0.52 MPa); condition 2: 0.127 mM 1-octene, 80° C., 75 psi (0.52 MPa); condition 3: 0.127 mM 1-octene, 80° C., 200 psi (1.38 MPa) the catalyst mixture formed from complex I (with $R^{12}$=2-isopropylphenyl) gave improved results in terms of higher activity, increased comonomer incorporation (not including condition 1, where no comonomer was present), and lower melting point compared to the catalyst mixture formed from complex A (with $R^{12}$=H).

TABLE 2

Effect of substitution at $R^{12}$ position on ethylene-octene copolymerization. Conditions: toluene solvent, total volume = 5 mL, 80° C., MAO activator (500 equivalents).

| run | complex | P (psig) | catalyst (mmol) | [C8] (mM) | activity* | wt % C8 | Mw | Mn | Mw/Mn | Tm* |
|---|---|---|---|---|---|---|---|---|---|---|
| 1 | A | 75 | 0.000025 | 0 | 4620 | 0.0 | 224,784 | 129,732 | 1.7 | 136.2 |
| 2 | A | 75 | 0.000025 | 0 | 5929 | 0.0 | 248,713 | 136,946 | 1.8 | 136.2 |

TABLE 2-continued

Effect of substitution at $R^{12}$ position on ethylene-octene copolymerization. Conditions: toluene solvent, total volume = 5 mL, 80° C., MAO activator (500 equivalents).

| run | complex | P (psig) | catalyst (mmol) | [C8] (mM) | activity* | wt % C8 | Mw | Mn | Mw/Mn | Tm* |
|---|---|---|---|---|---|---|---|---|---|---|
| 3 | A | 75 | 0.000025 | 0 | 7041 | 0.0 | 217,135 | 134,562 | 1.6 | 134.8 |
| 4 | A | 75 | 0.000025 | 0.127 | 7203 | 6.7 | 154,642 | 103,979 | 1.5 | 117.4 |
| 5 | A | 75 | 0.000025 | 0.127 | 5967 | 6.6 | 169,831 | 113,403 | 1.5 | 117.4 |
| 6 | A | 75 | 0.000025 | 0.127 | 5460 | 7.4 | 135,532 | 91,433 | 1.5 | 116.7 |
| 7 | A | 200 | 0.00002 | 0.127 | 6499 | 4.5 | 415,093 | 266,348 | 1.6 | 124.7 |
| 8 | A | 200 | 0.00002 | 0.127 | 6860 | 4.7 | 447,146 | 289,753 | 1.5 | 124.1 |
| 9 | A | 200 | 0.00002 | 0.127 | 7557 | 4.5 | 446,835 | 282,838 | 1.6 | 124.1 |
| 10 | I | 75 | 0.000025 | 0 | 14922 | 0.0 | | | | 135.5 |
| 11 | I | 75 | 0.000025 | 0 | 10984 | 0.0 | 623,938 | 328,357 | 1.9 | 134.1 |
| 12 | I | 75 | 0.000025 | 0 | 10028 | 0.0 | 247,468 | 122,638 | 2.0 | 133.7 |
| 13 | I | 75 | 0.000025 | 0.127 | 17636 | 9.6 | 279,519 | 189,770 | 1.5 | 113.5 |
| 14 | I | 75 | 0.000025 | 0.127 | 16873 | 12.6 | 304,897 | 202,227 | 1.5 | 114.5 |
| 15 | I | 75 | 0.000025 | 0.127 | 14972 | 11.6 | 246,542 | 168,886 | 1.5 | 112.7 |
| 16 | I | 200 | 0.00002 | 0.127 | 8735 | 6.3 | 707,872 | 495,114 | 1.4 | 121.8 |
| 17 | I | 200 | 0.00002 | 0.127 | 10301 | 5.5 | 377,032 | 234,941 | 1.6 | 121.9 |
| 18 | I | 200 | 0.00002 | 0.127 | 8826 | 5.7 | 290,824 | 158,565 | 1.8 | 121.9 |

*Activity is given in g of polymer/mmol catalyst/hour/bar; Tm is the first melt temperature given in degrees Celsius. 75 psi = 0.52 MPa, 200 psi = 1.38 MPa.

Effect of the LINKER group on ethylene-octene copolymerization. The effect of the LINKER group (see inset drawing in Table 1) on ethylene-octene copolymerization can be determined by comparing the performance of complex I (LINKER=phenyl) with complex M (LINKER=naphthyl) when activated under identical conditions. This experiment was performed and the results are shown in Table 3. Comparing runs 1-9 with runs 10-18 it is observed that in all runs where 1-octene was present (runs 4-9 and 13-18), the choice of the naphthyl LINKER group (i.e., complex M) in place of the phenyl LINKER group (i.e. complex I) gave a performance improvement in terms of activity. Additionally, higher % comonomer incorporation and lower Tm values for ethylene-octene copolymers produced with complex M compared to those produced with complex I, indicate that the naphthyl LINKER group had a desirable effect in terms of comonomer incorporation in the copolymer.

Effect of the LINKER group on ethylene-octene copolymerization. The effect of the LINKER group (see inset drawing in Table 1) on ethylene-octene copolymerization can be determined by comparing the performance of complex J (LINKER=phenyl) with complex N (LINKER=naphthyl) when activated under identical conditions. This experiment was performed and the results are shown in Table 4. Comparing runs 1-9 with runs 10-18 it is observed that in under all conditions explored (condition 1: no 1-octene, 80° C., 75 psi (0.52 MPa); condition 2: 0.127 mM 1-octene, 80° C., 75 psi (0.52 MPa); condition 3: 0.127 mM 1-octene, 80° C., 200 psi (1.38 MPa) the choice of the naphthyl LINKER group (i.e., complex N) in place of the phenyl LINKER group (i.e., complex J) gave no performance improvement in terms of activity. However, higher percent comonomer incorporation and lower Tm values for ethylene-octene copolymers produced with complex N compared to those produced with complex J,

TABLE 3

Effect of LINKER substitution on ethylene-octene copolymerization. Conditions: toluene solvent, total volume = 5 mL, 80° C., MAO activator (500 equivalents).

| run | complex | P (psig) | catalyst (mmol) | [C8] (mM) | activity* | wt % C8 | Mw | Mn | Mw/Mn | Tm* |
|---|---|---|---|---|---|---|---|---|---|---|
| 1 | I | 75 | 0.000025 | 0 | 10028 | 0.0 | 247,468 | 122,638 | 2.0 | 133.7 |
| 2 | I | 75 | 0.000025 | 0 | 10984 | 0.0 | 623,938 | 328,357 | 1.9 | 134.1 |
| 3 | I | 75 | 0.000025 | 0 | 14922 | 0.0 | n.a. | n.a. | n.a. | 135.5 |
| 4 | I | 75 | 0.000025 | 0.127 | 17636 | 9.6 | 279,519 | 189,770 | 1.5 | 113.5 |
| 5 | I | 75 | 0.000025 | 0.127 | 16873 | 12.6 | 304,897 | 202,227 | 1.5 | 114.5 |
| 6 | I | 75 | 0.000025 | 0.127 | 14972 | 11.6 | 246,542 | 168,886 | 1.5 | 112.7 |
| 7 | I | 200 | 0.00002 | 0.127 | 10301 | 5.5 | 377,032 | 234,941 | 1.6 | 121.9 |
| 8 | I | 200 | 0.00002 | 0.127 | 8826 | 5.7 | 290,824 | 158,565 | 1.8 | 121.9 |
| 9 | I | 200 | 0.00002 | 0.127 | 8735 | 6.3 | 707,872 | 495,114 | 1.4 | 121.8 |
| 10 | M | 75 | 0.000025 | 0 | 11346 | 0.0 | 435,594 | 254,014 | 1.7 | 133.7 |
| 11 | M | 75 | 0.000025 | 0 | 9144 | 0.0 | n.a. | n.a. | n.a. | 133.1 |
| 12 | M | 75 | 0.000025 | 0 | 9399 | 0.0 | 293,658 | 187,080 | 1.6 | 135.5 |
| 13 | M | 75 | 0.000025 | 0.127 | 23271 | 13.0 | 316,274 | 212,339 | 1.5 | 108.4 |
| 14 | M | 75 | 0.000025 | 0.127 | 24167 | 12.3 | 317,083 | 207,984 | 1.5 | 107.4 |
| 15 | M | 75 | 0.000025 | 0.127 | 24194 | 12.2 | 331,309 | 226,783 | 1.5 | 108.1 |
| 16 | M | 200 | 0.00002 | 0.127 | 16529 | 7.3 | 424,032 | 276,012 | 1.5 | 117.8 |
| 17 | M | 200 | 0.00002 | 0.127 | 13578 | 6.3 | 503,736 | 291,172 | 1.7 | 118.5 |
| 18 | M | 200 | 0.00002 | 0.127 | 13102 | 7.5 | 605,669 | 411,505 | 1.5 | 117.8 |

*Activity is given in g of polymer/mmol catalyst/hour/bar; Tm is the first melt temperature given in degrees Celsius. 75 psi = 0.52 MPa, 200 psi = 1.38 MPa.

indicate that the naphthyl LINKER group had a desirable effect in terms of comonomer incorporation in the copolymer.

Effect of the LINKER group on ethylene-octene copolymerization. The effect of the LINKER group (see inset drawing in Table 1) on ethylene-octene copolymerization can be determined by comparing the performance of complex Q (LINKER=phenyl) with complex S (LINKER=naphthyl) when activated under identical conditions. This experiment was performed and the results are shown in Table 5. Comparing runs 1-9 with runs 10-18 it is observed that the choice of the naphthyl LINKER group (i.e., complex S) in place of the phenyl LINKER group (i.e., complex Q) gave decreased catalyst activity. Additionally no significant performance improvement was observed in terms of % comonomer incorporation or lower Tm values for ethylene-octene copolymers.

Effect of the LINKER group on ethylene-octene copolymerization. The effect of the LINKER group (see inset drawing in Table 1) on ethylene-octene copolymerization can be determined by comparing the performance of complex R (LINKER=phenyl) with complex T (LINKER=naphthyl) when activated under identical conditions. This experiment was performed and the results are shown in Table 6. Comparing runs 1-9 with runs 10-18 it is observed that the choice of the naphthyl LINKER group (i.e., complex T) in place of the phenyl LINKER group (i.e., complex R) gave a performance improvement in terms of activity. Additionally, in those runs using 1-octene the naphthyl LINKER group resulted in higher % comonomer incorporation and lower Tm values for ethylene-octene copolymers.

TABLE 4

Effect of LINKER substitution on ethylene-octene copolymerization. Conditions: toluene solvent, total volume = 5 mL, 80° C., MAO activator (500 equivalents).

| run | complex | P (psig) | catalyst (mmol) | [C8] (mM) | activity* | wt % C8 | Mw | Mn | Mw/Mn | Tm* |
|---|---|---|---|---|---|---|---|---|---|---|
| 1 | J | 75 | 0.000025 | 0 | 17473 | 0.0 | 411,052 | 242,177 | 1.7 | 134.2 |
| 2 | J | 75 | 0.000025 | 0 | 17279 | 0.0 | 157,157 | 122,278 | 1.3 | 136.0 |
| 3 | J | 75 | 0.000025 | 0 | 16443 | 0.0 | 269,152 | 85,777 | 3.1 | 136.5 |
| 4 | J | 75 | 0.000025 | 0.127 | 23117 | 10.9 | 210,396 | 135,500 | 1.6 | 111.9 |
| 5 | J | 75 | 0.000025 | 0.127 | 21965 | 13.5 | 215,604 | 139,818 | 1.5 | 111.7 |
| 6 | J | 75 | 0.000025 | 0.127 | 22057 | 11.4 | 216,797 | 134,245 | 1.6 | 112.8 |
| 7 | J | 200 | 0.00002 | 0.127 | 14197 | 5.4 | 468,170 | 300,978 | 1.6 | 122.4 |
| 8 | J | 200 | 0.00002 | 0.127 | 14608 | 5.6 | 433,130 | 260,386 | 1.7 | 121.5 |
| 9 | J | 200 | 0.00002 | 0.127 | 13661 | 6.7 | 301,307 | 166,941 | 1.8 | 120.8 |
| 10 | N | 75 | 0.000025 | 0 | 15252 | 0.0 | 832,587 | 334,378 | 2.5 | 133.1 |
| 11 | N | 75 | 0.000025 | 0 | 14377 | 0.0 | 250,238 | 134,742 | 1.9 | 136.1 |
| 12 | N | 75 | 0.000025 | 0 | 16955 | 0.0 | 246,979 | 138,750 | 1.8 | 135.6 |
| 13 | N | 75 | 0.000025 | 0.127 | 20753 | 12.4 | 255,461 | 154,734 | 1.7 | 107.3 |
| 14 | N | 75 | 0.000025 | 0.127 | 23332 | 11.8 | 247,865 | 154,937 | 1.6 | 106.1 |
| 15 | N | 75 | 0.000025 | 0.127 | 25352 | 11.7 | 249,186 | 153,625 | 1.6 | 107.7 |
| 16 | N | 200 | 0.00002 | 0.127 | 11936 | 7.1 | 410,887 | 254,043 | 1.6 | 117.9 |
| 17 | N | 200 | 0.00002 | 0.127 | 12848 | 8.3 | 520,579 | 341,323 | 1.5 | 118.0 |
| 18 | N | 200 | 0.00002 | 0.127 | 12439 | 7.7 | 511,803 | 325,617 | 1.6 | 117.3 |

*Activity is given in g of polymer/mmol catalyst/hour/bar; Tm is the first melt temperature given in degrees Celsius. 75 psi = 0.52 MPa, 200 psi = 1.38 MPa.

TABLE 5

Effect of LINKER substitution on ethylene-octene copolymerization. Conditions: toluene solvent, total volume = 5 mL, 80° C., MAO activator (500 equivalents).

| run | complex | P (psig) | catalyst (mmol) | [C8] (mM) | activity* | wt % C8 | Mw | Mn | Mw/Mn | Tm* |
|---|---|---|---|---|---|---|---|---|---|---|
| 1 | Q | 75 | 0.000025 | 0 | 29,749 | 0.0 | 176,852 | 91,673 | 1.9 | 135.0 |
| 2 | Q | 75 | 0.000025 | 0 | 42,191 | 0.0 | 155,331 | 83,545 | 1.9 | 135.1 |
| 3 | Q | 75 | 0.000025 | 0 | 27,410 | 0.0 | 182,919 | 95,234 | 1.9 | 135.1 |
| 4 | Q | 75 | 0.000025 | 0.127 | 29,811 | 9.0 | 194,453 | 98,459 | 2.0 | 113.0 |
| 5 | Q | 75 | 0.000025 | 0.127 | 33,108 | 9.7 | 142,252 | 78,523 | 1.8 | 109.0 |
| 6 | Q | 75 | 0.000025 | 0.127 | 32,048 | 8.2 | 185,234 | 95,301 | 1.9 | 113.7 |
| 7 | Q | 200 | 0.00002 | 0.127 | 15,046 | 4.3 | 381,872 | 199,047 | 1.9 | 122.9 |
| 8 | Q | 200 | 0.00002 | 0.127 | 24,988 | 4.1 | 392,570 | 206,883 | 1.9 | 122.7 |
| 9 | Q | 200 | 0.00002 | 0.127 | 15,181 | 4.5 | 393,668 | 207,614 | 1.9 | 122.4 |
| 10 | S | 75 | 0.000025 | 0 | 9,032 | 0.0 | 168,283 | 87,099 | 1.9 | 135.1 |
| 11 | S | 75 | 0.000025 | 0 | 15,415 | 0.0 | 164,350 | 90,670 | 1.8 | 135.3 |
| 12 | S | 75 | 0.000025 | 0 | 7,132 | 0.0 | 188,556 | 94,105 | 2.0 | 135.4 |
| 13 | S | 75 | 0.000025 | 0.127 | 13,043 | 9.8 | 165,494 | 91,827 | 1.8 | 112.1 |
| 14 | S | 75 | 0.000025 | 0.127 | 17,444 | 9.7 | 153,102 | 89,954 | 1.7 | 113.5 |
| 15 | S | 75 | 0.000025 | 0.127 | 16,218 | 9.4 | 158,843 | 94,280 | 1.7 | 111.9 |
| 16 | S | 200 | 0.00002 | 0.127 | 13,498 | 4.9 | 361,038 | 203,971 | 1.8 | 121.9 |
| 17 | S | 200 | 0.00002 | 0.127 | 14,492 | n.a. | n.a. | n.a. | n.a. | n.a. |
| 18 | S | 200 | 0.00002 | 0.127 | 13,252 | 4.5 | 371,471 | 207,299 | 1.8 | 122.8 |

*Activity is given in g of polymer/mmol catalyst/hour/bar; Tm is the first melt temperature given in degrees Celsius. 75 psi = 0.52 MPa, 200 psi = 1.38 MPa.

TABLE 6

Effect of LINKER substitution on ethylene-octene copolymerization. Conditions: toluene solvent, total volume = 5 mL, 80° C., MAO activator (500 equivalents).

| run | complex | P (psig) | catalyst (mmol) | [C8] (mM) | activity* | wt % C8 | Mw | Mn | Mw/Mn | Tm* |
|---|---|---|---|---|---|---|---|---|---|---|
| 1 | R | 75 | 0.000025 | 0 | 9,558 | 0.0 | 91,881 | 59,487 | 1.5 | 134.3 |
| 2 | R | 75 | 0.000025 | 0 | 6,842 | 0.0 | 93,817 | 58,623 | 1.6 | 134.0 |
| 3 | R | 75 | 0.000025 | 0 | 9,743 | 0.0 | 93,202 | 59,822 | 1.6 | 134.3 |
| 4 | R | 75 | 0.000025 | 0.127 | 11,312 | 6.5 | 92,643 | 58,856 | 1.6 | 116.2 |
| 5 | R | 75 | 0.000025 | 0.127 | 9,542 | 6.2 | 97,502 | 62,281 | 1.6 | 115.9 |
| 6 | R | 75 | 0.000025 | 0.127 | 11,949 | 6.2 | 87,862 | 55,748 | 1.6 | 116.2 |
| 7 | R | 200 | 0.00002 | 0.127 | 11,551 | 3.8 | 196,983 | 124,952 | 1.6 | 124.6 |
| 8 | R | 200 | 0.00002 | 0.127 | 10,477 | 3.1 | 204,553 | 130,521 | 1.6 | 124.4 |
| 9 | R | 200 | 0.00002 | 0.127 | 10,157 | 3.0 | 204,742 | 130,800 | 1.6 | 124.7 |
| 10 | T | 75 | 0.000025 | 0 | 18,602 | 0.0 | 133,790 | 81,242 | 1.6 | 135.1 |
| 11 | T | 75 | 0.000025 | 0 | 15,590 | 0.0 | 130,758 | 79,894 | 1.6 | 135.6 |
| 12 | T | 75 | 0.000025 | 0 | 17,312 | 0.0 | 125,094 | 76,013 | 1.6 | 135.5 |
| 13 | T | 75 | 0.000025 | 0.127 | 23,482 | 10.1 | 136,521 | 85,819 | 1.6 | 109.3 |
| 14 | T | 75 | 0.000025 | 0.127 | 22,925 | 9.1 | 142,392 | 91,812 | 1.6 | 109.8 |
| 15 | T | 75 | 0.000025 | 0.127 | 22,251 | 10.0 | 121,606 | 79,031 | 1.5 | 110.3 |
| 16 | T | 200 | 0.00002 | 0.127 | 14,823 | 5.1 | 273,431 | 174,882 | 1.6 | 120.3 |
| 17 | T | 200 | 0.00002 | 0.127 | 15,008 | 4.8 | 295,295 | 188,906 | 1.6 | 121.3 |
| 18 | T | 200 | 0.00002 | 0.127 | 13,622 | 5.4 | 293,526 | 185,523 | 1.6 | 120.1 |

*Activity is given in g of polymer/mmol catalyst/hour/bar; Tm is the first melt temperature given in degrees Celsius. 75 psi = 0.52 MPa, 200 psi = 1.38 MPa.

Effect of substitution at $R^{12}$ position on propylene polymerization. The effect of substitution at the $R^{12}$ position on propylene polymerization can be determined by comparing the performance of complex D ($R^{12}$=H) with that of complex L ($R^{12}$=2-isopropyl phenyl) when both are activated under identical conditions. Similarly the performance of complex H ($R^{12}$=H) can be compared to that of complex P ($R^{12}$=2-isopropyl phenyl) when both are activated under identical conditions. These experiments were performed and the results are shown in Table 7. Comparing runs 1-6 with runs 7-12 it is observed that in under both conditions explored (70 and 100° C.) the catalyst mixture formed from complex L ($R^{12}$=2-isopropylphenyl) was preferred over that formed from complex D ($R^{12}$=H) in that it produced polypropylene with a much higher (+50° C.) melting point. Similarly, comparing runs 13-18 with runs 19-23 it is observed that in under both conditions explored (70 and 100° C.) the catalyst mixture formed from complex P ($R^{12}$=2-isopropylphenyl) was preferred over that formed from complex H ($R^{12}$=H) in that it produced polypropylene with a much higher (+40° C.) melting point.

TABLE 7

Effect of substitution at $R^{12}$ position on propylene polymerization. Conditions: isohexane solvent, propylene added = 1 mL, total volume = 5 mL, N,N-dimethylanilinium tetrakis(pentafluorophenyl)borate activator(1.0 equivalent).

| run | complex | T (° C.) | Catalyst (mmol) | activity* | Mw | Mn | Mw/Mn | Tm* |
|---|---|---|---|---|---|---|---|---|
| 1 | D | 70 | 0.00008 | 121,455 | 815,843 | 442,811 | 1.8 | 92.6 |
| 2 | D | 70 | 0.00008 | 50,873 | 1,023,224 | 657,708 | 1.6 | 94.7 |
| 3 | D | 70 | 0.00008 | 34,770 | | | | 93.8 |
| 4 | D | 100 | 0.00008 | 81,889 | 264,139 | 164,974 | 1.6 | 88.1 |
| 5 | D | 100 | 0.00008 | 57,726 | 254,458 | 162,415 | 1.6 | 90.1 |
| 6 | D | 100 | 0.00008 | 97,383 | 236,646 | 147,669 | 1.6 | 85.8 |
| 7 | L | 70 | 0.00008 | 90,650 | 803,809 | 429,397 | 1.9 | 143.4 |
| 8 | L | 70 | 0.00008 | 73,504 | 943,783 | 481,147 | 2.0 | 143.7 |
| 9 | L | 70 | 0.00008 | 81,136 | 955,506 | 511,344 | 1.9 | 143.3 |
| 10 | L | 100 | 0.00008 | 66,391 | 202,838 | 107,597 | 1.9 | 139.9 |
| 11 | L | 100 | 0.00008 | 66,655 | 190,351 | 101,609 | 1.9 | 139.9 |
| 12 | L | 100 | 0.00008 | 59,799 | 197,229 | 98,622 | 2.0 | 138.9 |
| 13 | H | 70 | 0.00008 | 71,060 | 650,608 | 417,538 | 1.6 | 107.3 |
| 14 | H | 70 | 0.00008 | 75,206 | 522,409 | 323,176 | 1.6 | 107.9 |
| 15 | H | 70 | 0.00008 | 79,192 | 597,601 | 392,869 | 1.5 | 106.3 |
| 16 | H | 100 | 0.00008 | 83,059 | 149,835 | 100,050 | 1.5 | 101.8 |
| 17 | H | 100 | 0.00008 | 68,308 | 151,593 | 100,799 | 1.5 | 103.5 |
| 18 | H | 100 | 0.00008 | 68,358 | 156,601 | 101,056 | 1.5 | 105.3 |
| 19 | P | 70 | 0.00008 | 87,990 | 586,834 | 271,112 | 2.2 | 150.6 |
| 20 | P | 70 | 0.00008 | 69,097 | 580,237 | 256,491 | 2.3 | 150.8 |
| 21 | P | 70 | 0.00008 | 77,955 | 585,030 | 265,469 | 2.2 | 150.0 |
| 22 | P | 100 | 0.00008 | 53,156 | 85,377 | 44,901 | 1.9 | 145.8 |
| 23 | P | 100 | 0.00008 | 70,816 | 91,806 | 47,143 | 1.9 | 146.1 |

*Activity is given in g of polymer/mmol catalyst/hour; Tm is the first melt temperature given in degrees Celsius.

Effect of the LINKER group on propylene polymerization. The effect of the LINKER group (see inset drawing in Table 1) on propylene polymerization can be determined by comparing the performance of complex L (LINKER=phenyl) with complex P (LINKER=naphthyl) when activated under identical conditions. This experiment was performed and the results are shown in Table 8. Comparing runs 1-6 with runs 7-11 it is observed that in under both conditions explored (70 and 100° C.) the catalyst mixture formed from complex P (LINKER=naphthyl) was preferred over that formed from complex L (LINKER=phenyl) in that it produced polypropylene with a significantly higher (+6 to 7° C.) melting point.

TABLE 8

Effect of LINKER on propylene polymerization. Conditions: isohexane solvent, propylene added = 1 mL, total volume = 5 mL, N,N-dimethylanilinium tetrakis(pentafluorophenyl)borate activator (1.0 equivalent).

| run | complex | T (° C.) | catalyst (mmol) | activity* | Mw | Mn | Mw/Mn | Tm* |
|---|---|---|---|---|---|---|---|---|
| 1 | L | 70 | 0.00008 | 90,650 | 803,809 | 429,397 | 1.9 | 143.4 |
| 2 | L | 70 | 0.00008 | 73,504 | 943,783 | 481,147 | 2.0 | 143.7 |
| 3 | L | 70 | 0.00008 | 81,136 | 955,506 | 511,344 | 1.9 | 143.3 |
| 4 | L | 100 | 0.00008 | 66,391 | 202,838 | 107,597 | 1.9 | 139.9 |
| 5 | L | 100 | 0.00008 | 66,655 | 190,351 | 101,609 | 1.9 | 139.9 |
| 6 | L | 100 | 0.00008 | 59,799 | 197,229 | 98,622 | 2.0 | 138.9 |
| 7 | P | 70 | 0.00008 | 87,990 | 586,834 | 271,112 | 2.2 | 150.6 |
| 8 | P | 70 | 0.00008 | 69,097 | 580,237 | 256,491 | 2.3 | 150.8 |
| 9 | P | 70 | 0.00008 | 77,955 | 585,030 | 265,469 | 2.2 | 150.0 |
| 10 | P | 100 | 0.00008 | 53,156 | 85,377 | 44,901 | 1.9 | 145.8 |
| 11 | P | 100 | 0.00008 | 70,816 | 91,806 | 47,143 | 1.9 | 146.1 |

*Activity is given in g of polymer/mmol catalyst/hour; Tm is the first melt temperature given in degrees Celsius.

Effect of tri(n-octyl)aluminum concentration on propylene polymerization. The effect of tri(n-octyl)aluminum (TNOAL) concentration on the molecular weight of polypropylene produced with complex P when activated was evaluated. These results of these experiments are shown in Table 9. Comparing runs 1-8 it is observed that the molecular weight of the polypropylene produced drops dramatically as the amount of TNOAL is increased from 300 nmol to 2400 nmol. This data suggests that polymeryl group transfer between the Hf center and Al occurs. This suggests that pyridyl diamide based catalysts may be used with chain transfer agents, such as dialkylzincs and trialkyl aluminums, to either tailor molecular weight and polydispersity or to prepare linear block polymers in processes using either a single or Multiple catalysts.

For purposes of the claims, the following test methods shall be used.

$^1$H NMR $^1$H NMR data is collected at 120° C. shall be used in a 5 mm probe using a spectrometer with a $^1$H frequency of at least 400 MHz. Data is recorded using a maximum pulse width of 45°, 8 seconds between pulses and signal averaging 120 transients. Spectral signals are integrated. Samples are dissolved in deuterated methylene chloride at concentrations between 10 to 15 wt % prior to being inserted into the spectrometer magnet. Prior to data analysis, spectra are referenced by setting the residual CHDCl$_2$ resonance to 5.24 ppm.

$^{13}$C NMR $^{13}$C NMR data is collected at 120° C. using a spectrometer with a $^{13}$C frequency of at least 75 MHz. A 90 degree pulse, an acquisition time adjusted to give a digital resolution between 0.1 and 0.12 Hz, at least a 10 second pulse acquisition delay time with continuous broadband proton decoupling using swept square wave modulation without gating is employed during the entire acquisition period. The spectra are acquired with time averaging to provide a signal to noise level adequate to measure the signals of interest. Samples are dissolved in deuterated methylene chloride at concentrations between 10 to 15 wt % prior to being inserted into the spectrometer magnet. Prior to data analysis, spectra are referenced

TABLE 9

Effect of TNOAL concentration on propylene polymerization. Conditions: isohexane solvent, propylene added = 1 mL, total volume = 5 mL, N,N-dimethylanilinium tetrakis(pentafluorophenyl)borate activator (1.0 equivalent), 50° C.

| run | complex | TNOAL (nmol) | catalyst (mmol) | activity* | Mw | Mn | Mw/Mn | Tm* |
|---|---|---|---|---|---|---|---|---|
| 1 | P | 300 | 0.00004 | 84351 | 2,859,249 | 1,490,946 | 1.9 | 150.9 |
| 2 | P | 300 | 0.00004 | 83731 | 2,567,415 | 1,689,133 | 1.5 | 151.2 |
| 3 | P | 600 | 0.00004 | 86194 | 2,395,775 | 1,181,821 | 2.0 | 151.6 |
| 4 | P | 600 | 0.00004 | 63241 | 2,038,824 | 1,475,834 | 1.4 | 151.7 |
| 5 | P | 1200 | 0.00004 | 62168 | 1,402,568 | 474,806 | 3.0 | 151.8 |
| 6 | P | 1200 | 0.00004 | 76113 | 1,510,096 | 956,202 | 1.6 | 152.6 |
| 7 | P | 2400 | 0.00004 | 59751 | 1,251,391 | 729,008 | 1.7 | 152.1 |

*Activity is given in g of polymer/mmol catalyst/hour; Tm is the first melt temperature given in degrees Celsius.

by setting the chemical shift of the deuterated methylene chloride solvent signal to 54 ppm.

All documents described herein are incorporated by reference herein for purposes of all jurisdictions where such practice is allowed, including any priority documents and/or testing procedures to the extent they are not inconsistent with this text, provided however that any priority document not named in the initially filed application or filing documents is NOT incorporated by reference herein. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law. Likewise whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

What is claimed is:

1. A pyridyldiamido transition metal complex represented by the formula: (I), (II), or (III):

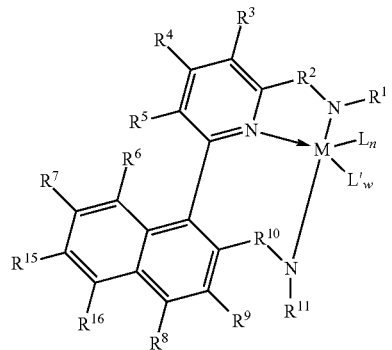

(I)

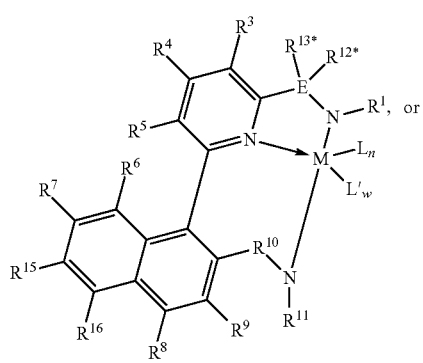

(II)

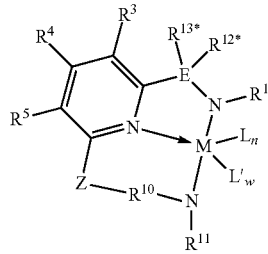

(III)

wherein:

M is a Group 3, 4, 5, 6, 7, 8, 9, 10, 11, or 12 metal;

$R^1$ and $R^{11}$ are independently selected from the group consisting of hydrocarbyls, substituted hydrocarbyls, and silyl groups;

$R^2$ and $R^{10}$ are each, independently, $-E(R^{12})(R^{13})-$;

E is carbon, silicon, or germanium;

each $R^{12}$, $R^{13}$, $R^{12*}$, and $R^{13*}$ is independently selected from the group consisting of hydrogen, hydrocarbyl, and substituted hydrocarbyl, alkoxy, silyl, amino, aryloxy, halogen, and phosphino, $R^{12}$ and $R^{13}$ and/or $R^{12*}$ and $R^{13*}$ may be joined to form a saturated, substituted or unsubstituted hydrocarbyl ring, where the ring has 4, 5, 6, or 7 ring carbon atoms and where substitutions on the ring can join to form additional rings, or $R^{12}$ and $R^{13}$ and/or $R^{12*}$ and $R^{13*}$ may be joined to form a saturated heterocyclic ring, or a saturated substituted heterocyclic ring where substitutions on the ring can join to form additional rings, provided that at least one of $R^{12*}$ and $R^{13*}$ is a $C_1$ to $C_{100}$ substituted or unsubstituted hydrocarbyl group;

$R^3$, $R^4$, and $R^5$ are independently selected from the group consisting of hydrogen, hydrocarbyls, substituted hydrocarbyls, alkoxy, aryloxy, halogen, amino, and silyl, and wherein adjacent R groups ($R^3$ & $R^4$ and/or $R^4$ & $R^5$) may be joined to form a substituted or unsubstituted hydrocarbyl or heterocyclic ring, where the ring has 5, 6, 7, or 8 ring atoms and where substitutions on the ring can join to form additional rings;

$R^6$, $R^7$, $R^8$, $R^9$, $R^{15}$, and $R^{16}$ are independently selected from the group consisting of hydrogen, hydrocarbyls, substituted hydrocarbyls, alkoxy, halogen, amino, and silyl, and the pairs of positions, and wherein adjacent R groups ($R^6$ & $R^7$, and/or $R^7$ & $R^{15}$, and/or $R^{16}$ & $R^{15}$, and/or $R^8$ & $R^9$) may be joined to form a saturated, substituted or unsubstituted hydrocarbyl or heterocyclic ring, where the ring has 5, 6, 7, or 8 ring carbon atoms and where substitutions on the ring can join to form additional rings;

L is an anionic leaving group, where the L groups may be the same or different and any two L groups may be linked to form a dianionic leaving group;

n is 0, 1, 2, 3, or 4;

L' is neutral Lewis base;

w is 0, 1, 2, 3, or 4;

Z is $-(R^{14*})_p$-Q-J$(R^{15*})_q-$ where Q or J is bonded to $R^{10}$;

J is C or Si;

Q is C, O, N, or Si;

$R^{14*}$ and $R^{15*}$ are independently selected from the group consisting of hydrogen, hydrocarbyls, and substituted hydrocarbyls, and wherein adjacent $R^{14*}$ and $R^{15*}$ groups may be joined to form an aromatic or saturated, substituted or unsubstituted hydrocarbyl ring, where the ring has 5, 6, 7, or 8 ring carbon atoms and where substitutions on the ring can join to form additional rings;

p is 1 or 2; and q is 1 or 2.

2. The complex of claim 1, wherein M is Ti, Zr, or Hf.

3. The complex of claim 1, wherein $R^2$ and $R^{10}$ are each, independently, represented by the formula:

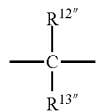

where $R^{12''}$ is hydrogen, alkyl, aryl, or halogen; and $R^{13''}$ is hydrogen, alkyl, aryl, or halogen.

4. The complex of claim 1, wherein $R^6, R^7, R^8, R^9, R^{15}$, and $R^{16}$ are independently selected from the group consisting of hydrogen, hydrocarbyls, substituted hydrocarbyls, alkoxy, halogen, amino, and silyl.

5. The complex of claim 1, wherein $R^1, R^3, R^4, R^5, R^{11}$ each contain no more than 30 carbon atoms.

6. The complex of claim 4, wherein $R^1, R^3, R^4, R^5, R^6, R^7, R^8, R^9$, and $R^{15}$ each contain no more than 30 carbon atoms.

7. The complex of claim 1, wherein E is carbon and $R^1$ and $R^{11}$ are independently selected from phenyl groups that are substituted with 0, 1, 2, 3, 4, or 5 substituents selected from the group consisting of F, Cl, Br, I, $CF_3$, $NO_2$, alkoxy, dialkylamino, hydrocarbyl, and substituted hydrocarbyls groups with from one to ten carbons.

8. The complex of claim 1, wherein each L is independently selected from the group consisting of halide, alkyl, aryl, alkoxy, amido, hydrido, phenoxy, hydroxy, silyl, allyl, alkenyl, triflate, alkylsulfonate, arylsulfonate, and alkynyl; and each L' is independently selected from the group consisting of ethers, thio-ethers, amines, nitriles, imines, pyridines, and phosphines.

9. The complex of claim 1, wherein the complex is represented by formula (I) and both $R^{12}$ and $R^{13}$ are a $C_1$ to $C_{100}$ alkyl group.

10. The complex of claim 1, wherein the complex is represented by formula (I).

11. The complex of claim 1, wherein the complex is represented by formula (II).

12. The complex of claim 1, wherein the complex is represented by formula (III).

13. The complex of claim 1, wherein the complex is represented by formula (III) and $R^{12*}$ is H, $R^{13*}$ is a group containing from 1 to 100 carbons, M is a Group 4 metal, E is carbon and $R^{10}$ is $CH_2$.

14. The complex of claim 1, wherein the complex is represented by formula (II) and $R^{12*}$ is a group containing from 1 to 100 carbons, M is a Group 4 metal, E is carbon and $R^{10}$ is $CH_2$.

15. The complex of claim 1, wherein the complex is represented by formula (I) and $R^{12}$ is H, $R^{13}$ is a group containing from 1 to 100 carbons, M is a Group 4 metal, E* is carbon and $R^{10}$ is $CH_2$.

16. A process for preparing the pyridyldiamido complex of claim 2, comprising reaction of a pyridyldiamine with a group 4 transition metal complex of the general formula $MY_2L_2L'_w$, where M is Ti, Zr, or Hf, Y is a deprotonated amine or hydrocarbanion group; L is an anionic leaving group, where the L and Y groups may be the same or different and any two L and/or Y groups may be linked to form a dianionic group; L' is neutral Lewis base; and w is 0, 1, 2, 3, or 4.

17. A catalyst system comprising an activator and the complex of claim 1.

18. The catalyst system of claim 17, wherein the activator is an alumoxane.

19. The catalyst system of claim 17, wherein the activator is a non-coordinating anion.

20. A polymerization process comprising a) contacting one or more alkene monomers with a catalyst system comprising: i) an activator and ii) the pyridyldiamido transition metal complex of claim 1.

21. The process of claim 20, wherein the activator is an alumoxane.

22. The process of claim 20, wherein the activator is a non-coordinating anion.

23. The process of claim 20, wherein the monomer comprises ethylene.

24. The process of claim 20, wherein the monomer comprises propylene.

25. The process of claim 20, wherein the pyridyldiamido transition metal complex is supported.

26. The process of claim 20, wherein $R_6, R_7, R_8$, and $R_9$ are independently selected from the group consisting of hydrogen, hydrocarbyls, substituted hydrocarbyls, alkoxy, halogen, amino, and silyl.

\* \* \* \* \*